US006451546B1

(12) United States Patent
Coruzzi et al.

(10) Patent No.: US 6,451,546 B1
(45) Date of Patent: Sep. 17, 2002

(54) PLANT GLUTAMATE RECEPTORS

(75) Inventors: Gloria Coruzzi; Igor Oliveira; Hon-Ming Lam, all of New York; Ming-Hsiun Hsieh, Woodside, all of NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 09/406,640

(22) Filed: Sep. 27, 1999

Related U.S. Application Data

(60) Division of application No. 08/658,335, filed on Jun. 5, 1996, now Pat. No. 5,981,703, which is a continuation-in-part of application No. 08/629,291, filed on Apr. 8, 1996, now Pat. No. 5,959,174, which is a continuation-in-part of application No. 08/481,956, filed on Jun. 7, 1995, now Pat. No. 5,824,867.

(51) Int. Cl.$^7$ .......................... G01N 33/48; G01N 33/53

(52) U.S. Cl. ................... 435/7.2; 435/7.1; 435/69.1; 436/501

(58) Field of Search ........................... 436/501; 435/7.1, 435/69.1, 7.2

(56) References Cited

U.S. PATENT DOCUMENTS

| | | | |
|---|---|---|---|
| 5,202,257 A | | 4/1993 | Hienemann et al. ........ 435/325 |
| 5,824,867 A | * | 10/1998 | Coruzzi et al. |
| 5,959,174 A | * | 9/1999 | Coruzzi et al. |
| 5,981,703 A | * | 11/1999 | Coruzzi et al. |

OTHER PUBLICATIONS

Ngo et al., 1994, The Protein Folding Problem and Tertiary Structure Prediction, Merz et al., eds., Birkhauser, Boston, pp. 491–495.*
Wells, 1990, Biochemistry 29:8509–8517.*
Anis et al., 1979, "Plant Lectins and Desensitization of Locust Glutamate Receptors", J. Physiology 291:47P.
Balke, 1985, In: Week Physiology. CRC Press, Inc. pp 113–139.
Baskys, 1992, "Metabolic Receptors and Slow Excitatory Actions of Glutamate Agonists in the Hippocampus", TINS 15:92–96.
Bowie et al., 1990, "Deciphering the message in protein sequences: Tolerance to amino acid substitutions." Science 247:1306–1310.
Burnashev et al., 1992, "Divalent Ion Permeability of AMPA Receptor Channels Is Dominated by the Edited Form of A Single Subunit", Neuron 8:189–198.
Choi, 1988, "Glutamate Neurotoxicity and Diseases of the Nervous System", Neuron 1:623–634.
Condorelli et al., 1994, "Glutamate Receptor–Driven Activation of Transcription Factors in Primary Neuronal Cultures", Neurochem Res. 19:489–499.

Condorelli et al., 1993, "Induction of Primary Response Genes by Excitatory Amino Acid Receptor Agonists in Primary Astroglial Cultures", J. Neurochem. 60:877–885.
Cunningham et al., 1993, "Excitatory Amino Acid Receptors: A Gallery of New Targets for Pharmacological Intervention", Life Sciences 54:135–148.
Gasic et al., 1992, "Molecular Neurobiology of Glutamate Receptors", Annu. Rev. Phuysiol. 54:507–536.
Graham et al., 1990, "Injection of Excritory Amino Acid Antagonists into the Medical Pallidal Segment of a 1–Methyl–4Phenyl–1,2,3,6–Teterahydropyridine" Life Sci 47:91–97.
Hofmann and W. Stoffel, 1993, TMbase—A database of membrane spanning proteins segments, Biol. Chem. Hoppe–Seyler 347,166.
Hume et al., 1991, "Identification of a Site in Glutamate Receptor Subunits That Controls Calcium Permeability", Science 253:1028–1031.
Kanai et al., 1993, "The Elusive Transporters with a High Affinity for Glutamate" TINS 16:365–370.
Kennedy, 1989, "Regulation of Synaptic Transmission in the Central Nervous System: Long–Term Potentiation", Cell 59:777–787.
Kohler et al., 1993, "Determinants of $Ca^{2+}$ Permeability in Both TM1 and TM2 of High Affinity Kainate Receptor Channels: Diversity by RNA Editing", Neuron 10:491–500.
Kuryatov et al., 1994, "Mutation Analysis of the Glycine Binding Site of NMDA Receptor" Neuron 12:1291–1300.
Lam et al., 1994, Metabolic Regulation of the Gene Encoding Glutamine–Dependent Asparagine Synthetase in *Arabidopsis thaliana*, Plant Physiol. 106:1347–1357.
Lea et al., 1988, "The Use of Mutants Lacking Glutamine Synthetase and Glutamate Synthase to Study Their Role in Plant Nitrogen Metabolism", Recent Advances in Phytochemistry (Plenum Press, New York) pp. 157–189.
Lea and Miflin, 1980, "Transport and Metabolism of Asparagine and Other Nitrogen Compounds within the Plant", *The Biochemistry of Plants* (Academic Press, New York) pp. 569–607.
Lee et al., 1990, in: *The Biochemistry of Plants*, vol. 16, edited by Stumpf and Conn: Plenum Press, pp. 121–155.
Melo–Oliveira et al., 1996, "Arabidopsis Mutant Analysis and Gene Regulation Define a Nonredundant Role for Glutamate Dehydrogenase in Nitrogen Assimilation", Proc. Natl. Acad. Sci. USA 93:4718–4723.
Minakami et al., 1994, "Molecular Cloning and the Functional Expression of Two Isoforms of Human Metabotropic Glutamate Receptor Subtype 5", Biochem. Biophys. Res. Commun. 199:1136–1143.

(List continued on next page.)

*Primary Examiner*—Elizabeth Kemmerer
(74) *Attorney, Agent, or Firm*—Pennie & Edmonds LLP

(57) ABSTRACT

The present invention relates to a family of GluR in plants, including ionotropic (iGluR), metabotropic (mGluR) and other glutamate-like plant receptors. The plant GluRs of the invention may function as signal transducers involved in the regulation of plant growth. The invention also relates to the identification of compounds that modulate the activity of the plant GluR, and the use of such compounds as plant growth regulators, including herbicides.

7 Claims, 46 Drawing Sheets

OTHER PUBLICATIONS

Figure 1A:
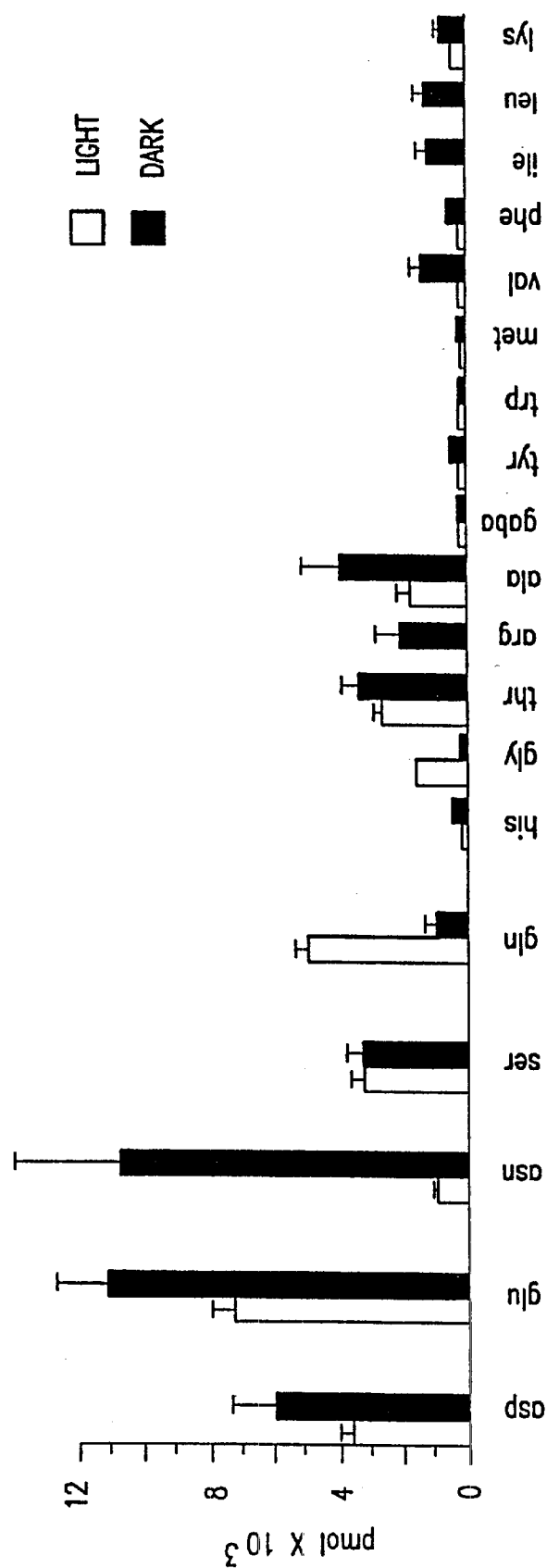

Monaghan et al., 1989, "The Excitatory Amino Acid Receptors: Their Classes, Pharmacology, and Distinct Properties in the Function of the Central Nervous System", Annu. Rev. Pharmacol. Toxic. 29:365–402.

Nakanishi et al., 1994, "Molecular Diversity of Glutamate Receptors and their Physiological Functions", *Toward a Molecular Basis of Alcohol Use and Abuse* (Birkhauser, Boston) pp. 71–80.

Newman et al., 1994, "Genes Galore: A Summary of Models For Accessing Results from Large Scale Partial Sequencing of Anonymous Arabidopsis cDNA Clones" Plant Physiol. 106:1241–1255.

O'Hara et al., 1993, "The Ligand Bonding Domain in Metabotropic Glutamate Receptors is Related to Bacterial Periplasmic Binding Proteins" Neuron 11:41–52.

Papp and Morly, 1994, "Antidepressant Activity of Non–competitive and Competitive NMDA Receptor Antagonists in a Chronic Mild Stress Model of Depression" Eur. J. Pharmacology 263:1–7.

Ratajczak et al., 1981, "The Effect of Different Carbon and Nitrogen Sources on the Activity of Glutamine Synthetase and Glutamate Dehydrogenase in Lupine Embryonic Axes", Physiol. Plant 51:277–280.

Ross et al., 1988, "Excitoxic Principles of Plants Linked to Neuronal Diseases Involving Motor and Other Systems", *Frontiers in Excitatory Amino Acid Research* (Alan R. Liss, Inc. New York) pp. 517–521.

Saur et al. 1987, "The Effect of Phosphinothricin (Glufosinate) on Photosynthesis II. The Causes of Inhibition of Photosynthesis", Z. Naturforsch. 42:270–278.

Schoepp and Conn, 1993, "Metabotropic Glutamate Receptors in Brain Function and Pathology", Trends in Pharmacol. Sci. 14:13–20.

Schulz et al., 1979, Principles of Protein structure, Springer–Verlag, New York, pp. 14–16.

Seeburg, 1993, "The Molecular Biology of Mammalian Glutamate Receptor Channels", TINS 16:359–365.

Sommer et al., 1991, "RNA Editing in Brain Controls a Determinant of Ion Flow in Glutamate–Gated Channels", Cell 67:11–19.

Sommer et al., 1990, "Flip and Flop: A Cell–Specific Switch in Glutamate–Operated Channels of the CNS", Science 249:1580–1585.

Stern–Bach et al., 1994, "Agonists Selectivity of Glutamate Receptor Is Specified by Two Domains Structurally Related to Bacterial Amino Acid–Binding Proteins", Neuron 13:1345–1357.

Tsai et al., 1990 "Dark–Induced and Organ–Specific Expression of Two Asparagine Synthetase Genes in *Pisum Sativum*", EMBO 9:323–332.

Urquhart and Joy, 1981, "Use of Phloem Exudate Techniques in the Study of Amino Acid Transport in Pea Plants", Plant Physiol. 68:750–754.

Vincentz et al., 1993, "Regulation of Nitrate and Nitrite Reductase Expression in *Nicotiana plumbaginifolia* Leaves by Nitrogen and Carbon Metabolites" Plant J. 3:315–324.

* cited by examiner

| | Metabolic Conditions | Nitrogen Flow | Active Genes |
|---|---|---|---|
| A | LIGHT or High Sucrose → High C:N | N → Gln + Glu | GLN2, GLU1 |
| B | DARK or Low Sucrose → Low C:N | N → Gln → Asn<br>Glu → $NH_4^+$ | ASN1<br>GDH |

FIG. 4

|          |                  |           |                                               |
|----------|------------------|-----------|-----------------------------------------------|
| BACTERIA | E. COLI GlnH     | (58–98)   | QTKNVDLALAGITITDERKKAIDFSDGYYKSGLLVMVKANN      |
|          |                  |           |                                               |
| ANIMAL   | CHICK KBP        | (90–130)  | LRQEADIAVAPLTITSAREEVVSFTTPFLQTGIGILLRKET      |
|          | FROG KBP         | (89–129)  | IRKEADLAIAPLTITSVRENAISFTKPFMQTGIGILLKKDT      |
|          | RAT GluR-K1      | (464–504) | VYGRADIAVAPLTITLVREEVIDFSKPFMSLGISIMIKKPQ      |
|          | RAT GluR-K2      | (470–510) | VYGRADIAVAPLTITLVREEVIDFSKPFMSLGISIMIKKPQ      |
|          | RAT GluR-K3      | (468–508) | VYGKADIAIAPLTITLVREEVIDFSKPFMSLGISIMIKKPQ      |
|          |                  |           |        * *   ****  ****      ****   *         |
| PLANT    | ARABIDOPSIS GluR |           | QRDKYDAAVGDITITSNRSLYVDFTLPYTDIGIGILTVKKK      |

FIG. 6

```
                                      10        20        30↓       40
At-iGluR              RGNNDNLAYLLSTQRDKYDAAVGDITITSNRSLYVDFTLPYT
                      |||::||:::||  |||::|:::
NMDA         YLVTNGKHGKKVNNVWNGMIGEVVYQRAVMAVGSLTINEERSEVVDFSVPFV
             530       540       550       560       570       580

┌────── TMI ──────
              50        60                    │70        80
At-iGluR     DIGIGILTVKKKSQ-GMWTFFDPFEKS      │LW-LASGAFFVLTGIVVWLVE--
             :||::::  ::::  : :|::|| ||:|     │ ||          ||    |
NMDA         ETGISVMVSRSNGTVSPSAFLEPFSAS      │VWVMMPVMDLIVSAIAVFVFEYF
             590       600                    │610       620       │630
                                              └────────────────────┘
                                           ┌──── TMII ──↓
              90        100                │110       120
At-iGluR     RPV--NPEF---QGSWGQQLS          │MMLLVWILLPLQLLTG      EKLQK---MSSRF┐
             :|| |:::   :::  |: ::          │|||       |           :|:     :|::│
NMDA         SPVGYNRNLAKGKAPHGPSFT          │IGKAIWLLWGLVFNNS      VPVQNPKGTTSKI│
             640       650                  │660       670             680     │
                                            └─────────────────┘                │
         ┌──── TMIII ─────────                                                  │
         │     140       150       160       170       180
At-iGluR │LVIVWVFVVLILTSSYSANLTSTKTISRMQLNHQMVFGGSTTSMTAKLGSINGG
         │:| ||| |  | |||::   : ::  :|:   :|  ::::  ::   : :
NMDA     │MVSVWAFFAVIFLASYTANLAA--FMIQEEFVDQV--TGLSDKKFQRPHDYSPP
         │690       700       710       720       730
         └──────────────

190       200       210       220
At-iGluR     GGLCTTLRDGTLTHVINEIPYLSILIGNYPNDFVMTDRVTNTNGF
             : |:  :::|  ::  |: ||:   :::: ::  | ::  |: ::|
NMDA         FRFGTVPNGSTERNIRNNYPYMHQYMTKFNQKGVEDALVSLKTGK
             740       760       770       780

TMIII
              230       240       250       260
At-iGluR     --GFMFQKGSDLVPKVSREIA-KLRSLGMLKDMEEK
             :|::: ::  |  |::|:  : ||  ::|
NMDA         LDAFIYD-AAVLNYKAGRDEGCKLVTIGSGYIFATTGYGIALQKGSPWK
             790       800       810       820

10        20        30↓
At-iGluR              RGNNDNLAYLLSTQRDKYDAAVGDITITSNRSLYVDFT
                      :| | ||: :|||  |: ::||:
KA           SYEIRLVEDGKYGAQDDKGQWNGMVKELIDHKADLAVADLTITHVREKAIDFS
             450       460       470       480       490       500
```

FIG.7A(1)

```
                40         50         60         70         ┌─── TMI ────
At-iGluR   LPYTDIGIGILTVKKK--SQGMWTFFDPFESSL│WL--------ASGAFF
           |: ::|::||   |  : :::::::|:::|::  ::||:       :|:::
KA         KPFMTLGVSILYRKPNGTNPSVFSFLNPLSPDI│WMYVLLAYLGVSCVLF
                510        520        530        540        550

┌── TMII ──┐↓
           80         90        100       110        120
At-iGluR   VLTGIVV--WLVE│RPVNPEFQGSWGQQLS│MMLLVWILLPLCLLTG│EKL--Q
            :   |   | ||:  :  :::::|::  |::  :  :  ::|  :
KA         VIARFSPYEWYDA│HPCNPGSEVV-ENNFT│LLNSFWFGMGSLMQQG│SELMPK
                560        570         580        590        600

┌──── TMIII ─────┐
              130        140       150       160       170
At-iGluR   KMSS│RFLVIVWVFVVLILTSSYSA│NLTSTKTISRMQLNHQMVFGGSTTSMT
            :|:|::  :|  ::||::|||:|||::  |:::||:   :  ::  ::   :
KA         ALST│RIIGGIWWFFTLIIISSYTA│NLAAFLTVERMESPIDSA-DDLAKQTK
                610        620        630        640        650

180       190       200        210       220
At-iGluR   AKLGSINGGGGLCTTLRDGTLTHVINEIPYLSILIGNYPNDFVMTDRVTNT
            : |::::|:::  |  :::::::   :  :::|  : :  ::   :  ||
KA         IEYGAVKDGATH-TFFKKSKISTFEKMWAFMSSKPSALVKNNEEGIQRTLT
                660        670        680        690        700

230       240       250       260
At-iGluR   NGFGFMFQKGS-DLVPKVSREIAKLRSLGMLKDMEEK
           :::::::::::  : :::  : :::::   :|
KA         ADYALLMESTTIEYITQRNCNLTQIGGLIDSKGYGIGTPMGSPYR
                710        720        730        740
```

FIG. 7A(II)

```
                       *      *              **   *
              520        530        540        550        560        570
Mgr7_R       GKGVREIPSSVCTLPCKPGQRKKTQKGTPCCWTCEP-CDGYQYQFDEMTCQHCPYDQRPN
                                               ||  ::  |:  :|::::|:    ||  |:   |  :
ARABIDOPSIS                                  TFXCWLKNAFCASSFFQLSSME----PYRLRLR
                                               10         20

580        590        600        610        620        630
Mgr7_R       ENRTGCQNIPIIKLEWHSPWAVIPVFLAMLGIIATIFVMATFIRYNDTPIVRASGRELSY
              :  :  |:|   |-  : :|  :  :|| :: :|| ::: | :  :| :  :|
ARABIDOPSIS  FSFQKC-SIAAF-LGPAVSFNSIERFLNSLS-TSLIFVXFSSMYF--LSXTCSSSIIFSV
              30         40         50         60         70         80

640        650        660        670        680        690
Mgr7_R       VLLTGIFLCYIITFLMIAKPDVAVCSFRRVFLGLMCISYAALLTKTNRIYRIFEQGKKS
              ::|| ||       ||
ARABIDOPSIS  XVITGAFLARPSAPISAFSFGSDAIISFSLK
              90         100        110
```

FIG. 7B

EST# ATT50711

```
  1  TGAAGATGCA GGACAGGTTC AATGGAGGTA TGATAACCCT CCAGACTTCA
 51  ATAGTGTGAA CCAGCTCTTT GAAGAAGGCC AGACTAAGGT GTGGCCAGAA
101  GGTTCGTTAG AAGAGACAGT GCAAAACGCG ATCAAGTCAT GGGAGATGGA
151  GTTCTCACAT AAGATCCGTT TACAGGACTT CAAGACTATA AACCCTGAGA
201  AGTTTAAGCT CTTTTGTCAA TGGGAGAGAA GGTTT
```

EST# ATT52655

```
  1  GGTGAATCTT TCGAGGTTGA GGAGGCGGTG GCTCTCGAGT CACAAACCAT
 51  AGCGCATATG GTTGAAGACG ACTGCGTNAN CAACGGAGTC CCTCTTCCTA
101  ACGTCACGAG CAAGATCCTN GCCAAGGTGA TCGAGTATTG CAAGAGGCAC
151  GTCGAGGCTG CTGCCTNTAA AGGCCGA
```

EST# T20773

```
  1  TCGTTTGCTC GAAGATCCGC TGCTTGATCT GCTCGCCACA CGCTATNGGA
 51  GAGGNAANGG TTAGGGTTAC TNATTTTCCG TCGAGTAGTC TNACNNAAAA
101  CTGCAACGGC TTACAACTTT GATCCGCCAT CGATTTTCGA TTCTAAAGCT
151  TGGACGAAGN AGAAGNANAA AGTTCGATTC GATTTCTGGA GAGAAATTGG
201  GGGAAAGTTT AAAAACGGAT CCCTAAGGTA GTCTGAGTCT CTCTCTC
```

FIG. 7C

| LANES | TREATMENTS | AVERAGE FOLD INDUCTION OF ASN1 RELATIVE TO CONTROL (LANE 3) |
|---|---|---|
| 4 | +0.3 mM KAINATE | 1.82 +/- 0.05 |
| 5 | +0.03 mM KAINATE | 1.97 +/- 0.02 |
| 6 | +0.05% GLUTAMATE | 2.46 +/- 0.40 |

```
     ATGGAGATTCTGTTTTCTATTTCCATTCTTGCTCTTCTCTTTTCCGGAGTAGTAGCTGCT
 34  ------+---------+---------+---------+---------+---------+---  93
     TACCTCTAAGACAAAAGATAAAGGTAAGAACGAGAAGAGAAAAGGCCTCATCATCGACGA

M  E  I  L  F  S  I  S  I  L  A  L  L  F  S  G  V  V  A  A   -

CCAAGCGACGATGATGTTTTCGAAGAGGTTAGGGTTGGATTGGTGGTTGACTTGAGTTCT
 94  ------+---------+---------+---------+---------+---------+--- 153
     GGTTCGCTGCTACTACAAAAGCTTCTCCAATCCCAACCTAACCACCAACTGAACTCAAGA

P  S  D  D  D  V  F  E  E  V  R  V  G  L  V  V  D  L  S  S   -

ATTCAAGGCAAGATTCTGGAAACTTCTTTTAACTTAGCGCTTTCAGATTTCTATGGCATC
154  ------+---------+---------+---------+---------+---------+--- 213
     TAAGTTCCGTTCTAAGACCTTTGAAGAAAATTGAATCGCGAAAGTCTAAAGATACCGTAG

I  Q  G  K  I  L  E  T  S  F  N  L  A  L  S  D  F  Y  G  I   -

AACAATGGATACCGAACCAGAGTCTCTGTTTTGGTCAGAGACTCCCAAGGAGACCCGATC
214  ------+---------+---------+---------+---------+---------+--- 273
     TTGTTACCTATGGCTTGGTCTCAGAGACAAAACCAGTCTCTGAGGGTTCCTCTGGGCTAG

N  N  G  Y  R  T  R  V  S  V  L  V  R  D  S  Q  G  D  P  I   -

ATTGCTCTTGCCGCCGCTACTGATCTTCTCAAAAATGCAAAAGCGGAAGCCATTGTTGGT
274  ------+---------+---------+---------+---------+---------+--- 333
     TAACGAGAACGGCGGCGATGACTAGAAGAGTTTTTACGTTTTCGCCTTCGGTAACAACCA

I  A  L  A  A  A  T  D  L  L  K  N  A  K  A  E  A  I  V  G   -

GCACAATCATTACAAGAGGCAAAGCTTTTGGCGACGATTAGCGAAAAAGCTAAAGTTCCG
334  ------+---------+---------+---------+---------+---------+--- 393
     CGTGTTAGTAATGTTCTCCGTTTCGAAAACCGCTGCTAATCGCTTTTTCGATTTCAAGGC

A  Q  S  L  Q  E  A  K  L  L  A  T  I  S  E  K  A  K  V  P   -

GTCATATCTACTTTCTTGCCAAACACGTTATCTTTGAAGAAATACGATAACTTTATTCAA
394  ------+---------+---------+---------+---------+---------+--- 453
     CAGTATAGATGAAAGAACGGTTTGTGCAATAGAAACTTCTTTATGCTATTGAAATAAGTT

V  I  S  T  F  L  P  N  T  L  S  L  K  K  Y  D  N  F  I  Q   -
```

FIG. 15A

```
     TGGACGCATGATACTACATCAGAGGCTAAGGGAATTACAAGTCTCATACAAGATTTCAGT
454  -----+----------+----------+----------+----------+----------+---  513
     ACCTGCGTACTATGATGTAGTCTCCGATTCCCTTAATGTTCAGAGTATGTTCTAAAGTCA

W  T  H  D  T  T  S  E  A  K  G  I  T  S  L  I  Q  D  F  S  -

TGTAAATCGGTTGTGGTTATATACGAGGATGCTGATGATTGGAGTGAGAGTTTGCAAATA
514  -----+----------+----------+----------+----------+----------+---  573
     ACATTTAGCCAACACCAATATATGCTCCTACGACTACTAACCTCACTCTCAAACGTTTAT

C  K  S  V  V  V  I  Y  E  D  A  D  D  W  S  E  S  L  Q  I  -

TTGGTTGAGAATTTTCAAGATAAAGGAATCTATATCGCTCGTTCTGCTTCTTTTGCAGTC
574  -----+----------+----------+----------+----------+----------+---  633
     AACCAACTCTTAAAAGTTCTATTTCCTTAGATATAGCGAGCAAGACGAAGAAAACGTCAG

L  V  E  N  F  Q  D  K  G  I  Y  I  A  R  S  A  S  F  A  V  -

TCATCATCAGGAGAAAATCATATGATGAATCAGCTAAGGAAGCTTAAGGTCTCAAGAGCA
634  -----+----------+----------+----------+----------+----------+---  693
     AGTAGTAGTCCTCTTTTAGTATACTACTTAGTCGATTCCTTCGAATTCCAGAGTTCTCGT

S  S  S  G  E  N  H  M  M  N  Q  L  R  K  L  K  V  S  R  A  -

TCGGTTTTTGTGGTGCATATGTCCGAGATTCTTGTTTCTCGTCTCTTCCAATGTGTAGAG
694  -----+----------+----------+----------+----------+----------+---  753
     AGCCAAAAACACCACGTATACAGGCTCTAAGAACAAAGAGCAGAGAAGGTTACACATCTC

S  V  F  V  V  H  M  S  E  I  L  V  S  R  L  F  Q  C  V  E  -

AAGTTAGGTTTGATGGAAGAAGCGTTCGCTTGGATCCTCACTGCAAGAACCATGAACTAC
754  -----+----------+----------+----------+----------+----------+---  813
     TTCAATCCAAACTACCTTCTTCGCAAGCGAACCTAGGAGTGACGTTCTTGGTACTTGATG

K  L  G  L  M  E  E  A  F  A  W  I  L  T  A  R  T  M  N  Y  -

TTGGAACATTTTGCAATAACTAGGTCGATGCAAGGGGTCATTGGTTTCAAATCTTACATC
814  -----+----------+----------+----------+----------+----------+---  873
     AACCTTGTAAAACGTTATTGATCCAGCTACGTTCCCCAGTAACCAAAGTTTAGAATGTAG

L  E  H  F  A  I  T  R  S  M  Q  G  V  I  G  F  K  S  Y  I  -
```

FIG. 15B

```
         CCTGTATCTGAAGAAGTTAAGAATTTTACTTCAAGATTGAGGAAACGTATGGGAGATGAT
874      -----+----------+----------+----------+----------+---------+---  933
         GGACATAGACTTCTTCAATTCTTAAAATGAAGTTCTAACTCCTTTGCATACCCTCTACTA

P  V  S  E  E  V  K  N  F  T  S  R  L  R  K  R  M  G  D  D   -

ACAGAAACAGAGCATTCTAGTGTAATCATCGGTTTACGCGCACACGATATCGCTTGTATT
934      -----+----------+----------+----------+----------+---------+---  993
         TGTCTTTGTCTCGTAAGATCACATTAGTAGCCAAATGCGCGTGTGCTATAGCGAACATAA

T  E  T  E  H  S  S  V  I  I  G  L  R  A  H  D  I  A  C  I   -

CTAGCAAATGCAGTAGAGAAGTTCAGTGTAAGTGGTAAAGTTGAAGCATCTTCGAATGTA
994      -----+----------+----------+----------+----------+---------+--- 1053
         GATCGTTTACGTCATCTCTTCAAGTCACATTCACCATTTCAACTTCGTAGAAGCTTACAT

L  A  N  A  V  E  K  F  S  V  S  G  K  V  E  A  S  S  N  V   -

TCAGCTGATCTTCTGGATACAATTAGACATAGTAGATTCAAGGGTTTGAGTGGTGACATC
1054     -----+----------+----------+----------+----------+---------+--- 1113
         AGTCGACTAGAAGACCTATGTTAATCTGTATCATCTAAGTTCCCAAACTCACCACTGTAG

S  A  D  L  L  D  T  I  R  H  S  R  F  K  G  L  S  G  D  I   -

CAAATCTCTGACAACAAATTTATCTCAGAGACATTTGAAATCGTGAATATTGGaagagaa
1114     ----+-----------+----------+----------+----------+---------+--- 1173
         GTTTAGAGACTGTTGTTTAAATAGAGTCTCTGTAAACTTTAGCACTTATTACCttctctt

Q  I  S  D  N  K  F  I  S  E  T  F  E  I  V  N  I  G  R  E   - aaacagagaaggataggatTatggagtggtggtagtTTTaGCcaaagaagacagattgtt
1174     ----+-----------+----------+----------+----------+---------+--- 1233
         tttgtctcttcctatcctaAtacctcaccaccatcaAAAtCGgtttcttctgtctaacaa

K  Q  R  R  I  G  L  W  S  G  G  S  F  S  Q  R  R  Q  I  V   - tggcctggcaggtctcgtaagatcccaagacaccgtgttttggcagagaAaggtgAaaaG
1234     ----+-----------+----------+----------+----------+---------+--- 1293
         accggaccgtccagagcattctaggggttctgtggcacaaaaccgtctctTtccacTtttC

W  P  G  R  S  R  K  I  P  R  H  R  V  L  A  E  K  G  E  K   -
```

FIG. 15C

```
     AAGGTGCTTAGGGTCTTAGTTACCGCAGGAAACAAgGTCCCGCATCTAGTGTCGGTGCGT
1294 ----+-----------+----------+----------+-----------+--------+---  1353
     TTCCACGAATCCCAGAATCAATGGCGTCCTTTGTTcCAGGGCGTAGATCACAGCCACGCA

K  V  L  R  V  L  V  T  A  G  N  K  V  P  H  L  V  S  V  R   -

CCTGATCCTGAAACAGGTGTTAATACTGTCTCTGGATTCTGCGTAGAGGTTTTCAAGACT
1354 ----+-----------+----------+----------+-----------+--------+---  1413
     GGACTAGGACTTTGTCCACAATTATGACAGAGACCTAAGACGCATCTCCAAAAGTTCTGA

P  D  P  E  T  G  V  N  T  V  S  G  F  C  V  E  V  F  K  T   -

TGCATTGCTCCTTTTAACTACGAGCTTGAATTCATACCTTACCGTGGAAACAATGACAAT
1414 ----+-----------+----------+----------+-----------+--------+---  1473
     ACGTAACGAGGAAAATTGATGCTCGAACTTAAGTATGGAATGGCACCTTTGTTACTGTTA

C  I  A  P  F  N  Y  E  L  E  F  I  P  Y  R  G  N  N  D  N   -

CTTGCTTATCTACTTTCTACTCAGAGAGACAAGTATGATGCAGCAGTTGGTGATATCACC
1474 ----+-----------+----------+----------+-----------+--------+---  1533
     GAACGAATAGATGAAAGATGAGTCTCTCTGTTCATACTACGTCGTCAACCACTATAGTGG

L  A  Y  L  L  S  T  Q  R  D  K  Y  D  A  A  V  G  D  I  T   -

ATCACTTCCAACAGATCTTTGTATGTTGATTTTACTTTGCCGTACACTGACATTGGTATT
1534 ----+-----------+----------+----------+-----------+--------+---  1593
     TAGTGAAGGTTGTCTAGAAACATACAACTAAAATGAAACGGCATGTGACTGTAACCATAA

I  T  S  N  R  S  L  Y  V  D  F  T  L  P  Y  T  D  I  G  I   -

GGAATCCTGACAGTAAAAAAGAAAAGCCAAGGGATGTGGACTTTCTTTGATCCTTTTGAA
1594 ----+-----------+----------+----------+-----------+--------+---  1653
     CCTTAGGACTGTCATTTTTTCTTTTCGGTTCCCTACACCTGAAAGAAACTAGGAAAACTT

G  I  L  T  V  K  K  K  S  Q  G  M  W  T  F  F  D  P  F  E   -

AAATCCTTGTGGCTAGCaAGTGGAGCTTTCTTtGTCTTaACtGGGATTGTTGTTTGGTTa
1654 ----+-----------+----------+----------+-----------+--------+---  1713
     TTTAGGAACACCGATCGtTCACCTCGAAAGAAaCAGAAtTGaCCCTAACAACAAACCAAt

K  S  L  W  L  A  S  G  A  F  F  V  L  T  G  I  V  V  W  L   -
```

FIG. 15D

```
      GTTGAACGGtCCGTTAATCCGGAaTTTCAgGGCTCTTGGGGACAACAACTTAGTATGATG
1714  ----+-----------+----------+----------+----------+--------+--- 1773
      CAACTTGCCaGGCAATTAGGCCTtAAAGTcCCGAGAACCCCTGTTGTTGAATCATACTAC

V  E  R  S  V  N  P  E  F  Q  G  S  W  G  Q  Q  L  S  M  M  -

CTCTGGTTTGGtTTCTCaACCATTGTaTTTGCTCACAGaGAGAAGCTACAGAAAATGTCA
1774  ----+-----------+----------+----------+----------+--------+--- 1833
      GAGACCAAACCaAAGAGtTGGTAACAtAAACGAGTGTCtCTCTTCGATGTCTTTTACAGT

L  W  F  G  F  S  T  I  V  F  A  H  R  E  K  L  Q  K  M  S  -

TCAAGATTCTTAGTCATAGTTTGGGTTTTTGTGGTGTTAATATTGACTTCAAGTTACAGC
1834  ----+-----------+----------+----------+----------+--------+--- 1893
      AGTTCTAAGAATCAGTATCAAACCCAAAAACACCACAATTATAACTGAAGTTCAATGTCG

S  R  F  L  V  I  V  W  V  F  V  V  L  I  L  T  S  S  Y  S  -

GCAAACTTGACATCAACCAAGACCATTTCTCGCATGCAATTAAATCATCAGATGGTTTTC
1894  ----+-----------+----------+----------+----------+--------+--- 1953
      CGTTTGAACTGTAGTTGGTTCTGGTAAAGAGCGTACGTTAATTTAGTAGTCTACCAAAAG

A  N  L  T  S  K  T  I  S  R  M  Q  L  N  H  Q  M  V  F  -

GGGGGATCTACGACGTCAATGACTGCGAAGCTCGGATCCATTAATGcAGtTGAGGCCTAT
1954  ----+-----------+----------+----------+----------+--------+--- 2013
      CCCCCTAGATGCTGCAGTTACTGACGCTTCGAGCCTAGGTAATTAGgTcAACTCCGGATA

G  G  S  T  T  S  M  T  A  K  L  G  S  I  N  A  V  E  A  Y  -

GCACAACTTTtGCGAGATGGAACTCTTAaTCATGTCATCAATGAAATACCTTATCTCAGT
2014  ----+-----------+----------+----------+----------+--------+--- 2073
      CGTGTTGAAAaCGCTCTACCTTGAGAATtAGTACAGTAGTTACTTTATGGAATAGAGTCA

A  Q  L  L  R  D  G  T  L  N  H  V  I  N  E  I  P  Y  L  S  -

ATCCTTATCGGAAATTATCCGAATGATTTCGTAATGACAGATAGAGTGACTAATACCAAT
2074  ----+-----------+----------+----------+----------+--------+--- 2133
      TAGGAATAGCCTTTAATAGGCTTACTAAAGCATTACTGTGTATCTCACTGATTATGGTTA

I  L  I  G  N  Y  P  N  D  F  V  M  T  D  R  V  T  N  T  N  -
```

FIG. 15E

```
             GGCTTTGGCTTTATGTTCCAGAAAGGTTCGGATTTGGTTCCTAAAGTATCGCGAGAAATC
       2134  ----+-----------+----------+----------+----------+----------+---  2193
             CCGAAACCGAAATACAAGGTCTTTCCAAGCCTAAACCAAGGATTTCATAGCGCTCTTTAG

G  F  G  F  M  F  Q  K  G  S  D  L  V  P  K  V  S  R  E  I   -

GCGAAGCTAAGaTCATTgGGAATGTTGAAAGACATGGAGAAAAAATGGTTTCAAAAaCTG
       2194  ----+-----------+----------+----------+----------+----------+---  2253
             CGCTTCGATTCtAGTAAcCCTTACAACTTTCTGTACCTCTTTTTTACCAAAGTTTTtGAC

A  K  L  R  S  L  G  M  L  K  D  M  E  K  K  W  F  Q  K  L   -

GATTCACTAAATGTACATTCCAACACcGAGGAAGTTGCaTCTACCAACGACGATGATGAG
       2254  ----+-----------+----------+----------+----------+----------+---  2313
             CTAAGTGATTTACATGTAAGGTTGTGgCTCCTTCAACGtAGATGGTTGCTGCTACTACTC

D  S  L  N  V  H  S  N  T  E  E  V  A  S  T  N  D  D  D  E   -

GCATCTAAGCGATTCACCTTCCGTGAGTTGCGCGGTTTGTTCATCATTGCGGGAGCTGCT
       2314  ----+-----------+----------+----------+----------+----------+---  2373
             CGTAGATTCGCTAAGTGGAAGGCACTCAACGCGCCAAACAAGTAGTAACGCCCTCGACGA

A  S  K  R  F  T  F  R  E  L  R  G  L  F  I  I  A  G  A  A   -

CATGTTCTCGTACTAGCCCTACATCTCTTTCATACGCGTCAAGAGGTATCACGACTATGC
       2374  ----+-----------+----------+----------+----------+----------+---  2433
             GTACAAGAGCATGATCGGGATGTAGAGAAAGTATGCGCAGTTCTCCATAGTGCTGATACG

H  V  L  V  L  A  L  H  L  F  H  T  R  Q  E  V  S  R  L  C   -

ACCAAACTTCAAAGCTTCTATAAGTAAAAAGTGATCCATCgTTCATAAGCTCTACTATAG
       2434  ----+-----------+----------+----------+----------+----------+---  2493
             TGGTTTGAAGTTTCGAAGATATTCATTTTTCACTAGGTAGcAAGTATTCGAGATGATATC

T  K  L  Q  S  F  Y  K  *  K  V  I  H  R  S  *  A  L  L  *   -

CAATTGAcGGgacAGGACTCATAA
       2494  ----+-----------+-------  2517
             GTTAACTgCCctgTCCTGAGTATT

Q  L  T  G  Q  D  *   -
```

FIG. 15F

WILD TYPE

WILD TYPE

NO DNQX

Col
(WILD TYPE)

+0.1mM DNQX

Col
(WILD TYPE)

NO DNQX

DNQX
SUPER-SENSITIVE
MUTANT

+0.1mM DNQX

DNQX
SUPER-SENSITIVE
MUTANT

KA RESISTANT MUTANT

WILD TYPE

KA RESISTANT GIANT

SEQUENCE LISTING (1) GENERAL INFORMATION:

(iii) NUMBER OF SEQUENCES: 36

(2) INFORMATION FOR SEQ ID NO: 1:

(i) SEQUENCE CHARACTERISTICS:
        (A) LENGTH: 41 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 1:

Gln Arg Asp Lys Tyr Asp Ala Ala Val Gly Asp Ile Thr Ile Thr Ser
1               5                   10                  15

Asn Arg Ser Leu Tyr Val Asp Phe Thr Leu Pro Tyr Thr Asp Ile Gly
                20                  25                  30

Ile Gly Ile Leu Thr Val Lys Lys Lys
            35                  40

(2) INFORMATION FOR SEQ ID NO: 2:

(i) SEQUENCE CHARACTERISTICS:
        (A) LENGTH: 41 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 2:

Gln Thr Lys Asn Val Asp Leu Ala Leu Ala Gly Ile Thr Ile Thr Asp
1               5                   10                  15

Glu Arg Lys Lys Ala Ile Asp Phe Ser Asp Gly Tyr Tyr Lys Ser Gly
                20                  25                  30

Leu Leu Val Met Val Lys Ala Asn Asn
            35                  40

(2) INFORMATION FOR SEQ ID NO: 3:

(i) SEQUENCE CHARACTERISTICS:
        (A) LENGTH: 41 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 3:

Leu Arg Gln Glu Ala Asp Ile Ala Val Ala Pro Leu Thr Val Thr Ser
1               5                   10                  15

Ala Arg Glu Glu Val Val Ser Phe Thr Thr Pro Phe Leu Gln Thr Gly
                20                  25                  30

Ile Gly Ile Leu Leu Arg Lys Glu Thr
            35                  40

(2) INFORMATION FOR SEQ ID NO: 4:

(i) SEQUENCE CHARACTERISTICS:
        (A) LENGTH: 41 amino acids
        (B) TYPE: amino acid (C) STRANDEDNESS: <Unknown>
                (D) TOPOLOGY: unknown (ii) MOLECULE TYPE: peptide (xi) SEQUENCE DESCRIPTION: SEQ ID NO: 4:

Ile Arg Lys Glu Ala Asp Leu Ala Ile Ala Pro Leu Thr Ile Thr Ser
1               5                   10                  15

Val Arg Glu Asn Ala Ile Ser Phe Thr Lys Pro Phe Met Gln Thr Gly
            20                  25                  30

Ile Gly Ile Leu Leu Lys Lys Asp Thr
            35                  40

(2) INFORMATION FOR SEQ ID NO: 5:

(i) SEQUENCE CHARACTERISTICS:
                (A) LENGTH: 41 amino acids
                (B) TYPE: amino acid
                (C) STRANDEDNESS: <Unknown>
                (D) TOPOLOGY: unknown (ii) MOLECULE TYPE: peptide (xi) SEQUENCE DESCRIPTION: SEQ ID NO: 5:

Val Tyr Gly Arg Ala Asp Val Ala Val Ala Pro Leu Thr Ile Thr Leu
1               5                   10                  15

Val Arg Glu Glu Val Ile Asp Phe Ser Lys Pro Phe Met Ser Leu Gly
            20                  25                  30

Ile Ser Ile Met Ile Lys Lys Pro Gln
            35                  40

(2) INFORMATION FOR SEQ ID NO: 6:

(i) SEQUENCE CHARACTERISTICS:
                (A) LENGTH: 41 amino acids
                (B) TYPE: amino acid
                (C) STRANDEDNESS: <Unknown>
                (D) TOPOLOGY: unknown (ii) MOLECULE TYPE: peptide (xi) SEQUENCE DESCRIPTION: SEQ ID NO: 6:

Val Tyr Gly Arg Ala Asp Ile Ala Val Ala Pro Leu Thr Ile Thr Leu
1               5                   10                  15

Val Arg Glu Glu Val Ile Asp Phe Ser Lys Pro Phe Met Ser Leu Gly
            20                  25                  30

Ile Ser Ile Met Ile Lys Lys Pro Gln
            35                  40

(2) INFORMATION FOR SEQ ID NO: 7:

(i) SEQUENCE CHARACTERISTICS:
                (A) LENGTH: 41 amino acids
                (B) TYPE: amino acid
                (C) STRANDEDNESS: <Unknown>
                (D) TOPOLOGY: unknown (ii) MOLECULE TYPE: peptide (xi) SEQUENCE DESCRIPTION: SEQ ID NO: 7:

Val Tyr Gly Lys Ala Asp Ile Ala Ile Ala Pro Leu Thr Ile Thr Leu
1               5                   10                  15

Val Arg Glu Glu Val Ile Asp Phe Ser Lys Pro Phe Met Ser Leu Gly
            20                  25                  30

```
Ile Ser Ile Met Ile Lys Lys Pro Gln
        35              40
```

(2) INFORMATION FOR SEQ ID NO: 8:

(i) SEQUENCE CHARACTERISTICS:
        (A) LENGTH: 262 amino acids
        (B) TYPE: amino acid
        (C) STRANDEDNESS: <Unknown>
        (D) TOPOLOGY: unknown (ii) MOLECULE TYPE: protein (xi) SEQUENCE DESCRIPTION: SEQ ID NO: 8:

```
Arg Gly Asn Asn Asp Asn Leu Ala Tyr Leu Leu Ser Thr Gln Arg Asp
1               5                   10                  15

Lys Tyr Asp Ala Ala Val Gly Asp Ile Thr Ile Thr Ser Asn Arg Ser
            20                  25                  30

Leu Tyr Val Asp Phe Thr Leu Pro Tyr Thr Asp Ile Gly Ile Gly Ile
        35                  40                  45

Leu Thr Val Lys Lys Lys Ser Gln Gly Met Trp Thr Phe Phe Asp Pro
    50                  55                  60

Phe Glu Lys Ser Leu Trp Leu Ala Ser Gly Ala Phe Phe Val Leu Thr
65                  70                  75                  80

Gly Ile Val Val Trp Leu Val Glu Arg Pro Val Asn Pro Glu Phe Gln
                85                  90                  95

Gly Ser Trp Gly Gln Gln Leu Ser Met Met Leu Leu Val Trp Ile Leu
            100                 105                 110

Leu Pro Leu Cys Leu Leu Thr Gly Glu Lys Leu Gln Lys Met Ser Ser
        115                 120                 125

Arg Phe Leu Val Ile Val Trp Val Phe Val Val Leu Ile Leu Thr Ser
    130                 135                 140

Ser Tyr Ser Ala Asn Leu Thr Ser Thr Lys Thr Ile Ser Arg Met Gln
145                 150                 155                 160

Leu Asn His Gln Met Val Phe Gly Gly Ser Thr Thr Ser Met Thr Ala
                165                 170                 175

Lys Leu Gly Ser Ile Asn Gly Gly Gly Leu Cys Thr Thr Leu Arg
            180                 185                 190

Asp Gly Thr Leu Thr His Val Ile Asn Glu Ile Pro Tyr Leu Ser Ile
        195                 200                 205

Leu Ile Gly Asn Tyr Pro Asn Asp Phe Val Met Thr Asp Arg Val Thr
    210                 215                 220

Asn Thr Asn Gly Phe Gly Phe Met Phe Gln Lys Gly Ser Asp Leu Val
225                 230                 235                 240

Pro Lys Val Ser Arg Glu Ile Ala Lys Leu Arg Ser Leu Gly Met Leu
                245                 250                 255

Lys Asp Met Glu Glu Lys
            260
```

(2) INFORMATION FOR SEQ ID NO: 9:

(i) SEQUENCE CHARACTERISTICS:
        (A) LENGTH: 295 amino acids
        (B) TYPE: amino acid
        (C) STRANDEDNESS: <Unknown>
        (D) TOPOLOGY: unknown (ii) MOLECULE TYPE: protein (xi) SEQUENCE DESCRIPTION: SEQ ID NO: 9:

```
Tyr Leu Val Thr Asn Gly Lys His Gly Lys Lys Val Asn Asn Val Trp
 1               5                  10                  15

Asn Gly Met Ile Gly Glu Val Val Tyr Gln Arg Ala Val Met Ala Val
                20                  25                  30

Gly Ser Leu Thr Ile Asn Glu Glu Arg Ser Glu Val Val Asp Phe Ser
            35                  40                  45

Val Pro Phe Val Glu Thr Gly Ile Ser Val Met Val Ser Arg Ser Asn
    50                  55                  60

Gly Thr Val Ser Pro Ser Ala Phe Leu Glu Pro Phe Ser Ala Ser Val
65                  70                  75                  80

Trp Val Met Met Phe Val Met Leu Leu Ile Val Ser Ala Ile Ala Val
                85                  90                  95

Phe Val Phe Glu Tyr Phe Ser Pro Val Gly Tyr Asn Arg Asn Leu Ala
                100                 105                 110

Lys Gly Lys Ala Pro His Gly Pro Ser Phe Thr Ile Gly Lys Ala Ile
            115                 120                 125

Trp Leu Leu Trp Gly Leu Val Phe Asn Asn Ser Val Pro Val Gln Asn
130                 135                 140

Pro Lys Gly Thr Thr Ser Lys Ile Met Val Ser Val Trp Ala Phe Phe
145                 150                 155                 160

Ala Val Ile Phe Leu Ala Ser Tyr Thr Ala Asn Leu Ala Ala Phe Met
                165                 170                 175

Ile Gln Glu Glu Phe Val Asp Gln Val Thr Gly Leu Ser Asp Lys Lys
            180                 185                 190

Phe Gln Arg Pro His Asp Tyr Ser Pro Pro Phe Arg Phe Gly Thr Val
            195                 200                 205

Pro Asn Gly Ser Thr Glu Arg Asn Ile Arg Asn Asn Tyr Pro Tyr Met
210                 215                 220

His Gln Tyr Met Thr Lys Phe Asn Gln Lys Gly Val Glu Asp Ala Leu
225                 230                 235                 240

Val Ser Leu Lys Thr Gly Lys Leu Asp Ala Phe Ile Tyr Asp Ala Ala
                245                 250                 255

Val Leu Asn Tyr Lys Ala Gly Arg Asp Glu Gly Cys Lys Leu Val Thr
            260                 265                 270

Ile Gly Ser Gly Tyr Ile Phe Ala Thr Thr Gly Tyr Gly Ile Ala Leu
            275                 280                 285

Gln Lys Gly Ser Pro Trp Lys
            290                 295

(2) INFORMATION FOR SEQ ID NO: 10:

(i) SEQUENCE CHARACTERISTICS:
        (A) LENGTH: 297 amino acids
        (B) TYPE: amino acid
        (C) STRANDEDNESS: <Unknown>
        (D) TOPOLOGY: unknown (ii) MOLECULE TYPE: protein (xi) SEQUENCE DESCRIPTION: SEQ ID NO: 10:

Ser Tyr Glu Ile Arg Leu Val Glu Asp Gly Lys Tyr Gly Ala Gln Asp
 1               5                  10                  15

Asp Lys Gly Gln Trp Asn Gly Met Val Lys Glu Leu Ile Asp His Lys
                20                  25                  30

Ala Asp Leu Ala Val Ala Pro Leu Thr Ile Thr His Val Arg Glu Lys
            35                  40                  45
```

```
Ala Ile Asp Phe Ser Lys Pro Phe Met Thr Leu Gly Val Ser Ile Leu
 50                  55                  60

Tyr Arg Lys Pro Asn Gly Thr Asn Pro Ser Val Phe Ser Phe Leu Asn
 65                  70                  75                  80

Pro Leu Ser Pro Asp Ile Trp Met Tyr Val Leu Leu Ala Tyr Leu Gly
                 85                  90                  95

Val Ser Cys Val Leu Phe Val Ile Ala Arg Phe Ser Pro Tyr Glu Trp
            100                 105                 110

Tyr Asp Ala His Pro Cys Asn Pro Gly Ser Glu Val Val Glu Asn Asn
            115                 120                 125

Phe Thr Leu Leu Asn Ser Phe Trp Phe Gly Met Gly Ser Leu Met Gln
            130                 135                 140

Gln Gly Ser Glu Leu Met Pro Lys Ala Leu Ser Thr Arg Ile Ile Gly
145                 150                 155                 160

Gly Ile Trp Trp Phe Phe Thr Leu Ile Ile Ile Ser Ser Tyr Thr Ala
                165                 170                 175

Asn Leu Ala Ala Phe Leu Thr Val Glu Arg Met Glu Ser Pro Ile Asp
            180                 185                 190

Ser Ala Asp Asp Leu Ala Lys Gln Thr Lys Ile Glu Tyr Gly Ala Val
            195                 200                 205

Lys Asp Gly Ala Thr Met Thr Phe Phe Lys Lys Ser Lys Ile Ser Thr
210                 215                 220

Phe Glu Lys Met Trp Ala Phe Met Ser Ser Lys Pro Ser Ala Leu Val
225                 230                 235                 240

Lys Asn Asn Glu Glu Gly Ile Gln Arg Thr Leu Thr Ala Asp Tyr Ala
                245                 250                 255

Leu Leu Met Glu Ser Thr Thr Ile Glu Tyr Ile Thr Gln Arg Asn Cys
            260                 265                 270

Asn Leu Thr Gln Ile Gly Gly Leu Ile Asp Ser Lys Gly Tyr Gly Ile
            275                 280                 285

Gly Thr Pro Met Gly Ser Pro Tyr Arg
290                 295
```

(2) INFORMATION FOR SEQ ID NO: 11:

(i) SEQUENCE CHARACTERISTICS:
        (A) LENGTH: 179 amino acids
        (B) TYPE: amino acid
        (C) STRANDEDNESS: <Unknown>
        (D) TOPOLOGY: unknown (ii) MOLECULE TYPE: protein (xi) SEQUENCE DESCRIPTION: SEQ ID NO: 11:

```
Gly Lys Gly Val Arg Glu Ile Pro Ser Ser Val Cys Thr Leu Pro Cys
 1               5                  10                  15

Lys Pro Gly Gln Arg Lys Lys Thr Gln Lys Gly Thr Pro Cys Cys Trp
            20                  25                  30

Thr Cys Glu Pro Cys Asp Gly Tyr Gln Tyr Gln Phe Asp Glu Met Thr
        35                  40                  45

Cys Gln His Cys Pro Tyr Asp Gln Arg Pro Asn Glu Asn Arg Thr Gly
 50                  55                  60

Cys Gln Asn Ile Pro Ile Ile Lys Leu Glu Trp His Ser Pro Trp Ala
 65                  70                  75                  80

Val Ile Pro Val Phe Leu Ala Met Leu Gly Ile Ile Ala Thr Ile Phe
                 85                  90                  95
```

Val Met Ala Thr Phe Ile Arg Tyr Asn Asp Thr Pro Ile Val Arg Ala
            100                 105                 110

Ser Gly Arg Glu Leu Ser Tyr Val Leu Leu Thr Gly Ile Phe Leu Cys
        115                 120                 125

Tyr Ile Ile Thr Phe Leu Met Ile Ala Lys Pro Asp Val Ala Val Cys
    130                 135                 140

Ser Phe Arg Arg Val Phe Leu Gly Leu Gly Met Cys Ile Ser Tyr Ala
145                 150                 155                 160

Ala Leu Leu Thr Lys Thr Asn Arg Ile Tyr Arg Ile Phe Glu Gln Gly
                165                 170                 175

Lys Lys Ser (2) INFORMATION FOR SEQ ID NO: 12:

(i) SEQUENCE CHARACTERISTICS:
        (A) LENGTH: 115 amino acids
        (B) TYPE: amino acid
        (C) STRANDEDNESS: <Unknown>
        (D) TOPOLOGY: unknown (ii) MOLECULE TYPE: peptide (xi) SEQUENCE DESCRIPTION: SEQ ID NO: 12:

Thr Phe Xaa Cys Trp Leu Lys Asn Ala Phe Cys Ala Ser Ser Phe Phe
1               5                   10                  15

Gln Leu Ser Ser Met Glu Pro Tyr Arg Leu Arg Leu Arg Phe Ser Phe
            20                  25                  30

Gln Lys Cys Ser Ile Ala Ala Phe Leu Gly Pro Ala Val Ser Phe Asn
        35                  40                  45

Ser Ile Glu Arg Phe Leu Asn Ser Leu Ser Thr Ser Leu Ile Phe Val
50                  55                  60

Xaa Phe Ser Ser Met Tyr Phe Leu Ser Xaa Thr Cys Ser Ser Ser Ile
65                  70                  75                  80

Ile Phe Ser Val Xaa Val Ile Thr Gly Ala Phe Leu Ala Arg Pro Ser
                85                  90                  95

Ala Pro Ile Ser Ala Phe Ser Phe Gly Ser Asp Ala Ile Ile Ser Phe
            100                 105                 110

Ser Leu Lys
        115

(2) INFORMATION FOR SEQ ID NO: 13:

(i) SEQUENCE CHARACTERISTICS:
        (A) LENGTH: 235 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO: 13:

TGAAGATGCA GGACAGGTTC AATGGAGGTA TGATAACCCT CCAGACTTCA ATAGTGTGAA    60

CCAGCTCTTT GAAGAAGGCC AGACTAAGGT GTGGCCAGAA GGTTCGTTAG AAGAGACAG    120

GCAAAACGCG ATCAAGTCAT GGGAGATGGA GTTCTCACAT AAGATCCGTT TACAGGACT    180

CAAGACTATA AACCCTGAGA AGTTTAAGCT CTTTTGTCAA TGGGAGAGAA GGTTT    235

(2) INFORMATION FOR SEQ ID NO: 14:

(i) SEQUENCE CHARACTERISTICS:
        (A) LENGTH: 177 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO: 14:

GGTGAATCTT TCGAGGTTGA GGAGGCGGTG GCTCTCGAGT CACAAACCAT AGCGCATATG      60

GTTGAAGACG ACTGCGTNAN CAACGGAGTC CCTCTTCCTA ACGTCACGAG CAAGATCCT     120

GCCAAGGTGA TCGAGTATTG CAAGAGGCAC GTCGAGGCTG CTGCCTNTAA AGGCCGA      177

(2) INFORMATION FOR SEQ ID NO: 15:

(i) SEQUENCE CHARACTERISTICS:
        (A) LENGTH: 247 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO: 15:

TCGTTTGCTC GAAGATCCGC TGCTTGATCT GCTCGCCACA CGCTATNGGA GAGGNAANGG      60

TTAGGGTTAC TNATTTTCCG TCGAGTAGTC TNACNNAAAA CTGCAACGGC TTACAACTT     120

GATCCGCCAT CGATTTTCGA TTCTAAAGCT TGGACGAAGN AGAAGNANAA AGTTCGATT     180

GATTTCTGGA GAGAAATTGG GGGAAAGTTT AAAAACGGAT CCCTAAGGTA GTCTGAGTC     240

CTCTCTC                                                              247

(2) INFORMATION FOR SEQ ID NO: 16:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 16:

Val Arg Pro Asp Pro Glu Thr Gly Val Asn Thr Val Ser Gly Phe Cys
1               5                   10                  15

Val Glu Val Phe Lys Thr Cys Ile Ala Pro Phe Asn Tyr
            20                  25

(2) INFORMATION FOR SEQ ID NO: 17:

(i) SEQUENCE CHARACTERISTICS:
        (A) LENGTH: 59 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 17:

Glu Leu Glu Phe Ile Pro Tyr Arg Gly Asn Asn Asp Asn Leu Ala Tyr
1               5                   10                  15

Leu Leu Ser Thr Gln Arg Asp Lys Tyr Asp Ala Ala Val Gly Asp Ile
            20                  25                  30

Thr Ile Thr Ser Asn Arg Ser Leu Tyr Val Asp Phe Thr Leu Pro Tyr
        35                  40                  45

```
Thr Asp Ile Gly Ile Gly Ile Leu Thr Val Lys
    50                  55
```

(2) INFORMATION FOR SEQ ID NO: 18:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 18:

```
Lys Lys Ser Gln Gly Met Trp Thr Phe Phe Asp Pro Phe Glu Lys Ser
1               5                   10                  15
Leu Trp Leu Ala Ser Gly Ala Phe Phe Val Leu Thr Gly Ile Val Val
            20                  25                  30
Trp Leu Val Glu Arg
            35
```

(2) INFORMATION FOR SEQ ID NO: 19:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 19:

```
Ser Val Asn Pro Glu Phe Gln Gly Ser Trp Gly Gln Gln Leu Ser Met
1               5                   10                  15
```

(2) INFORMATION FOR SEQ ID NO: 20:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 20:

```
Met Leu Trp Phe Gly Phe Ser Thr Ile Val Phe Ala His Arg Glu
1               5                   10                  15
```

(2) INFORMATION FOR SEQ ID NO: 21:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 21:

```
Lys Leu Gln Lys Met Ser Ser Arg Phe Leu Val Ile Val Trp Val Phe
1               5                   10                  15
Val Val Leu Ile Leu Thr Ser Ser Tyr Ser Ala Asn Leu Thr Ser Thr
            20                  25                  30
Lys Thr Ile Ser Arg Met
            35
```

(2) INFORMATION FOR SEQ ID NO: 22:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 22:

```
Gln Leu Asn His Gln
1               5
```

(2) INFORMATION FOR SEQ ID NO: 23:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 23:

```
Met Val Phe Gly Gly Ser Thr Thr Ser Met Thr Ala Lys Leu Gly Ser
1               5                   10                  15
Ile Asn Ala Val Glu Ala Tyr Ala Gln Leu Leu
            20                  25
```

(2) INFORMATION FOR SEQ ID NO: 24:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 24:

```
Arg Asp Gly Thr Leu Asn His Val Ile Asn Glu Ile Pro Tyr Leu Ser
1               5                   10                  15
Ile Leu Ile Gly Asn Tyr Pro Asn Asp Phe Val Met Thr Asp Arg Val
            20                  25                  30
Thr Asn Thr
        35
```

(2) INFORMATION FOR SEQ ID NO: 25:

(i) SEQUENCE CHARACTERISTICS:
        (A) LENGTH: 90 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 25:

```
Asn Gly Phe Gly Phe Met Phe Gln Lys Gly Ser Asp Leu Val Pro Lys
1               5                   10                  15
Val Ser Arg Glu Ile Ala Lys Leu Arg Ser Leu Gly Met Leu Lys Asp
            20                  25                  30
Met Glu Lys Lys Trp Phe Gln Lys Leu Asp Ser Leu Asn Val His Ser
        35                  40                  45
```

```
Asn Thr Glu Glu Val Ala Ser Thr Asn Asp Asp Glu Ala Ser Lys
    50                  55                  60

Arg Phe Thr Phe Arg Glu Leu Arg Gly Leu Phe Ile Ile Ala Gly Ala
65                  70                  75                  80

Ala His Val Leu Val Leu Ala Leu His Leu
                85                  90
```

(2) INFORMATION FOR SEQ ID NO: 26:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 26:

```
Phe His Thr Arg Gln Glu Val Ser Arg Leu
1               5                   10
```

(2) INFORMATION FOR SEQ ID NO: 27:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 27:

```
Cys Thr Lys Leu Gln Ser Phe Tyr Lys
1               5
```

(2) INFORMATION FOR SEQ ID NO: 28:

(i) SEQUENCE CHARACTERISTICS:
        (A) LENGTH: 41 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 28:

```
Ala Ala Glu Ile Ala Lys His Cys Gly Phe Lys Tyr Lys Leu Thr Ile
1                   5                   10                  15

Val Gly Asp Gly Lys Tyr Gly Ala Arg Asp Ala Asp Thr Lys Ile Trp
                20                  25                  30

Asn Gly Met Val Gly Glu Leu Val Tyr
            35                  40
```

(2) INFORMATION FOR SEQ ID NO: 29:

(i) SEQUENCE CHARACTERISTICS:
        (A) LENGTH: 39 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 29:

```
Gly Lys Ala Asp Ile Ala Ile Ala Pro Leu Thr Ile Thr Leu Val Arg
1                   5                   10                  15
```

```
Glu Glu Val Ile Asp Phe Ser Lys Pro Phe Met Ser Leu Gly Ile Ser
            20                  25                  30
Ile Met Ile Lys Lys Pro Gln
        35
```

(2) INFORMATION FOR SEQ ID NO: 30:

(i) SEQUENCE CHARACTERISTICS:
        (A) LENGTH: 259 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 30:

```
Lys Ser Lys Pro Gly Val Phe Ser Phe Leu Asp Pro Leu Ala Tyr Glu
 1               5                  10                  15
Ile Trp Met Cys Ile Val Phe Ala Tyr Ile Gly Val Ser Val Val Leu
            20                  25                  30
Phe Leu Val Ser Arg Phe Ser Pro Tyr Glu Trp His Thr Glu Glu Phe
        35                  40                  45
Glu Asp Gly Arg Glu Thr Gln Ser Ser Glu Ser Thr Asn Glu Phe Gly
    50                  55                  60
Ile Phe Asn Ser Leu Trp Phe Ser Leu Gly Ala Phe Met Arg Gln Gly
65                  70                  75                  80
Cys Asp Ile Ser Pro Arg Ser Leu Ser Gly Arg Ile Val Gly Gly Val
                85                  90                  95
Trp Trp Phe Phe Thr Leu Ile Ile Ile Ser Ser Tyr Thr Ala Asn Leu
            100                 105                 110
Ala Ala Phe Leu Thr Val Glu Arg Met Val Ser Pro Ile Glu Ser Ala
        115                 120                 125
Glu Asp Leu Ser Lys Gln Thr Glu Ile Ala Tyr Gly Thr Leu Asp Ser
    130                 135                 140
Gly Ser Thr Lys Glu Phe Phe Arg Arg Ser Lys Ile Ala Val Phe Asp
145                 150                 155                 160
Lys Met Trp Thr Tyr Met Arg Ser Ala Glu Pro Ser Val Phe Val Arg
                165                 170                 175
Thr Thr Ala Glu Gly Val Ala Arg Val Arg Lys Ser Lys Gly Lys Tyr
            180                 185                 190
Ala Tyr Leu Leu Glu Ser Thr Met Asn Glu Tyr Ile Glu Gln Arg Lys
        195                 200                 205
Pro Cys Asp Thr Met Lys Val Gly Gly Asn Leu Asp Ser Lys Gly Tyr
    210                 215                 220
Gly Ile Ala Thr Pro Lys Gly Ser Ser Leu Gly Thr Pro Val Asn Leu
225                 230                 235                 240
Ala Val Leu Lys Leu Ser Glu Gln Gly Val Leu Asp Lys Leu Lys Asn
                245                 250                 255
Lys Trp Trp
```

(2) INFORMATION FOR SEQ ID NO: 31:

(i) SEQUENCE CHARACTERISTICS:
        (A) LENGTH: 94 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 31:

```
Tyr Asp Lys Gly Glu Cys Gly Ala Lys Asp Ser Gly Ser Lys Glu Lys
1               5                   10                  15

Thr Ser Ala Leu Ser Leu Ser Asn Val Ala Gly Val Phe Tyr Ile Leu
            20                  25                  30

Val Gly Gly Leu Gly Ala Met Leu Val Ala Leu Ile Glu Phe Cys Tyr
        35                  40                  45

Lys Ser Arg Ala Glu Ala Lys Arg Met Lys Val Ala Lys Asn Pro Gln
50                  55                  60

Asn Ile Asn Pro Ser Ser Gln Asn Ser Gln Asn Phe Ala Thr Tyr
65              70                  75                  80

Lys Glu Gly Tyr Asn Val Tyr Gly Ile Glu Ser Val Lys Ile
                85                  90
```

(2) INFORMATION FOR SEQ ID NO: 32:

(i) SEQUENCE CHARACTERISTICS:
        (A) LENGTH: 2484 base pairs
        (B) TYPE: nucleic acid
        (C) STRANDEDNESS: single
        (D) TOPOLOGY: linear (ix) FEATURE:
        (A) NAME/KEY: mat_peptide
        (B) LOCATION: 1...2424
        (D) OTHER INFORMATION:

(xi) SEQUENCE DESCRIPTION: SEQ ID NO: 32:

```
ATG GAG ATT CTG TTT TCT ATT TCC ATT CTT GCT CTT CTC TTT TCC GGA        48
Met Glu Ile Leu Phe Ser Ile Ser Ile Leu Ala Leu Leu Phe Ser Gly
1               5                   10                  15

GTA GTA GCT GCT CCA AGC GAC GAT GAT GTT TTC GAA GAG GTT AGG GTT        96
Val Val Ala Ala Pro Ser Asp Asp Asp Val Phe Glu Glu Val Arg Val
            20                  25                  30

GGA TTG GTG GTT GAC TTG AGT TCT ATT CAA GGC AAG ATT CTG GAA ACT       144
Gly Leu Val Val Asp Leu Ser Ser Ile Gln Gly Lys Ile Leu Glu Thr
        35                  40                  45

TCT TTT AAC TTA GCG CTT TCA GAT TTC TAT GGC ATC AAC AAT GGA TAC       192
Ser Phe Asn Leu Ala Leu Ser Asp Phe Tyr Gly Ile Asn Asn Gly Tyr
50                  55                  60

CGA ACC AGA GTC TCT GTT TTG GTC AGA GAC TCC CAA GGA GAC CCG ATC       240
Arg Thr Arg Val Ser Val Leu Val Arg Asp Ser Gln Gly Asp Pro Ile
65                  70                  75                  80

ATT GCT CTT GCC GCC GCT ACT GAT CTT CTC AAA AAT GCA AAA GCG GAA       288
Ile Ala Leu Ala Ala Ala Thr Asp Leu Leu Lys Asn Ala Lys Ala Glu
                85                  90                  95

GCC ATT GTT GGT GCA CAA TCA TTA CAA GAG GCA AAG CTT TTG GCG ACG       336
Ala Ile Val Gly Ala Gln Ser Leu Gln Glu Ala Lys Leu Leu Ala Thr
            100                 105                 110

ATT AGC GAA AAA GCT AAA GTT CCG GTC ATA TCT ACT TTC TTG CCA AAC       384
Ile Ser Glu Lys Ala Lys Val Pro Val Ile Ser Thr Phe Leu Pro Asn
        115                 120                 125

ACG TTA TCT TTG AAG AAA TAC GAT AAC TTT ATT CAA TGG ACG CAT GAT       432
Thr Leu Ser Leu Lys Lys Tyr Asp Asn Phe Ile Gln Trp Thr His Asp
    130                 135                 140

ACT ACA TCA GAG GCT AAG GGA ATT ACA AGT CTC ATA CAA GAT TTC AGT       480
Thr Thr Ser Glu Ala Lys Gly Ile Thr Ser Leu Ile Gln Asp Phe Ser
145                 150                 155                 160

TGT AAA TCG GTT GTG GTT ATA TAC GAG GAT GCT GAT GAT TGG AGT GAG       528
```

```
                Cys Lys Ser Val Val Ile Tyr Glu Asp Ala Asp Trp Ser Glu
                            165                 170                 175

AGT TTG CAA ATA TTG GTT GAG AAT TTT CAA GAT AAA GGA ATC TAT ATC              576
Ser Leu Gln Ile Leu Val Glu Asn Phe Gln Asp Lys Gly Ile Tyr Ile
            180                 185                 190

GCT CGT TCT GCT TCT TTT GCA GTC TCA TCA TCA GGA GAA AAT CAT ATG              624
Ala Arg Ser Ala Ser Phe Ala Val Ser Ser Ser Gly Glu Asn His Met
        195                 200                 205

ATG AAT CAG CTA AGG AAG CTT AAG GTC TCA AGA GCA TCG GTT TTT GTG              672
Met Asn Gln Leu Arg Lys Leu Lys Val Ser Arg Ala Ser Val Phe Val
210                 215                 220

GTG CAT ATG TCC GAG ATT CTT GTT TCT CGT CTC TTC CAA TGT GTA GAG              720
Val His Met Ser Glu Ile Leu Val Ser Arg Leu Phe Gln Cys Val Glu
225                 230                 235                 240

AAG TTA GGT TTG ATG GAA GAA GCG TTC GCT TGG ATC CTC ACT GCA AGA              768
Lys Leu Gly Leu Met Glu Glu Ala Phe Ala Trp Ile Leu Thr Ala Arg
                245                 250                 255

ACC ATG AAC TAC TTG GAA CAT TTT GCA ATA ACT AGG TCG ATG CAA GGG              816
Thr Met Asn Tyr Leu Glu His Phe Ala Ile Thr Arg Ser Met Gln Gly
            260                 265                 270

GTC ATT GGT TTC AAA TCT TAC ATC CCT GTA TCT GAA GAA GTT AAG AAT              864
Val Ile Gly Phe Lys Ser Tyr Ile Pro Val Ser Glu Glu Val Lys Asn
        275                 280                 285

TTT ACT TCA AGA TTG AGG AAA CGT ATG GGA GAT GAT ACA GAA ACA GAG              912
Phe Thr Ser Arg Leu Arg Lys Arg Met Gly Asp Asp Thr Glu Thr Glu
290                 295                 300

CAT TCT AGT GTA ATC ATC GGT TTA CGC GCA CAC GAT ATC GCT TGT ATT              960
His Ser Ser Val Ile Ile Gly Leu Arg Ala His Asp Ile Ala Cys Ile
305                 310                 315                 320

CTA GCA AAT GCA GTA GAG AAG TTC AGT GTA AGT GGT AAA GTT GAA GCA             1008
Leu Ala Asn Ala Val Glu Lys Phe Ser Val Ser Gly Lys Val Glu Ala
                325                 330                 335

TCT TCG AAT GTA TCA GCT GAT CTT CTG GAT ACA ATT AGA CAT AGT AGA             1056
Ser Ser Asn Val Ser Ala Asp Leu Leu Asp Thr Ile Arg His Ser Arg
            340                 345                 350

TTC AAG GGT TTG AGT GGT GAC ATC CAA ATC TCT GAC AAC AAA TTT ATC             1104
Phe Lys Gly Leu Ser Gly Asp Ile Gln Ile Ser Asp Asn Lys Phe Ile
        355                 360                 365

TCA GAG ACA TTT GAA ATC GTG AAT ATT GGA AGA GAA AAA CAG AGA AGG             1152
Ser Glu Thr Phe Glu Ile Val Asn Ile Gly Arg Glu Lys Gln Arg Arg
370                 375                 380

ATA GGA TTA TGG AGT GGT GGT AGT TTT AGC CAA AGA AGA CAG ATT GTT             1200
Ile Gly Leu Trp Ser Gly Gly Ser Phe Ser Gln Arg Arg Gln Ile Val
385                 390                 395                 400

TGG CCT GGC AGG TCT CGT AAG ATC CCA AGA CAC CGT GTT TTG GCA GAG             1248
Trp Pro Gly Arg Ser Arg Lys Ile Pro Arg His Arg Val Leu Ala Glu
                405                 410                 415

AAA GGT GAA AAG AAG GTG CTT AGG GTC TTA GTT ACC GCA GGA AAC AAG             1296
Lys Gly Glu Lys Lys Val Leu Arg Val Leu Val Thr Ala Gly Asn Lys
            420                 425                 430

GTC CCG CAT CTA GTG TCG GTG CGT CCT GAT CCT GAA ACA GGT GTT AAT             1344
Val Pro His Leu Val Ser Val Arg Pro Asp Pro Glu Thr Gly Val Asn
        435                 440                 445

ACT GTC TCT GGA TTC TGC GTA GAG GTT TTC AAG ACT TGC ATT GCT CCT             1392
Thr Val Ser Gly Phe Cys Val Glu Val Phe Lys Thr Cys Ile Ala Pro
450                 455                 460

TTT AAC TAC GAG CTT GAA TTC ATA CCT TAC CGT GGA AAC AAT GAC AAT             1440
Phe Asn Tyr Glu Leu Glu Phe Ile Pro Tyr Arg Gly Asn Asn Asp Asn
465                 470                 475                 480
```

-continued

| | | |
|---|---|---|
| CTT GCT TAT CTA CTT TCT ACT CAG AGA GAC AAG TAT GAT GCA GCA GTT<br>Leu Ala Tyr Leu Leu Ser Thr Gln Arg Asp Lys Tyr Asp Ala Ala Val<br>485 490 495 | 1488 | |
| GGT GAT ATC ACC ATC ACT TCC AAC AGA TCT TTG TAT GTT GAT TTT ACT<br>Gly Asp Ile Thr Ile Thr Ser Asn Arg Ser Leu Tyr Val Asp Phe Thr<br>500 505 510 | 1536 | |
| TTG CCG TAC ACT GAC ATT GGT ATT GGA ATC CTG ACA GTA AAA AAG AAA<br>Leu Pro Tyr Thr Asp Ile Gly Ile Gly Ile Leu Thr Val Lys Lys Lys<br>515 520 525 | 1584 | |
| AGC CAA GGG ATG TGG ACT TTC TTT GAT CCT TTT GAA AAA TCC TTG TGG<br>Ser Gln Gly Met Trp Thr Phe Phe Asp Pro Phe Glu Lys Ser Leu Trp<br>530 535 540 | 1632 | |
| CTA GCA AGT GGA GCT TTC TTT GTC TTA ACT GGG ATT GTT GTT TGG TTA<br>Leu Ala Ser Gly Ala Phe Phe Val Leu Thr Gly Ile Val Val Trp Leu<br>545 550 555 560 | 1680 | |
| GTT GAA CGG TCC GTT AAT CCG GAA TTT CAG GGC TCT TGG GGA CAA CAA<br>Val Glu Arg Ser Val Asn Pro Glu Phe Gln Gly Ser Trp Gly Gln Gln<br>565 570 575 | 1728 | |
| CTT AGT ATG ATG CTC TGG TTT GGT TTC TCA ACC ATT GTA TTT GCT CAC<br>Leu Ser Met Met Leu Trp Phe Gly Phe Ser Thr Ile Val Phe Ala His<br>580 585 590 | 1776 | |
| AGA GAG AAG CTA CAG AAA ATG TCA TCA AGA TTC TTA GTC ATA GTT TGG<br>Arg Glu Lys Leu Gln Lys Met Ser Ser Arg Phe Leu Val Ile Val Trp<br>595 600 605 | 1824 | |
| GTT TTT GTG GTG TTA ATA TTG ACT TCA AGT TAC AGC GCA AAC TTG ACA<br>Val Phe Val Val Leu Ile Leu Thr Ser Ser Tyr Ser Ala Asn Leu Thr<br>610 615 620 | 1872 | |
| TCA ACC AAG ACC ATT TCT CGC ATG CAA TTA AAT CAT CAG ATG GTT TTC<br>Ser Thr Lys Thr Ile Ser Arg Met Gln Leu Asn His Gln Met Val Phe<br>625 630 635 640 | 1920 | |
| GGG GGA TCT ACG ACG TCA ATG ACT GCG AAG CTC GGA TCC ATT AAT GCA<br>Gly Gly Ser Thr Thr Ser Met Thr Ala Lys Leu Gly Ser Ile Asn Ala<br>645 650 655 | 1968 | |
| GTT GAG GCC TAT GCA CAA CTT TTG CGA GAT GGA ACT CTT AAT CAT GTC<br>Val Glu Ala Tyr Ala Gln Leu Leu Arg Asp Gly Thr Leu Asn His Val<br>660 665 670 | 2016 | |
| ATC AAT GAA ATA CCT TAT CTC AGT ATC CTT ATC GGA AAT TAT CCG AAT<br>Ile Asn Glu Ile Pro Tyr Leu Ser Ile Leu Ile Gly Asn Tyr Pro Asn<br>675 680 685 | 2064 | |
| GAT TTC GTA ATG ACA GAT AGA GTG ACT AAT ACC AAT GGC TTT GGC TTT<br>Asp Phe Val Met Thr Asp Arg Val Thr Asn Thr Asn Gly Phe Gly Phe<br>690 695 700 | 2112 | |
| ATG TTC CAG AAA GGT TCG GAT TTG GTT CCT AAA GTA TCG CGA GAA ATC<br>Met Phe Gln Lys Gly Ser Asp Leu Val Pro Lys Val Ser Arg Glu Ile<br>705 710 715 720 | 2160 | |
| GCG AAG CTA AGA TCA TTG GGA ATG TTG AAA GAC ATG GAG AAA AAA TGG<br>Ala Lys Leu Arg Ser Leu Gly Met Leu Lys Asp Met Glu Lys Lys Trp<br>725 730 735 | 2208 | |
| TTT CAA AAA CTG GAT TCA CTA AAT GTA CAT TCC AAC ACC GAG GAA GTT<br>Phe Gln Lys Leu Asp Ser Leu Asn Val His Ser Asn Thr Glu Glu Val<br>740 745 750 | 2256 | |
| GCA TCT ACC AAC GAC GAT GAT GAG GCA TCT AAG CGA TTC ACC TTC CGT<br>Ala Ser Thr Asn Asp Asp Asp Glu Ala Ser Lys Arg Phe Thr Phe Arg<br>755 760 765 | 2304 | |
| GAG TTG CGC GGT TTG TTC ATC ATT GCG GGA GCT GCT CAT GTT CTC GTA<br>Glu Leu Arg Gly Leu Phe Ile Ile Ala Gly Ala Ala His Val Leu Val<br>770 775 780 | 2352 | |
| CTA GCC CTA CAT CTC TTT CAT ACG CGT CAA GAG GTA TCA CGA CTA TGC<br>Leu Ala Leu His Leu Phe His Thr Arg Gln Glu Val Ser Arg Leu Cys<br>785 790 795 800 | 2400 | |

```
ACC AAA CTT CAA AGC TTC TAT AAG TAA AAA GTG ATC CAT CGT TCA TAA     2448
Thr Lys Leu Gln Ser Phe Tyr Lys  *  Lys Val Ile His Arg Ser  *
            805                 810                     815

GCT CTA CTA TAG CAA TTG ACG GGA CAG GAC TCA TAA                     2484
Ala Leu Leu  *  Gln Leu Thr Gly Gln Asp Ser  *
        820                 825
```

(2) INFORMATION FOR SEQ ID NO: 33:

(i) SEQUENCE CHARACTERISTICS:
      (A) LENGTH: 808 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO: 33:

```
Met Glu Ile Leu Phe Ser Ile Ser Ile Leu Ala Leu Leu Phe Ser Gly
 1               5                  10                  15

Val Val Ala Ala Pro Ser Asp Asp Val Phe Glu Glu Val Arg Val
            20                  25                  30

Gly Leu Val Val Asp Leu Ser Ser Ile Gln Gly Lys Ile Leu Glu Thr
            35                  40                  45

Ser Phe Asn Leu Ala Leu Ser Asp Phe Tyr Gly Ile Asn Asn Gly Tyr
50                      55                  60

Arg Thr Arg Val Ser Val Leu Val Arg Asp Ser Gln Gly Asp Pro Ile
65                  70                  75                  80

Ile Ala Leu Ala Ala Ala Thr Asp Leu Leu Lys Asn Ala Lys Ala Glu
                85                  90                  95

Ala Ile Val Gly Ala Gln Ser Leu Gln Glu Ala Lys Leu Leu Ala Thr
                100                 105                 110

Ile Ser Glu Lys Ala Lys Val Pro Val Ile Ser Thr Phe Leu Pro Asn
            115                 120                 125

Thr Leu Ser Leu Lys Lys Tyr Asp Asn Phe Ile Gln Trp Thr His Asp
130                 135                 140

Thr Thr Ser Glu Ala Lys Gly Ile Thr Ser Leu Ile Gln Asp Phe Ser
145                 150                 155                 160

Cys Lys Ser Val Val Ile Tyr Glu Asp Ala Asp Asp Trp Ser Glu
                165                 170                 175

Ser Leu Gln Ile Leu Val Glu Asn Phe Gln Asp Lys Gly Ile Tyr Ile
            180                 185                 190

Ala Arg Ser Ala Ser Phe Ala Val Ser Ser Ser Gly Glu Asn His Met
            195                 200                 205

Met Asn Gln Leu Arg Lys Leu Lys Val Ser Arg Ala Ser Val Phe Val
210                 215                 220

Val His Met Ser Glu Ile Leu Val Ser Arg Leu Phe Gln Cys Val Glu
225                 230                 235                 240

Lys Leu Gly Leu Met Glu Glu Ala Phe Ala Trp Ile Leu Thr Ala Arg
                245                 250                 255

Thr Met Asn Tyr Leu Glu His Phe Ala Ile Thr Arg Ser Met Gln Gly
            260                 265                 270

Val Ile Gly Phe Lys Ser Tyr Ile Pro Val Ser Glu Glu Val Lys Asn
            275                 280                 285

Phe Thr Ser Arg Leu Arg Lys Arg Met Gly Asp Asp Thr Glu Thr Glu
290                 295                 300
```

```
His Ser Ser Val Ile Ile Gly Leu Arg Ala His Asp Ile Ala Cys Ile
305                 310                 315                 320

Leu Ala Asn Ala Val Glu Lys Phe Ser Val Ser Gly Lys Val Glu Ala
                325                 330                 335

Ser Ser Asn Val Ser Ala Asp Leu Leu Asp Thr Ile Arg His Ser Arg
                340                 345                 350

Phe Lys Gly Leu Ser Gly Asp Ile Gln Ile Ser Asp Asn Lys Phe Ile
            355                 360                 365

Ser Glu Thr Phe Glu Ile Val Asn Ile Gly Arg Glu Lys Gln Arg Arg
        370                 375                 380

Ile Gly Leu Trp Ser Gly Gly Ser Phe Ser Gln Arg Gln Ile Val
385                 390                 395                 400

Trp Pro Gly Arg Ser Arg Lys Ile Pro Arg His Arg Val Leu Ala Glu
                405                 410                 415

Lys Gly Glu Lys Lys Val Leu Arg Val Leu Val Thr Ala Gly Asn Lys
                420                 425                 430

Val Pro His Leu Val Ser Val Arg Pro Asp Pro Glu Thr Gly Val Asn
            435                 440                 445

Thr Val Ser Gly Phe Cys Val Glu Val Phe Lys Thr Cys Ile Ala Pro
        450                 455                 460

Phe Asn Tyr Glu Leu Glu Phe Ile Pro Tyr Arg Gly Asn Asn Asp Asn
465                 470                 475                 480

Leu Ala Tyr Leu Leu Ser Thr Gln Arg Asp Lys Tyr Asp Ala Ala Val
                485                 490                 495

Gly Asp Ile Thr Ile Thr Ser Asn Arg Ser Leu Tyr Val Asp Phe Thr
            500                 505                 510

Leu Pro Tyr Thr Asp Ile Gly Ile Gly Ile Leu Thr Val Lys Lys Lys
        515                 520                 525

Ser Gln Gly Met Trp Thr Phe Phe Asp Pro Phe Glu Lys Ser Leu Trp
    530                 535                 540

Leu Ala Ser Gly Ala Phe Phe Val Leu Thr Gly Ile Val Val Trp Leu
545                 550                 555                 560

Val Glu Arg Ser Val Asn Pro Glu Phe Gln Gly Ser Trp Gly Gln Gln
                565                 570                 575

Leu Ser Met Met Leu Trp Phe Gly Phe Ser Thr Ile Val Phe Ala His
                580                 585                 590

Arg Glu Lys Leu Gln Lys Met Ser Ser Arg Phe Leu Val Ile Val Trp
        595                 600                 605

Val Phe Val Val Leu Ile Leu Thr Ser Ser Tyr Ser Ala Asn Leu Thr
        610                 615                 620

Ser Thr Lys Thr Ile Ser Arg Met Gln Leu Asn His Gln Met Val Phe
625                 630                 635                 640

Gly Gly Ser Thr Thr Ser Met Thr Ala Lys Leu Gly Ser Ile Asn Ala
                645                 650                 655

Val Glu Ala Tyr Ala Gln Leu Leu Arg Asp Gly Thr Leu Asn His Val
                660                 665                 670

Ile Asn Glu Ile Pro Tyr Leu Ser Ile Leu Ile Gly Asn Tyr Pro Asn
            675                 680                 685

Asp Phe Val Met Thr Asp Arg Val Thr Asn Thr Asn Gly Phe Gly Phe
            690                 695                 700

Met Phe Gln Lys Gly Ser Asp Leu Val Pro Lys Val Ser Arg Glu Ile
705                 710                 715                 720

Ala Lys Leu Arg Ser Leu Gly Met Leu Lys Asp Met Glu Lys Lys Trp
```

```
                        725                 730                 735
Phe Gln Lys Leu Asp Ser Leu Asn Val His Ser Asn Thr Glu Glu Val
            740                 745                 750
Ala Ser Thr Asn Asp Asp Glu Ala Ser Lys Arg Phe Thr Phe Arg
            755                 760                 765
Glu Leu Arg Gly Leu Phe Ile Ile Ala Gly Ala Ala His Val Leu Val
    770                 775                 780
Leu Ala Leu His Leu Phe His Thr Arg Gln Glu Val Ser Arg Leu Cys
785                 790                 795                 800
Thr Lys Leu Gln Ser Phe Tyr Lys
                805
```

(2) INFORMATION FOR SEQ ID NO: 34:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 34:

```
Lys Val Ile His Arg Ser
1               5
```

(2) INFORMATION FOR SEQ ID NO: 35:

(i) SEQUENCE CHARACTERISTICS:
        (A) LENGTH: 3 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 35:

```
Ala Leu Leu
1
```

(2) INFORMATION FOR SEQ ID NO: 36:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 36:

```
Gln Leu Thr Gly Gln Asp Ser
1               5
```

PLANT GLUTAMATE RECEPTORS

This is a division of application Ser. No. 08/658,335, filed Jun. 6, 1996 now U.S. Pat. No. 5,981,703 which is a continuation-in-part of application Ser. No. 08/629,291, filed Apr. 8, 1996 now U.S. Pat. No. 5,959,174, which is a continuation-in-part of application Ser. No. 08/481,956, filed Jun. 7, 1995 now U.S. Pat. No. 5,824,867.

This invention was made with U.S. government support under NIH grant GM-32877. The U.S. government has certain rights in the invention.

1. INTRODUCTION

The invention relates to a family of glutamate receptors (GluR) in plants, compounds that modulate the activity of the plant GluR, and the use of such compounds as plant growth regulators, including herbicides. The invention also relates to nucleotide sequences encoding the plant GluR and to plant assay systems designed to identify novel plant growth regulators that may be used as herbicides and/or pharmaceutical drugs.

2. BACKGROUND OF THE INVENTION

2.1. Metabolic and Regulatory Roles of Glutamate in Plants

Glutamate has important roles in plant nitrogen metabolism. Glutamate is the amino acid into which inorganic nitrogen is first assimilated into organic form. Plants have three distinct nitrogen processes related to nitrogen metabolism: (1) primary nitrogen-assimilation, (2) photorespiration, and (3) nitrogen "recycling." All three processes involve assimilation of ammonia into glutamate and glutamine by the operation of glutamine synthetase (GS) and glutamate synthase (GOGAT). Glutamate and glutamine, being the first products of nitrogen-assimilation, in turn serve as nitrogen donors in the biosynthesis of essentially all amino acids, nucleic acids, and other nitrogen-containing compounds such as chlorophyll (Lea et al., in: Recent Advances in Phytochemistry, edited by Poulton et al., New York and London: Plenum Press, 1988, pp. 157–189).

Glutamate is also a principal "nitrogen-transport" compound in plants. It and glutamine are two major amino acids used to transport nitrogen within a plant (Lea and Miflin, in: The Biochemistry of Plants, Vol. 5, edited by Stumpf and Conn, Academic Press, 1980, pp. 569–607; Urquhart and Joy, 1981, Plant Physiol. 68:750–754). In light-grown metabolically active plants, glutamate and glutamine are used in anabolic reactions and are transported as such. By contrast, in etiolated or dark-adapted plants, glutamine is converted into inert asparagine for long-term nitrogen storage.

Glutamate also may be a signal or regulatory molecule in regulating the expression of plant genes. Specifically, glutamate along with glutamine and asparagine appears to have an antagonistic role to that of sucrose in regulating certain nitrogen assimilation genes. Sucrose has been shown to induce the expression of genes for nitrate reductase (NR), nitrite reductase (NiR), and chloroplastic glutamine synthetase (GS2) in tobacco (Saur et al., 1987, Z. Naturforsch. 42:270–278; Vincentz et al., 1993, Plant J. 3:315–324). Sucrose also induces genes for GS2 and ferroredoxin-dependent glutamate synthase (Fd-GOGAT) in Arabidopsis. Sucrose-induction of the NR and NiR in tobacco is suppressed by subsequent additions of glutamine, glutamate or asparagine to the media (Vincentz et al., ibid.). Conversely, a nitrogen metabolism gene, glutamine-dependent asparagine synthetase (ASN1), in Arabidopsis is repressed by light or sucrose (Lam et al., 1994, Plant Physiol. 106:1347–1357). The sucrose repression of ASN1 can be relieved by additions of glutamine, glutamate, or asparagine (Id.).

2.2. Glutamate Receptors in Animal Cells

Excitatory amino acids constitute the principal neurotransmitter receptors that mediate synaptic communication in animals (Gasic et al., 1992, Annu. Rev. Physiol. 54: 507–536). In particular, L-glutamate is the major excitatory neurotransmitter of the mammalian central nervous system (Monaghan et al., 1989, Annu. Rev. Pharmacol. Toxic. 29: 365–402). Glutamate signaling in animals is important for many physiological and pathological processes such as developmental plasticity, long-term potentiation, and excitotoxic damage in ischemia and other neurodegenerative disorders (Choi, 1988, Neuron 1: 623–624; Kennedy, 1989, Cell 59: 777–787).

In animals, glutamate can trigger various downstream physiological responses by interacting with different GluR. GluRs in animals are involved in central nervous system (CNS) disorders such as Huntington's disease, Parkinson's disease and Alzheimer's disease. The GluR is involved in the initiation and propagation of seizures and in massive neuronal cell death during periods of ischemia and hypoglycemia. GluRs have been grouped into five distinct subtypes (Gasic et al., 1992, Annu. Rev. Physiol. 54: 507–536): (a) NMDA (N-methyl-D-aspartate), (b) KA (Kainate), (c) AMPA (alpha-amino-3-hydroxy-5-methyl-4-isoxazole propionate), (d) L-AP4 (2-amino-4-phosphonobutyrate) and (e) ACPD (trans-1-amino-cyclopentane-1,3 dicarboxylate). NMPA, KA and AMPA, which form ligand gated ion channels that are activated on a msec scale, are the ionotropic (iGluR) subtypes. By contrast, metabotropic (mGluR) subtypes, L-AP4 and ACPD, are coupled to G proteins and operate on a time scale of several hundred msec to seconds. LAP-4 receptor probably acts via a G protein by increasing the hydrolysis of cGMP and subsequently leads to the closure of ion channels conducting an inward current. The ACPD subtype, which couples with a G protein that is linked to inositol phosphate/diacylglycerol formation and subsequent release of calcium from internal stores. Both iGluR and mGluR seem to play a role in the activation of transcription factors, such as c-jun and c-fos (Condorelli et al., 1993, J. Neurochem. 60: 877–885; Condorelli et al., 1994, Neurochem. Res. 19: 489–499).

2.2.1. Ionotropic Glutamate Receptors

There are major differences in the neurophysiological functions of the three subtypes of iGluR (Seeburg, 1995, TINS 16:359–365). AMPA receptors are found in the majority of all fast excitatory neurotransmission. The very low Ca++ permeability of AMPA receptor suggests that they probably do not trigger biochemical reactions directly via an increase in intracellular Ca++ levels. In NMDA receptor, Ca++ flux will trigger different processes ranging from trophic developmental actions to an activity-dependent resetting of the synaptic strength underlying some forms of learning and memory. The significance of high-affinity kainate sites in the nervous systems is yet to be fully understood.

(A) AMPA Receptor

AMPA receptors consist of at least four different subunits: GluR1–GluR4. The two major forms, named "flip" and "flop", which are formed by differential splicing, display different expression profiles in the mature and the developing brain (Sommer et al., 1990, Science 249:1580–1585). For GluR2 subunit, RNA editing (Q to R) in transmembrane domain (TM) II has been shown to regulate the Ca++ permeability. RNA editing leads to a decrease in Ca++ permeability (Burnashev et al., 1992, Neuron, 8:189–198; Hume et al., 1991, Science 253:1028–1031).

(B) Kainate Receptors

High-affinity kainate receptors are composed of subunits GluR5–GluR7, KA1, and KA2 (Seeburg et al., 1995, TINS 16:359–365). Both GluR5 and GluR6 subunits also display the Q to R editing similar to the case of GluR2 of AMPA receptors (Sommer et al., 1991, Cell 67:11–19). GluR6 has two additional positions in TMI that are modified by RNA editing (Kohler et al., 1993, Neuron 10:491–500). For GluR6, only when TMI is edited does editing in TMII (Q to R) influence Ca++ permeability (Kohler et al., 1993, Neuron 10:491–500). In contrast to the AMPA receptor channel, GluR6(R) channels edited in TMI show a higher Ca++ permeability than GluR6(Q) channels (Kohler et al., 1993, Neuron 10:491–500).

(C) NMDA Receptor

NMDA receptors are highly permeable to Ca++. The NMDA receptor can be reconstituted as heteromeric structures from two subunit types: NRI and one of the four NR2 (NR2A–NR2D) (Seeburg, 1995, TINS 16:359–365). All of the subunits do not show RNA editing in TMI and TMII. In fact all subunits contain an N at the site which Q to R editing occurs in non-NMDA iGluR. The most distinct feature of NMDA receptors is that they require both glycine and glutamate or both glycine and NMDA to activate the channel. The NMDA receptor has been linked to regulation of coccidian rhythm in rat brains.

2.2.2. Metabotropic Glutamate Receptors

In contrast to ionotropic glutamate receptors. (iGluR) the hallmark of the mGluR receptors resides on the fact that these molecules are coupled to G proteins and thus able to elicit typical G protein-driven intracellular responses (Gasic et al., 1992, Annu. Rev. Physiol. 54:507–536; Minakami et al., 1994, Biochem. Biophys.. Res. Commun. 199:1136–1143; Schoepp et al., 1993, Trends in Pharmacol. Sci. 14:13–20).

The cloning of mGluR1 from a expression cDNA library of a rat cerebellum (mGluR1a), was followed by the cloning and characterization of six other mGluR genes (Schoepp et al., 1993, Trends in Pharmacol. Sci. 14:13–20). The mGluR1 a, the prototype member of the family, possess a large extracellular domain, a putative "seven pass" transmembrane region and display highly conserved amino acids with other members of the mGluRs both at the membrane spanning region, extracellular region and intracytoplasmic loops between transmembrane domains (Gasic et al., 1992, Annu. Rev. Physiol. 54:507–536; Minakami et al., 1994, Biochem. Biophys. Res. Commun. 199:1136–1143; Schoepp et al., 1993, Trends in Pharmacol. Sci. 14:13–20). The mGluR genes are unique in that they do not show significant homology with any of the previously characterized G proteins (Nakanishi et al., 1994, In: Toward a molecular basis of alcohol use and abuse. ed. by Jansson et al. p 71–80; Schoepp et al., 1993, Trends in Pharmacol. Sci. 14:13–20) and very little is known on the signal transduction mechanisms and second messenger responses for each mGluR receptor (Schoepp et al., 1993, Trends in Pharmac. Sci. 14:13–20).

Studies in the in situ localization of mRNA encoding the different mGluRs shows them to be differentially distributed in the brain with cells from diverse tissues expressing one or more combinations of the various members of the mGluR family of receptors, suggestive of a relevant participation in the modulation of several important biological processes (Schoepp et al., 1993, Trends in Pharmac. Sci. 14:13–20). Indeed, the mGluR proteins have been reported to be involved with neuroprotection and neuronal pathophysiology (Baskys, 1992, Trends in Neuro Sci. 15:92–96; Schoepp et al., 1993, Trends in Pharmac. Sci. 14:13–20).

Analysis of the pharmacological properties of the individual mGluR molecules revealed that the agonists L-AP4 (L-2-amino-4-phosphonobutyrate) and ACPD (trans-1-amino-cyclopentane-1,3 dicarboxylate) can selectively stimulate different mGluR serving as a basis for the classification of this group of proteins (Nakanishi et al., 1994, In: Toward a molecular basis of alcohol use and abuse. Ed. Jansson et al. p 71–80).

(A) L-AP4 Receptor

The L-AP4 receptor has been defined electrophisiologically as an inhibitory glutamate site and biochemical evidence suggest that mGluR4, mGluR6 and mGluR7 are involved in this response (Nakanishi et al., 1994, In: Toward a molecular basis of alcohol use and abuse ed by Jansson et al. p 71–80; Schoepp et al., 1993, Trends in Pharmacol. Sci. 14:13–20). The L-AP4 receptor appears to be localized pre-synaptically such that activation inhibits the release of excitatory neurotransmitter through a mechanism involving a pertussis toxin sensitive G protein (Nakanishi et al., 1994, In: Toward a molecular basis of alcohol use and abuse. Ed. Jansson et al. p 71–80). The molecular identity and possible biological function of this group of receptors come from studies where mammalian cells were transfected with a cloned isoform of mGluR (mGluR4) responded to both L-glutamate and L-AP4 by depressing forskolin-stimulated cAMP levels (Nakanishi et al., 1994, In: Toward a molecular basis of alcohol use and abuse. ed. by Jansson, p 71–80; Schoepp et al., 1993, Trends in Pharmacol. Sci. 14:13–20). L-AP-4 has also been shown to reduce electrically-stimulated excitatory transmission, suggestive of a close interaction between mGluR and $Ca^{2+}$ channels (Cunningham et al., 1993, Life Sciences 54:135–148; Schoepp et al., 1993, Trends in Pharmac. Sci. 14:13–20) and specifically in the regulation of ionotropic glutamate receptors (Baskys, 1992, Trends in Neuro. Sci. 15:92–96). Very little is known about the signal transduction mechanisms and second messenger responses elicited by this subgroup of mGluR.

(B) ACPD Receptor

The mechanisms of signal transduction of this subgroup of receptors is better understood than that of the L-AP4-responsive mGluRs. Transfection of the cDNA for mGluR1, mGluR2, mGluR3 and mGluR5 in CHO cells revealed that this receptors are strongly responsive to the drug ACPD (trans-1-amino-cyclopentane-1,3 dicarboxylate) (Cunningham et al., 1993, Life Sciences 54:135–148; Schoepp et al., 1993, Trends in Pharmac. Sci. 14:13–20). However, not all mGluR activate the same pathways and different mGluR can elicit diverse intracellular responses. Thus, mGluR5 possess high homology with mGluR1 yet these two receptors differ in which mGluR5 does not induce formation of cAMP. Moreover, stimulation of the mGluR2 and 3 does not lead to phosphoinositide hydrolysis and mGluR2 has been shown to inhibit cAMP formation in transfection experiments (Schoepp et al. 1993). The diversity of the mGluR family of receptors can be further appreciated by the recent observation that mGluR2 and mGluR3 receptors display an unusually high response to stimulation by quisqualate when compared to other ACPD mGluR responses (Nakanishi et al., 1994, In: Toward a molecular basis of alcohol use and abuse. ed. by Jansson et al. p 71–80; Schoepp et al., 1993, Trends in Pharmacol. Sci. 14:13–20) which argues in favor of their further grouping in a more specialized division among the ACPD-induced receptors. Finally, stimulation of primary neuronal cultures with ACPD and quisqualate caused a strong and transient induction of immediate early genes such as c-fos, c-jun and zif-268 mRNAs (Condorelli et al., 1994, Neurochem Res. 19:489–499).

3. SUMMARY OF THE INVENTION

The present invention relates to a family of GluR in plants, including ionotropic (iGluR), metabotropic (mGluR) and other glutamate-like plant receptors. The plant GluRs of the invention may function as signal transducers involved in the regulation of plant growth. The invention also relates to the identification of compounds that modulate the activity of the plant GluR, and the use of such compounds as plant growth regulators, including herbicides.

The invention is based in part, on a number of unanticipated surprising discoveries. One is the discovery of plant proteins that have high degree of amino acid sequence homology to the animal ionotropic or metabotropic glutamate receptors previously found only in vertebrate tissues. The other is the finding that agonists and antagonists of animal glutamate receptors function to modulate expression of plant genes and as plant growth regulators. These agonists and antagonists structurally constrained or do not resemble glutamate. Thus, their actions in plants likely are due to their specific interaction with one or more plant glutamate receptors, rather than to general effects on glutamate-utilizing enzymes. These findings together indicate that plants have glutamate receptors that function as signal transducers.

The invention encompasses: (a) nucleotide sequences that encode the plant GluR, including mutants, recombinants, and fusion proteins; (b) the expression of such nucleotide sequences in genetically engineered host cells and/or in transgenic plants; (c) the isolated GluR plant proteins and GluR engineered gene products, including mutants, fragments, and fusion proteins; (d) antibodies to the plant GluR proteins and polypeptides; (e) screening assays involving the use of plants, transgenic plants, genetically engineered cells that express the plant GluR or mutants thereof, or GluR proteins or peptides, to identify compounds that act as agonists or antagonists; (f) the use of such agonists or antagonists as plant growth regulators, including herbicides; (g) the engineering of transgenic plants resistant to herbicidal antagonists of the plant GluR and/or transgenic plants with improved agronomic or industrial properties; and (h) the use of antagonists or agonists of the plant GluR identified in the screening assays described herein as drugs for animal use, including humans.

3.1. Definitions

An agonist is defined herein as an agent that acts like a referenced compound or that activates a receptor molecule.

An antagonist is defined herein as an agent that acts in opposition to an agonist or a referenced compound or that inhibits a receptor molecule.

A chimeric gene comprises a coding sequence linked to a regulatory region, i.e., promoters, enhancer elements and additional elements known to those skilled in the art that drive and regulate expression, that said coding sequence is not naturally linked to. The coding sequence may encode messenger RNA (mRNA), antisense RNA or ribozymes.

4. BRIEF DESCRIPTION OF THE DRAWINGS

Figure 1B:
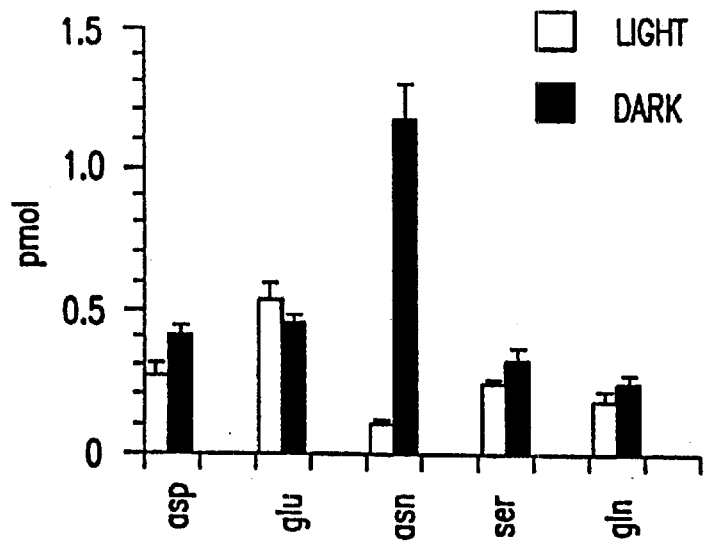
Figure 1C:
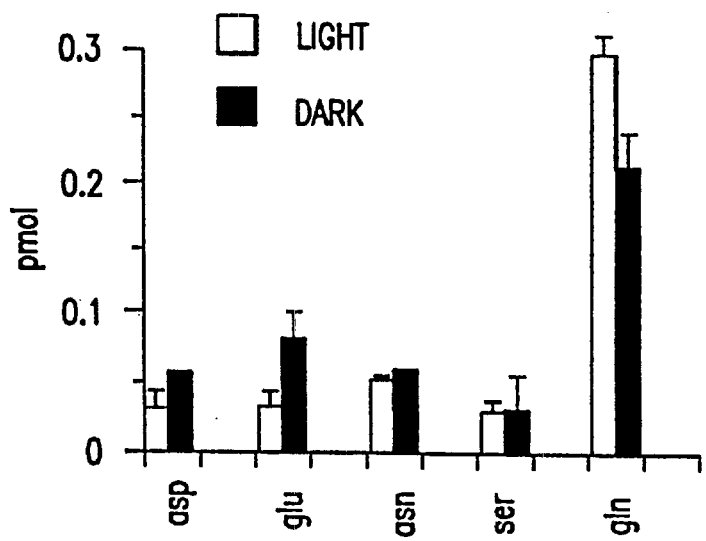

FIGS. 1A,1B,1C. HPLC Analysis of Free Amino Acids in Arabidopsis

FIG. 1A. Amino acids were extracted from leaves of Arabidopsis plants that were grown in light (empty boxes) or subsequently dark adapted for 24 hours (filled boxes). Amino acids were derivatized and separated by reverse phase HPLC. Each sample represents the average of three different plants (two leaves/plant). The standard three letter code is used for all amino acids; gaba: γ-amino burytic acid.

FIG. 1B. Average amino acid content in phloem exudates of three independent plants (one leaf/plant).

FIG. 1C. Average amino acid content of xylem sap collected from cut hypocotyls of three independent plants. Data are from Schultz (1994).

Figure 2:
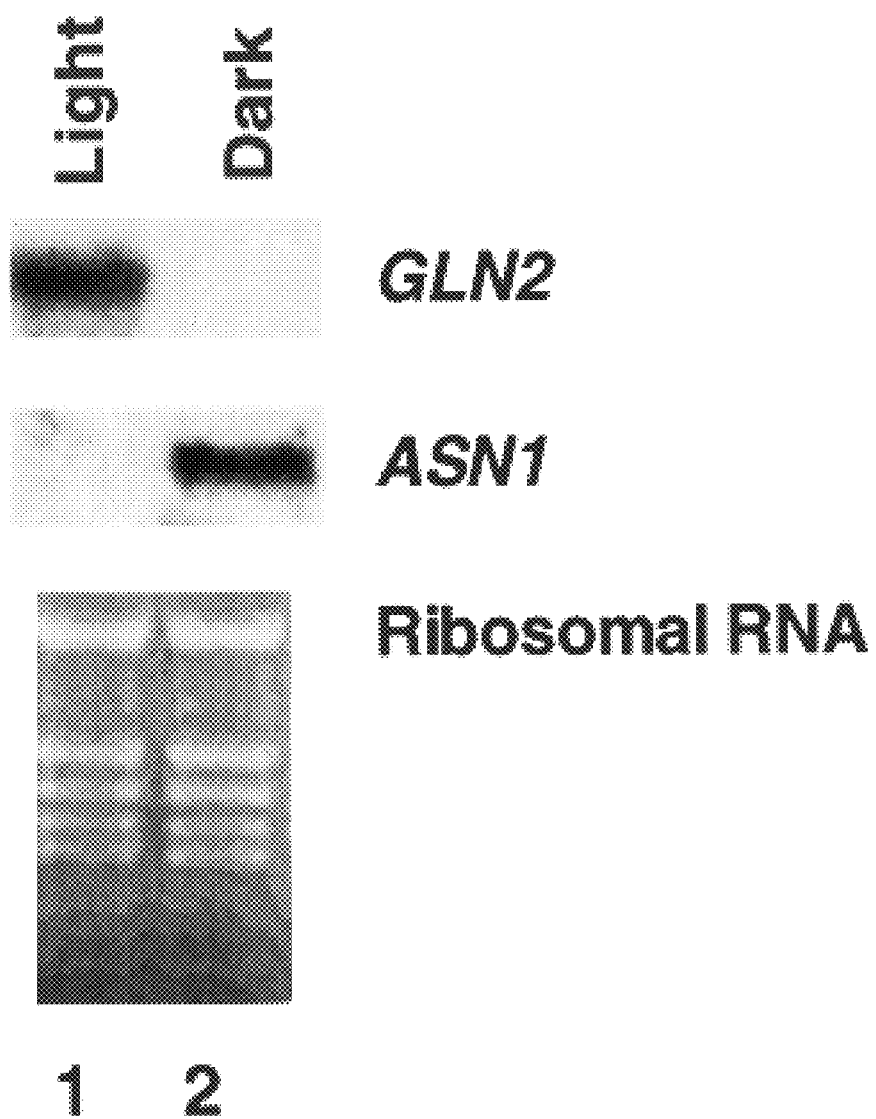

FIG. 2. Reciprocal Control By Light On Arabidopsis GLN2 and ASN1 Expression

The effects of light on GLN2 and ASN1 expression were tested in mature Arabidopsis plants. Plants were grown on soil under a 16-h light/8-h dark cycle for 2 weeks and transferred to continuous light (lane 1) or continuous darkness (lane 2) for 5 d. Total RNA (10 μg) was used for each of the lanes. Hybridization was performed by [α-$^{32}$P]dATP-labeled GLN2 or digoxigenin-labeled ASN1 DNA probes in Strategene QuikHyb solution under high stringency condition. The nylon filter was first hybridized with the GLN2 probe, then stripped, and rehybridized with the ASN1 probe. (Lam et al., 1994).

Figure 3:
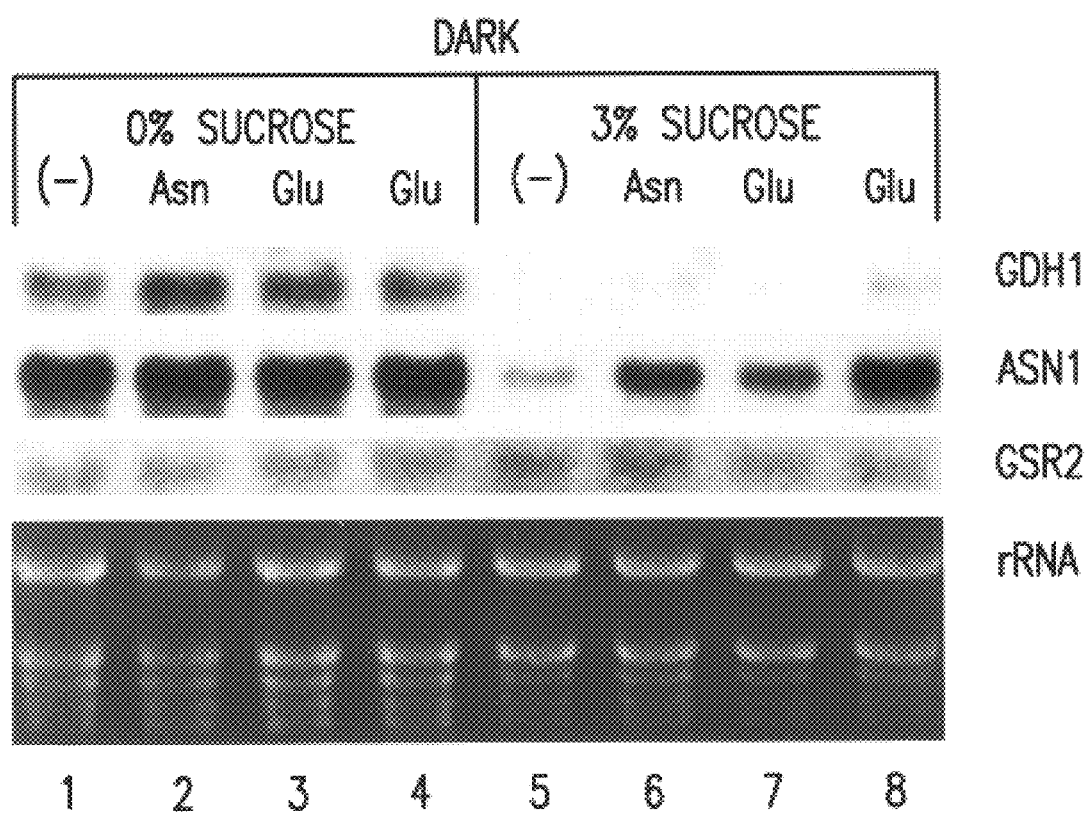

FIG. 3. Effect Of C:N Ratio On The mRNA Levels Of ASN1 And GDH

Arabidopsis seeds were grown on plates containing MS medium plus 3% (w/v) Suc under 16-h light/8-h dark cycle for 2 weeks. The plants were then transferred to media described below and grown in complete darkness for 2.5 d. Lanes 1 to 4, MS medium with no sugar; lanes 5 to 8, MS medium with 3% (w/v) Suc. MS was supplemented with 0.4 mM Asn (lanes 2 and 6), 3.4 mM Gln (lanes 3 and 7), or 3.3 mM Glu (lanes 4 and 8). The expression of ASN1, GDH, and a cytosolic GS (GSR2) were detected by northern analyses (under high-stringency conditions in 50% [v/v] formamide solution). 10 μg of total RNA was used for each lane. The nylon filter was first hybridized with ASN1, then stripped, and re-hybridized with the GSR2 probe. The nylon filter was then stripped again and re-hybridized with the GDH probe.

FIGS. 4A and 4B. A Model Depicting The Regulation Of Nitrogen Assimilation Genes By C:N Ratio FIG. 4A. In the light, when photosynthesis occurs and carbon skeletons are abundant, nitrogen is assimilated and transported as glutamine and glutamate; levels of mRNA for genes involved in glutamine and glutamate synthesis (GLN2, GLU1) are accordingly induced by both light and sucrose. By contrast, light represses the synthesis of asparagine which therefore accumulates only in tissues of dark-adapted plants.

FIG. 4B. Levels of ASN1 mRNA are dramatically induced in dark-adapted plants, and this induction is repressed by light or by high levels of sucrose. Thus, under conditions of carbon limitation or nitrogen excess, plants activate genes for asparagine biosynthesis (Lam et al., 1995). The mRNA level of GDH was found to be under similar control (see also FIG. 3).

Figure 5:
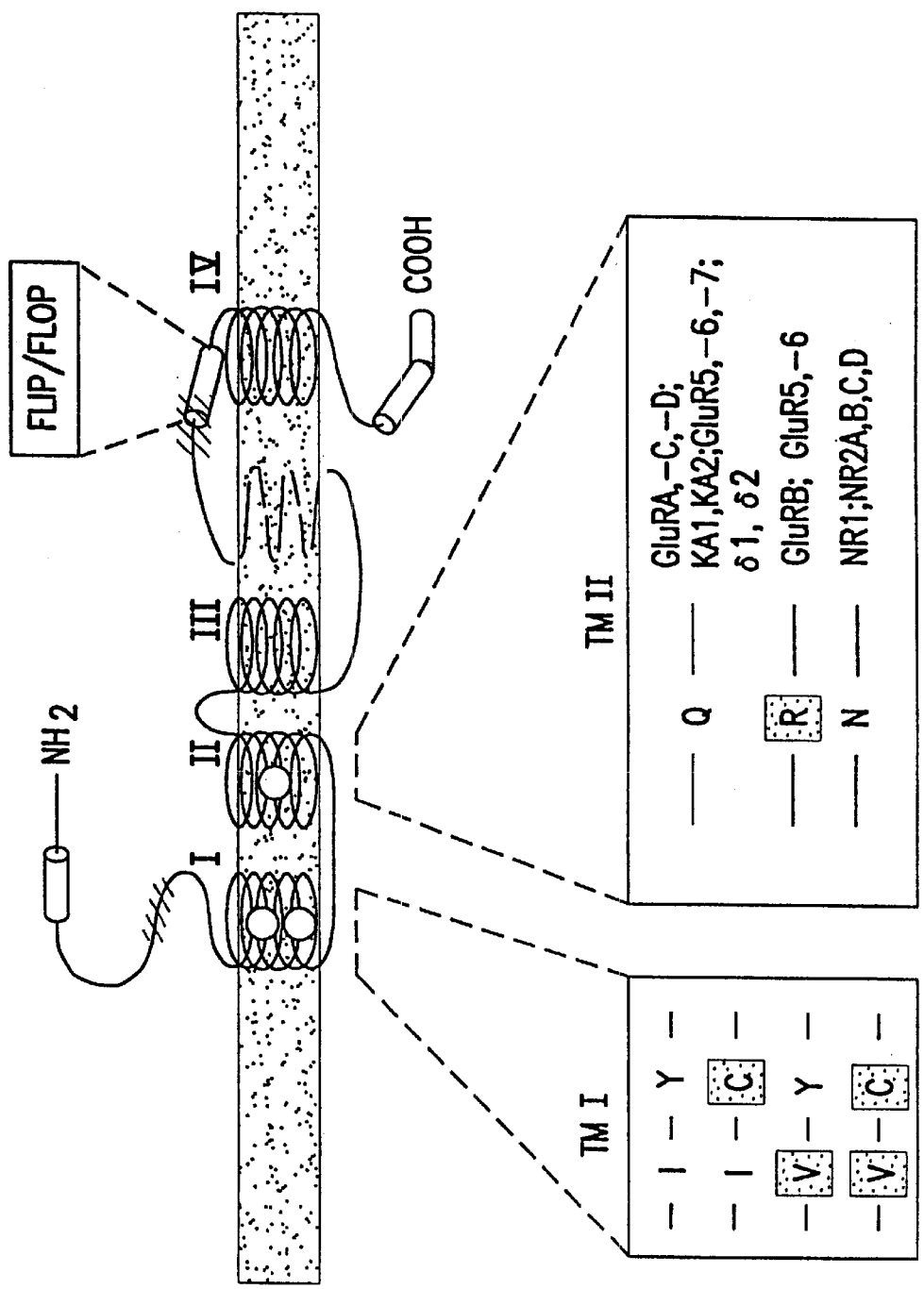

FIG. 5. Proposed Topology and Functional Domains of Ionotropic Glutamate Receptor Subunits Hydrophobicity plots of GluR subunit sequences predict four transmembrane (TM) segments (TM I–IV), depicted here hypothetically as a helices I–IV.

FIG. 6. Peptide Sequence Homology Between The Arabidopsis iGluR (SEQ ID NO1) and Animal iGluRs [E. coli GlnH:(SEQ ID NO:2); Chick KBP:(SEQ ID NO:3); Frog KBP;(SEQ ID NO:4); Rat GluR-K1: (SEQ ID NO:5); Rat GluR-K3:(SEQ ID NO:6); Rat GluR-K2:(SEQ ID NO:7)]

Peptide sequence analysis shows that the putative Arabidopsis iGluR contains a conserved glutamine binding domain which exists in all animal iGluRs.

FIG. 7A. Peptide sequence analysis shows the extensive homology between the putative Arabidopsis iGluR (SEQ ID NO:8) animal iGluRs. The region of homology extends from the glutamine binding domain into the transmembrane domains.

FIG. 7B. Peptide sequence analysis shows the extensive homology between the putative Arabidopsis mGluR and animal iGluR [NMDA:(SEQ ID NO:9); KA:(SEQ ID NO:10)]. The region of homology extends from the glutamate binding domain into the transmembrane domain.

FIG. 7C. Arabidopsis EST clones with low degree homology to glutamate binding domains. These EST clones have no homology to ionotropic nor metabotrobic GluR. Partial nucleotide sequence of EST clones are provided here [ATT50711:(SEQ ID NO:13); ATT52655:(SEQ ID NO:14; T20773:(SEQ ID NO:15)].

Figure 8:
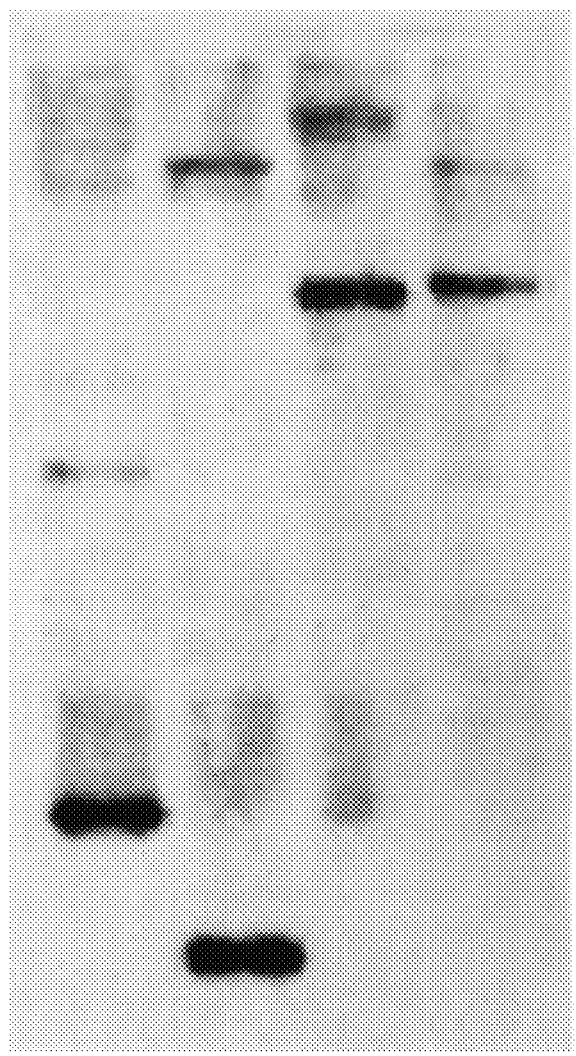

FIG. 8. Genomic Southern Analysis of Arabidopsis iGluR

Two μg of CsCl-purified Arabidopsis genomic DNA was digested with different restriction enzymes. Genomic Southern blot analyses were performed by running the digested DNA on a 1% (w/v) Tris-phosphate-EDTA agarose gel. The DNA was transferred to a nylon membrane after depurination, denaturation, and neutralization steps, followed by high-stringency hybridization with DIG-labeled probes which are generated by random-primed reactions (as described in the Boehringer-Mannheim Genius System User's Guide).

Figure 9:
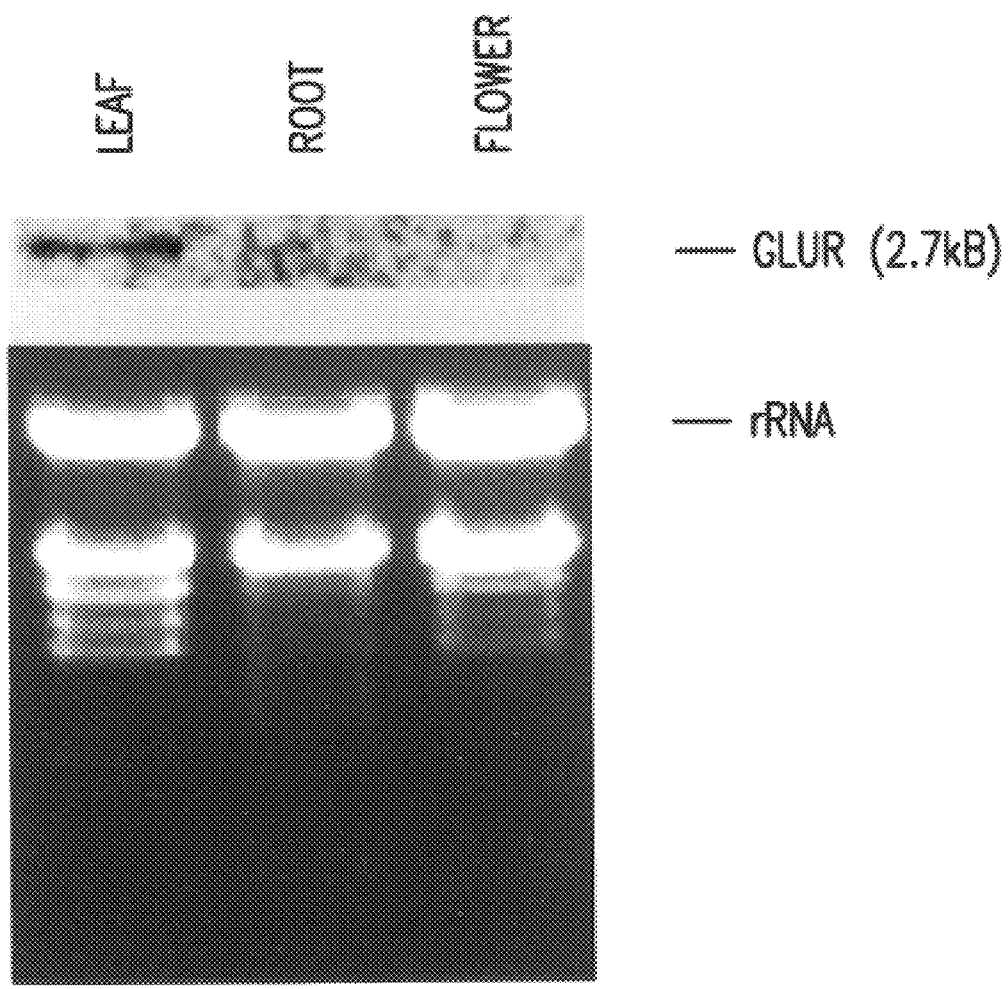

FIG. 9. Expression Of Arabidopsis iGluR In Different Tissues

Twenty μg of total RNA from each of the leaf, root, and flower tissues were run on a 1% formaldehyde agarose gel. Northern blot analyses were performed with high-stringency hybridization conditions at a temperature of 42° C. in 50% (v/v) formamide hybridization solution. Washing and chemiluminescent detection were performed according to the Boehringer-Mannheim Genius System User's Guide. The Northern shows that Arabidopsis iGluR mRNA is expressed predominantly in leaves and also at lower levels in roots and flowers of Arabidopsis.

Figure 10:
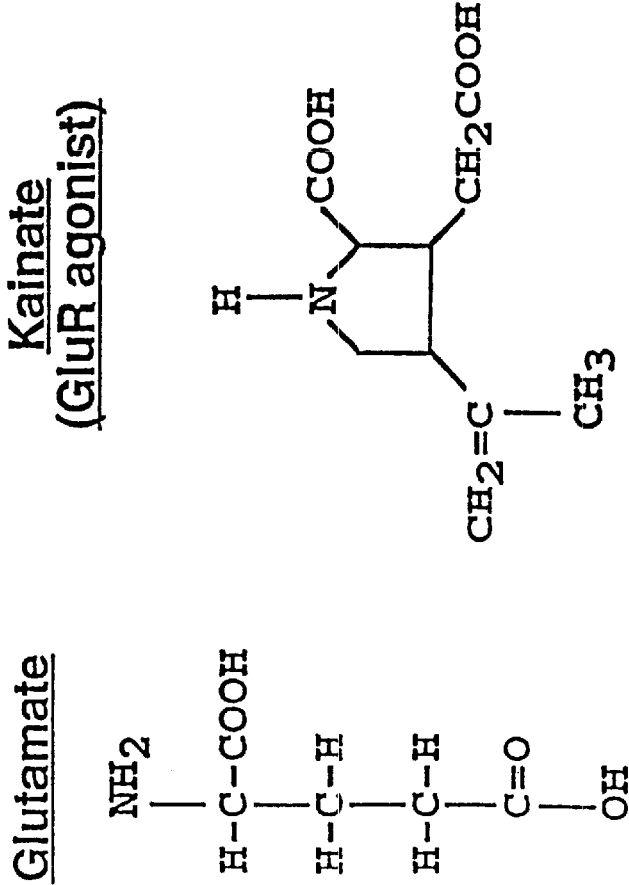

FIG. 10. Chemical Structures of Glutamate, Kainate, and DNQX

Figure 11A:
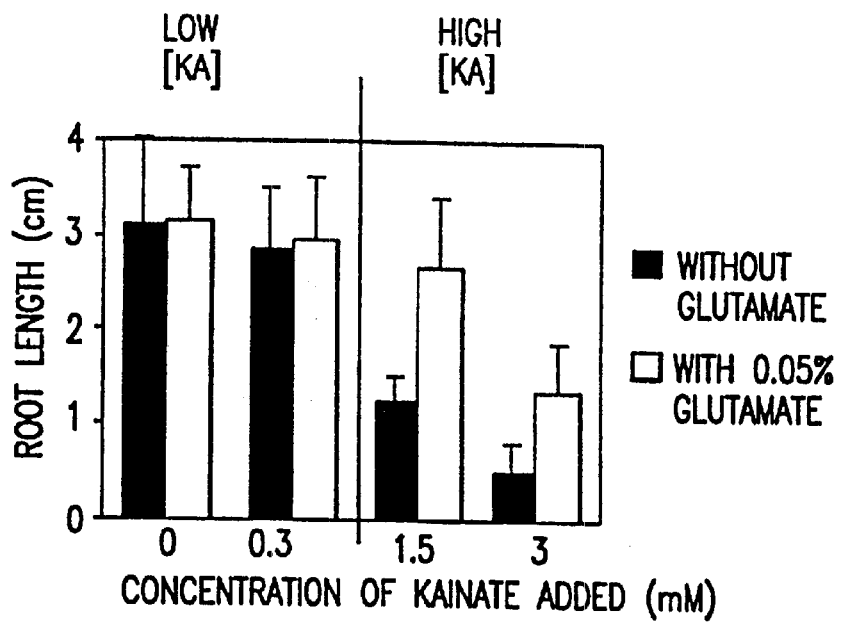
Figure 11B:
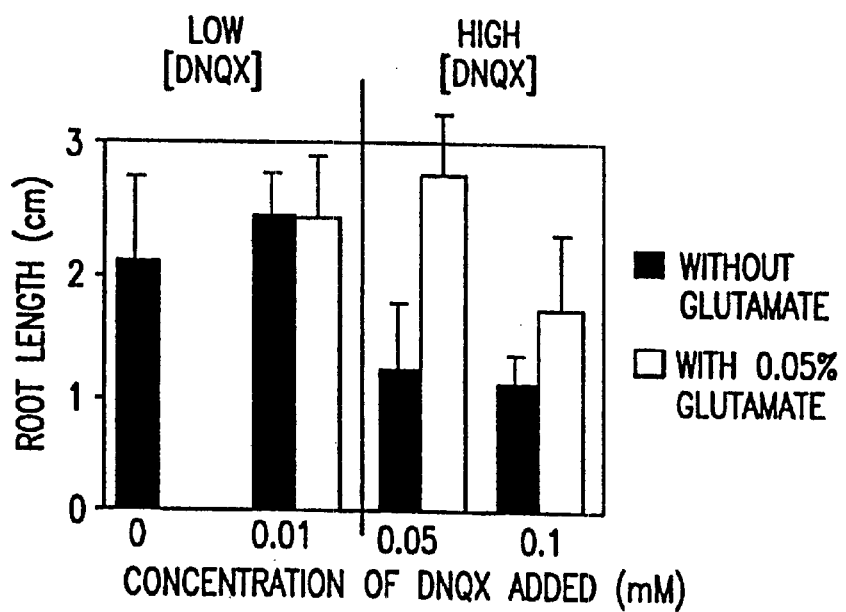

FIGS. 11A and 11B. Effects Of iGluR Agonist and On The Growth Of Arabidopsis

Arabidopsis seeds were grown on MS+3% sucrose vertical tissue culture plates containing various amounts of kainate (FIG. 11A) or DNQX (FIG. 11B), with (white bars) or without (black bars) glutamate supplementation. The effects of each drug on plant growth were assayed by measuring root length after two week. The results were discussed in text.

Figure 12A:
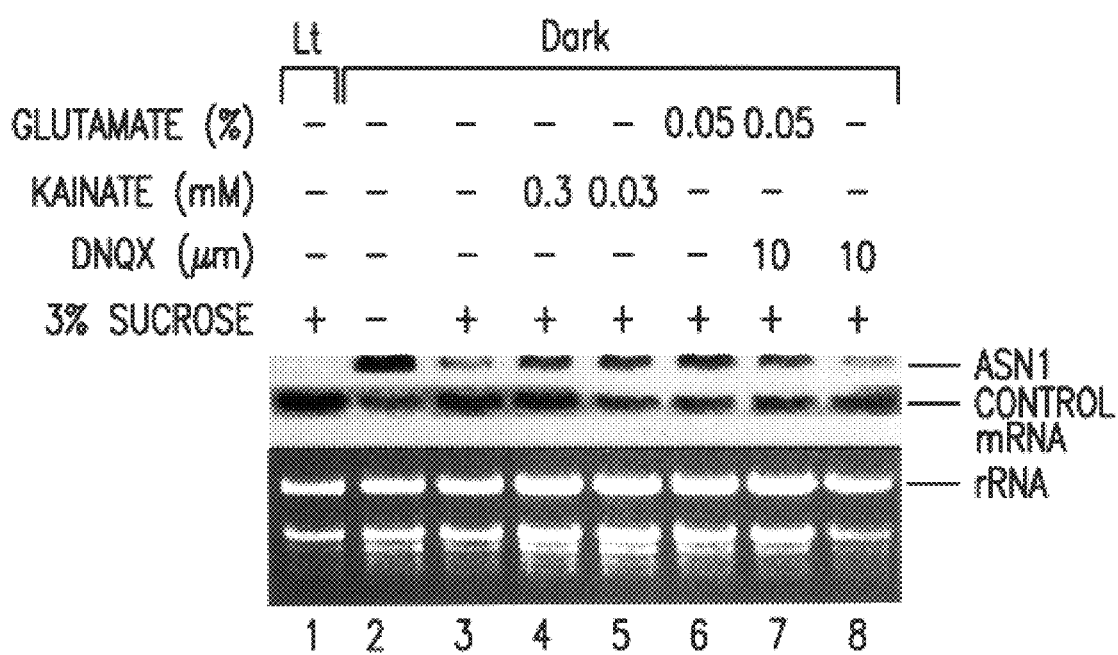
Figures 12B, 12C:
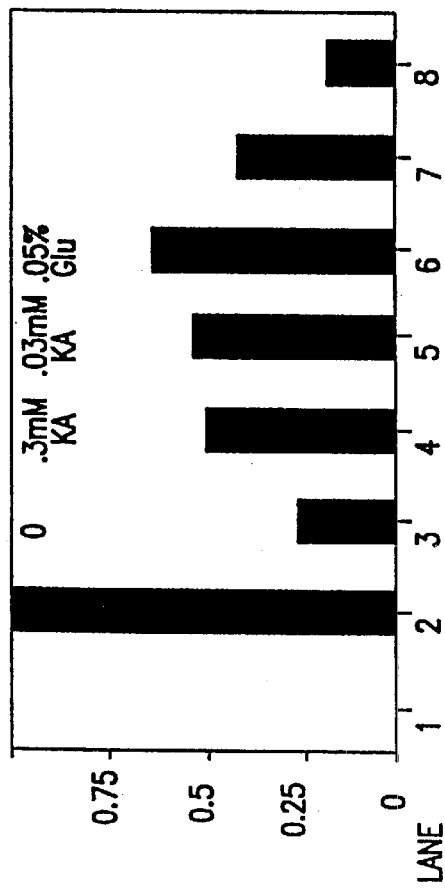

FIGS. 12A, 12B, 12C. Induction of Gene Expression by iGluR Agonist

FIG. 12A. Arabidopsis seeds were grown on plates containing MS medium plates 3% (w/v) Suc under 16-h light/ 8-h dark cycle for 2–3 weeks. The plants were then transferred to media described below and grown in complete darkness for 2 d. All samples containing 3% sucrose except for lane 2. MS was supplemented with kainate (lane 4:0.3 mM and lane 5:0.03 mM), 0.05% (w/v) glutamate (lanes 6 and 7), and 10 μM DNQX (lanes 7 and 8). The expression of ASN1 and a control gene were detected by northern analyses on duplicate blots (under high-stringency conditions in 50% [v/v] formamide-solution), 20 μg of total RNA was used for each lane.

FIG. 12B. Quantitation of the Northern blot results in (A) by densitometry scan.

FIG. 12C. Average folds of induction in two Northern lot experiments.

Figure 13A:
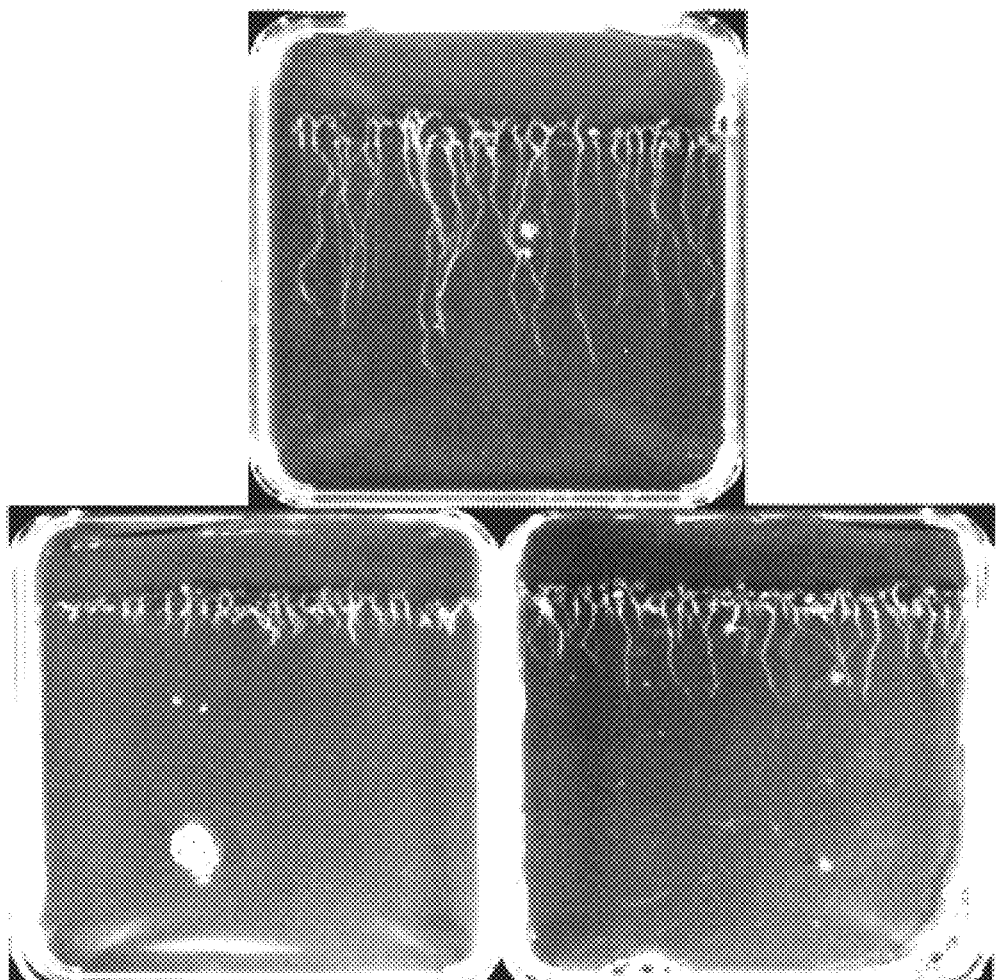
Figure 13B:
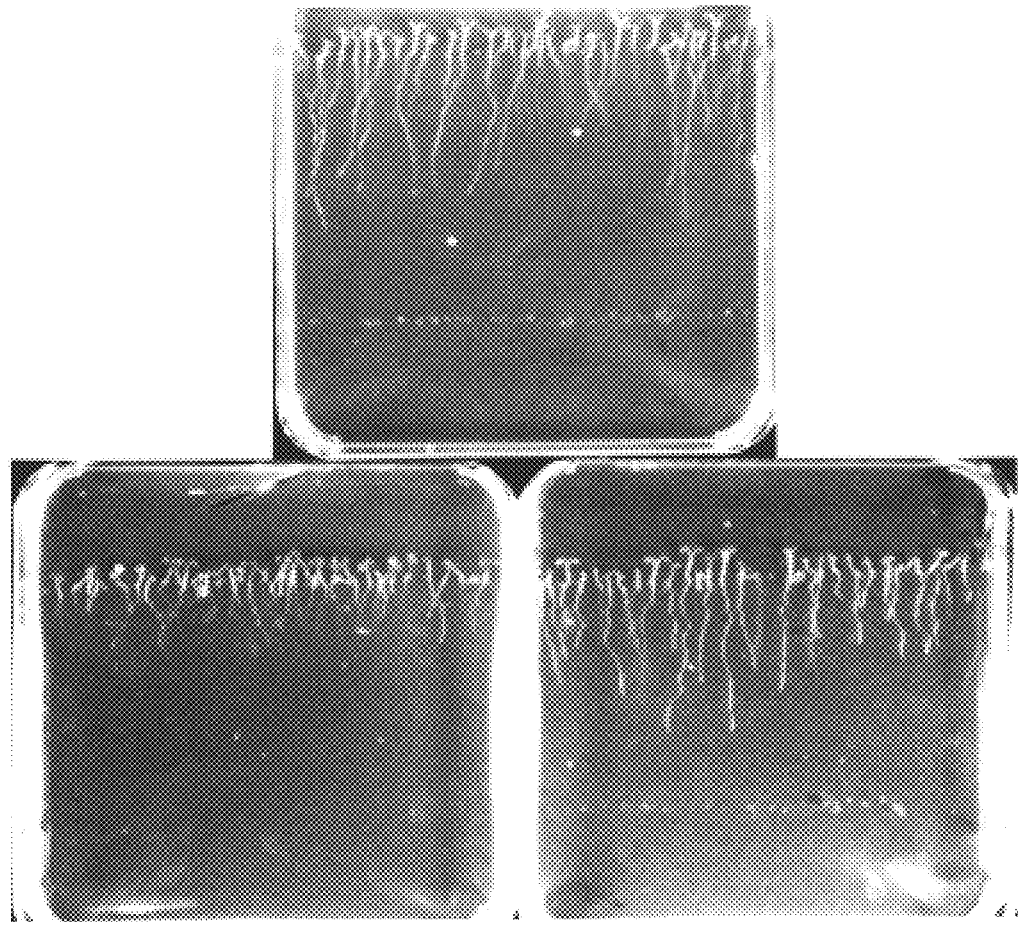

FIGS. 13A and 13B. Inhibition of Arabidopsis Growth by High Dosage of Kainate and DNQX Photographic representation of high dosage inhibitory effects of kainate and DNQX on the growth of Arabidopsis as described in FIG. 11.

Figure 14A:
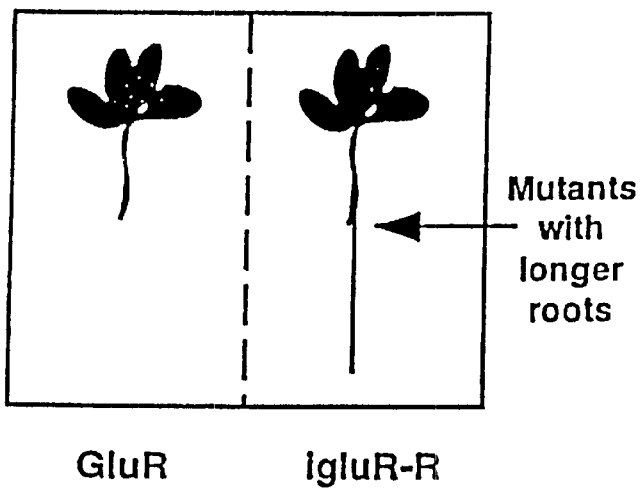
Figure 14B:
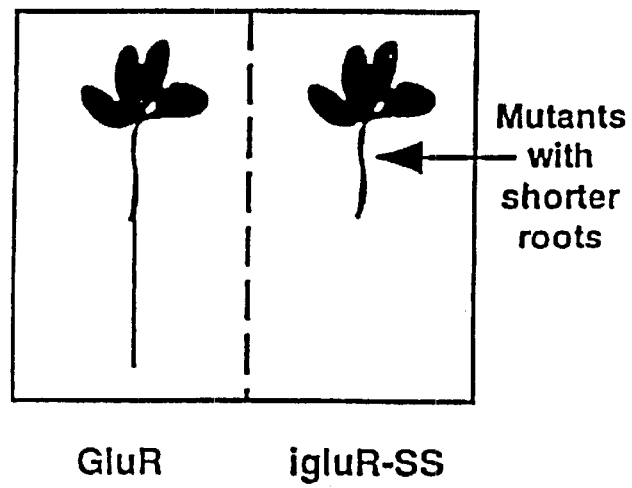

FIGS. 14A and 14B. Model Depicting Effects of Agonists and Antagonists on Plants Expressing Wildtype and Mutant GluR.

FIG. 15. Nucleotide and deduced amino acid sequence of full length Arabidopsis iGluR cDNA, called iGlr1. The regions of highest homology to animal iGluR are denoted in FIGS. 17 and 18.

The full-length Arabidopsis iGlr1 cDNA clone was constructed as follows: the partial EST cDNA clone 107M14T7 was used as a hybridization probe to isolate two additional iGlr cDNA clones (HM299 and HM262) from two different Arabidopsis cDNA libraries, KC-HM1 and CD4-7 (obtained from the Arabidopsis stock center, Ohio). Portions of each iGlr cDNA clone were annealed to generate a full-length Arabidopsis iGlr1 cDNA which was given the trivial name HM330.

Figure 16:
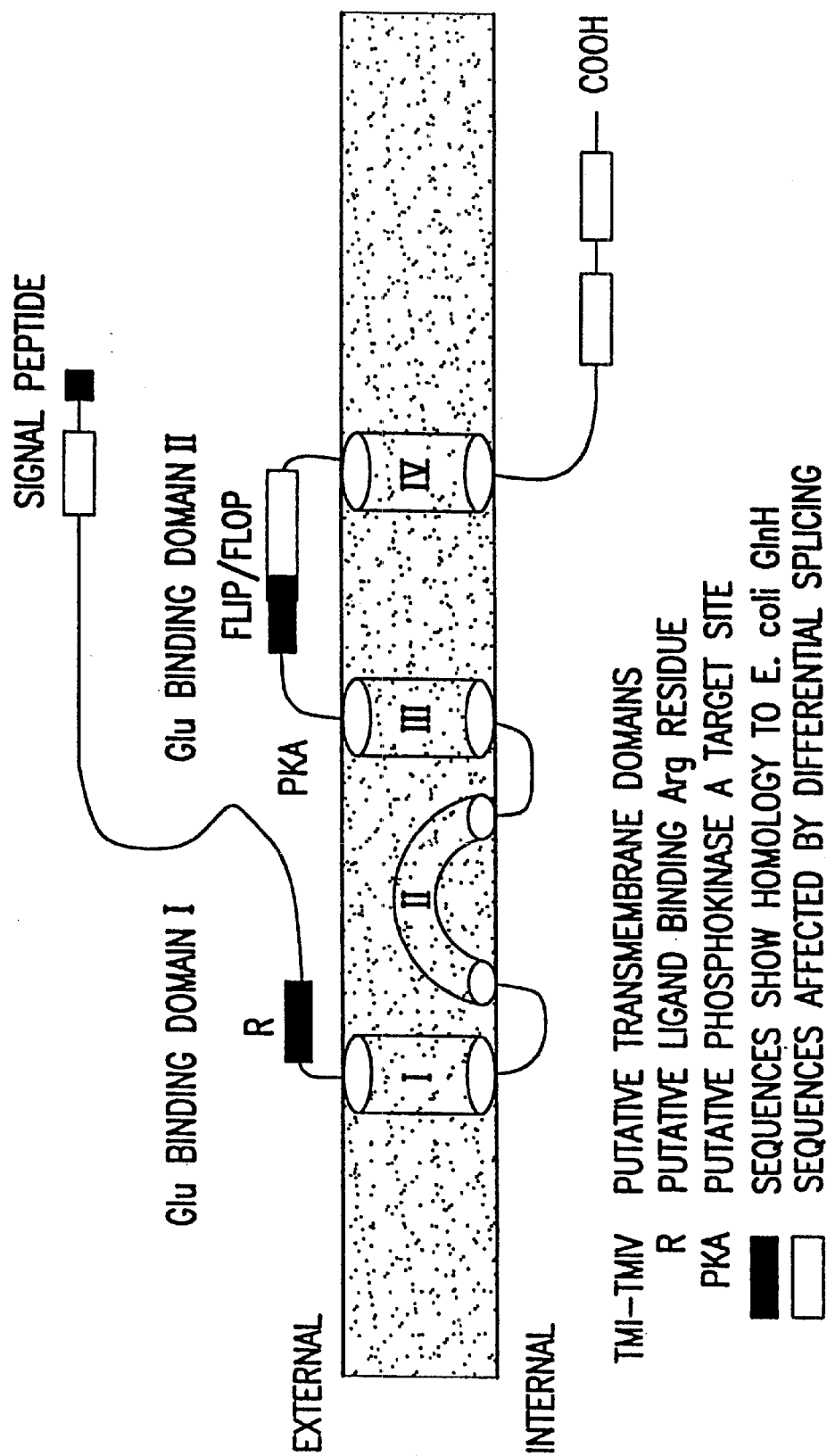

FIG. 16. Proposed membrane topology of iGluR receptors in animals. The model shows the important domains of animal iGluRs and their membrane topology. This figure is included as a reference, and does not include data generated in our lab. In addition to a signature 3+1 transmembrane topology, animal iGluRs contain two extracellular domains which are proposed to bind to glutamate. The two putative glutamate bindings domains have been previously shown to have homology to the E. coli glutamine permease gene (GlnH).

Figure 17:
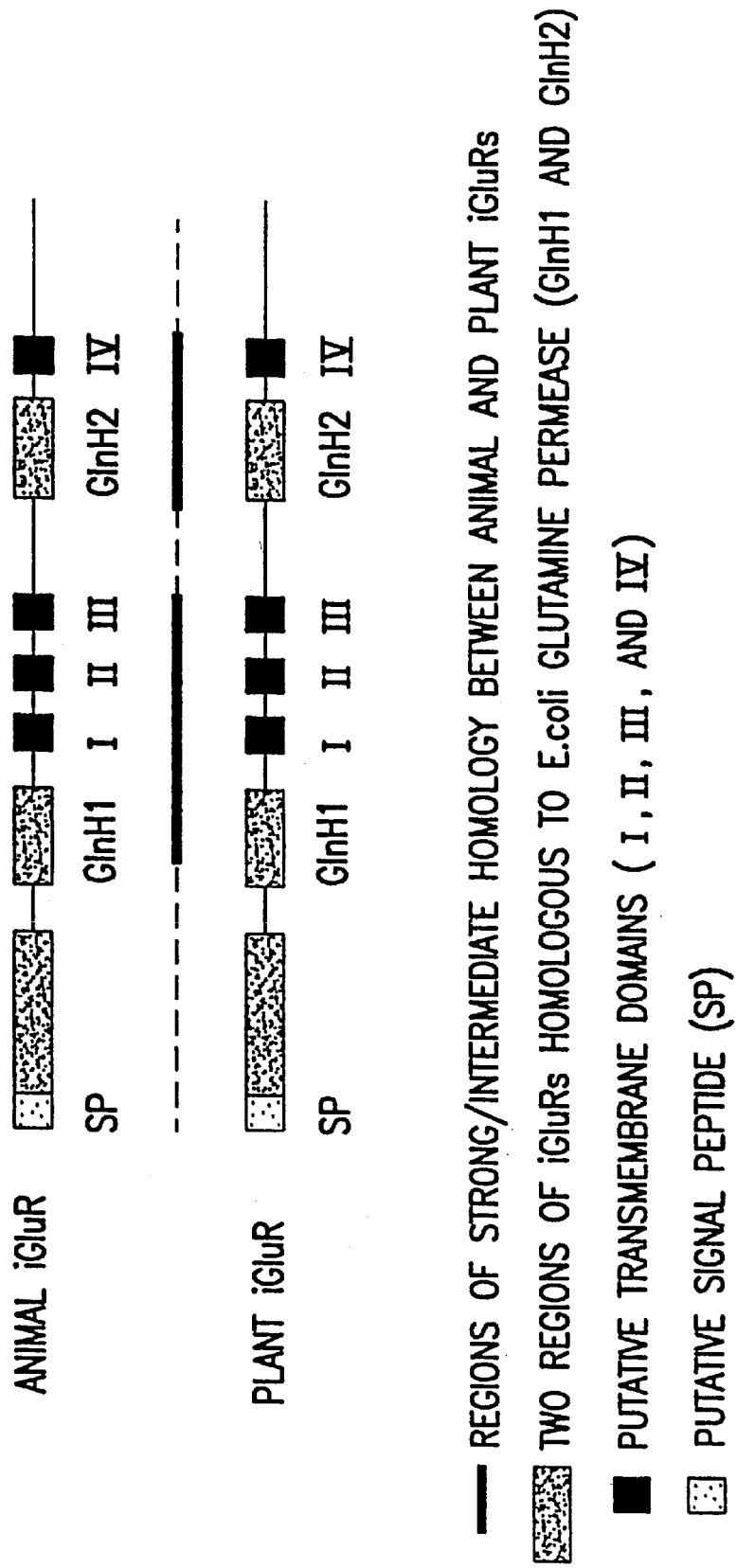

FIG. 17. Conserved domains between animal and Arabidopsis iGluR gene. The Arabidopsis iGlr1 cDNA encodes numerous conserved features of animal iGluRs including, 1. a signal peptide to direct it to the membrane (SP), 2. two putative glutamate-binding domains with homology to E. coli (GlnH1 and GlnH2), 3. Four transmembrane domains (TM I–IV). The amino acid sequences spanning the high homology region are shown in FIG. 4.

Figure 18:
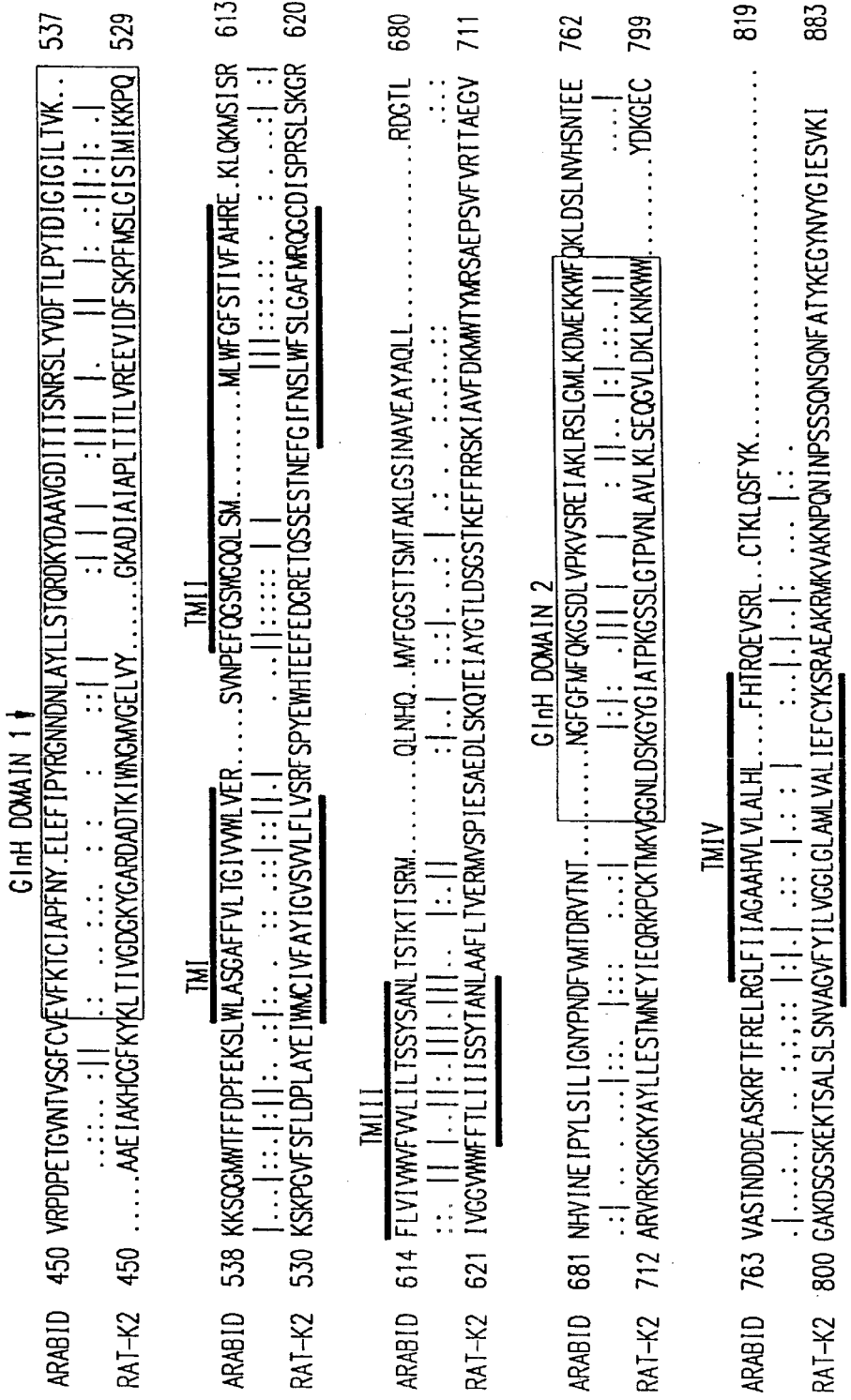

FIG. 18. Amino acid identities between Arabidopsis iGlr1 (SEQ ID NOS:26–27) and iGluR (SEQ ID NOS:28–31) gene of rat. Boxed are the GlnH1 and GlnH2 domains which show homology to E. coli glutamine permease (as defined in the animal sequence; see FIG. 17), the four transmembrane domains (TM I–IV). The arrow points to the conserved ligand-binding residue in the GlnH1 domain.

Figure 19:
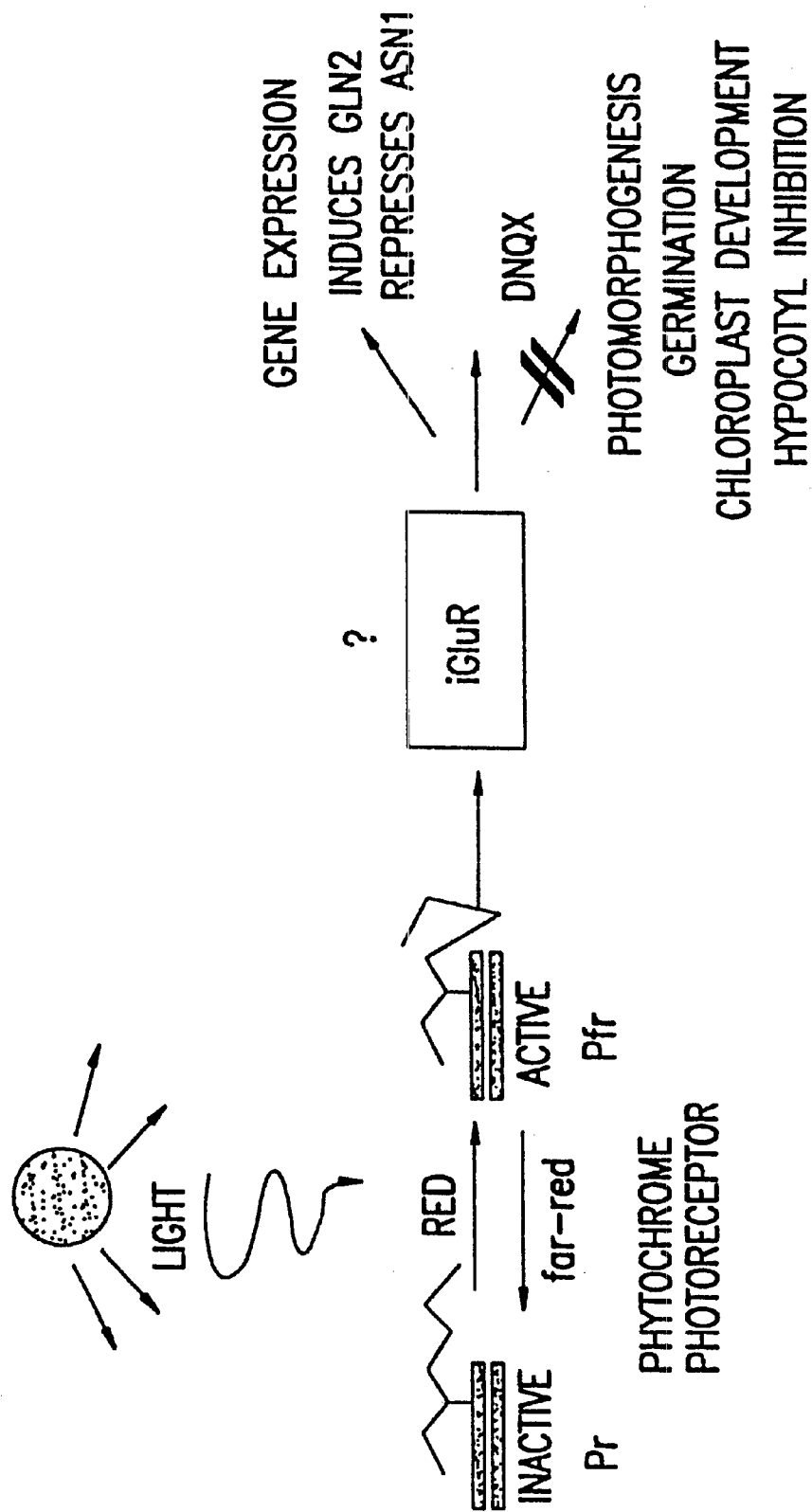

FIG. 19. A proposed role for plant iGluR in light signal transduction. We have shown that the iGluR antagonist DNQX and high concentrations of the iGluR agonist KA can block photomorphogenic processes such as germination, chloroplast development and hypocotyl elongation (see FIGS. 20–23). This model proposes a role for plant iGluR in the light signal transduction cascade.

Figure 20:
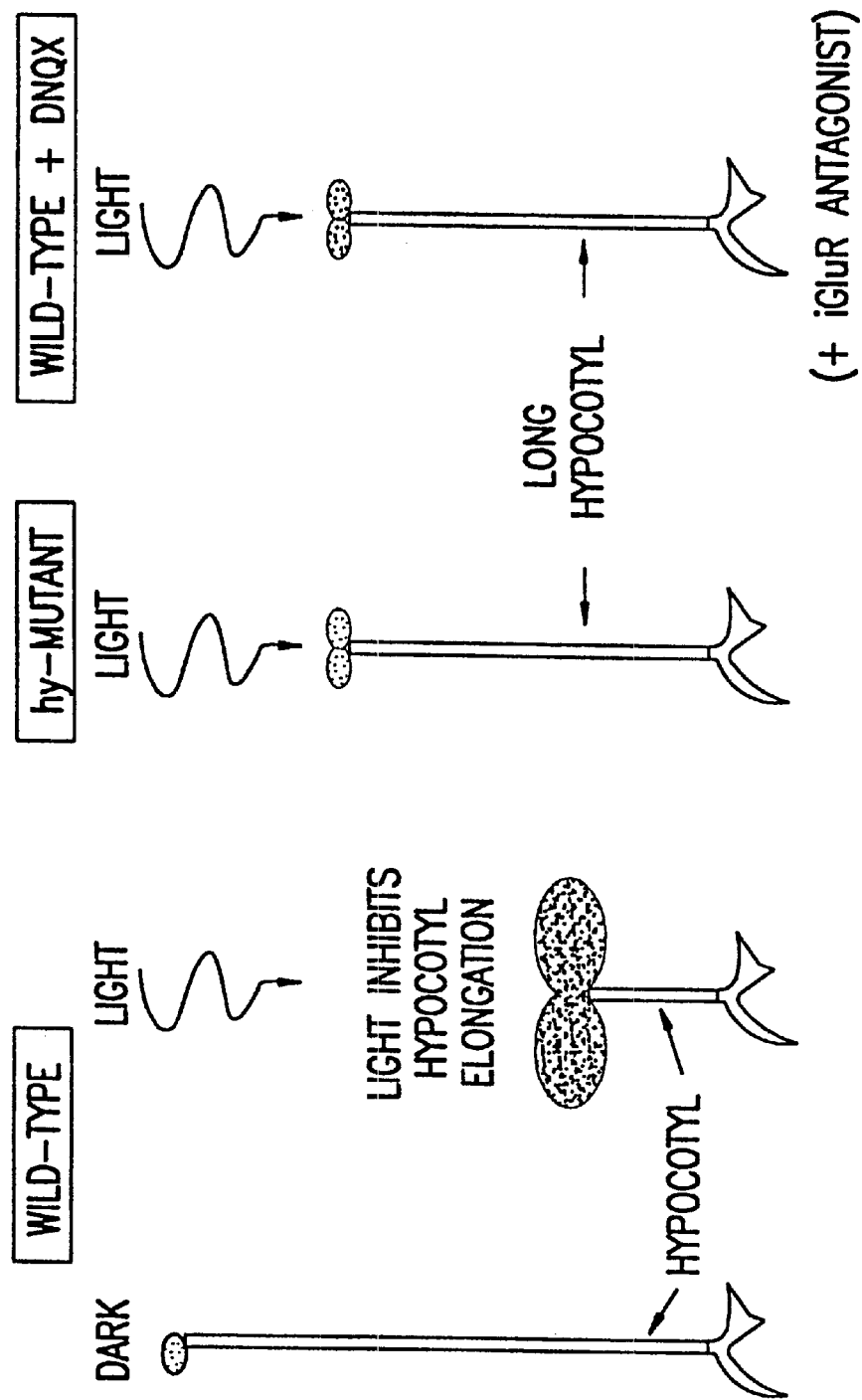

FIG. 20. iGluR antagonist DNQX phenocopies Arabidopsis long hypocotyl (hy) mutants impaired in light signal transduction. Light normally promotes greening and inhibits hypocotyl elongation in wild-type seedlings. hy mutants are impaired in light perception/signal transduction. hy mutants when grown in light take on the morphology of dark-grown seedlings (long hypocotyl). When wild-type plants are treated with DNQX, they grow as hy mutants (long hypocotyl).

Figure 21:
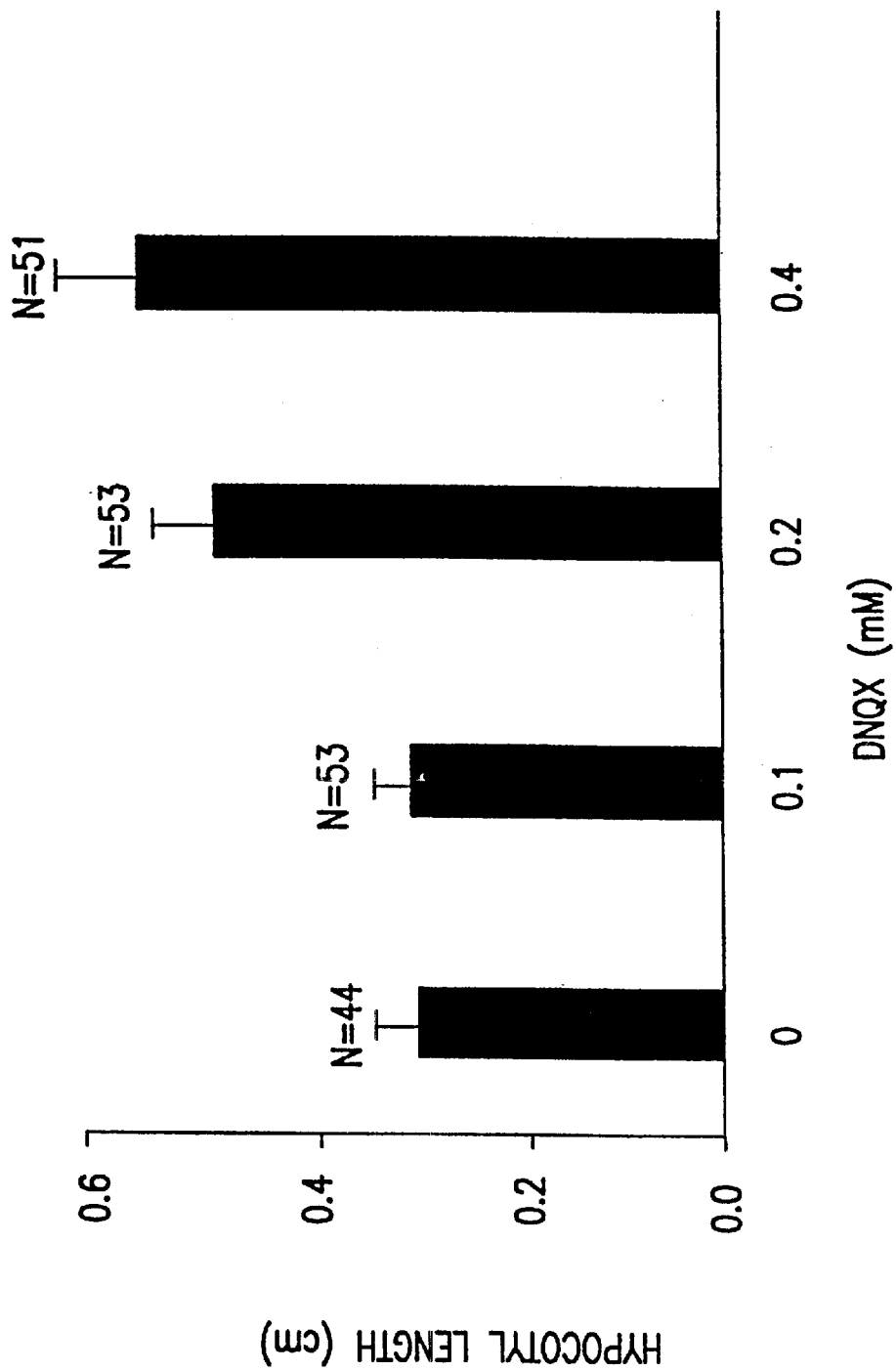

FIG. 21. DNQX has a significant effect on hypocotyl length in Arabidopsis. Increasing doses of DNQX (200 uM and 400 uM) cause significant increases in hypocotyl elongation in Arabidopsis. N=number of plants measured.

Figure 22:
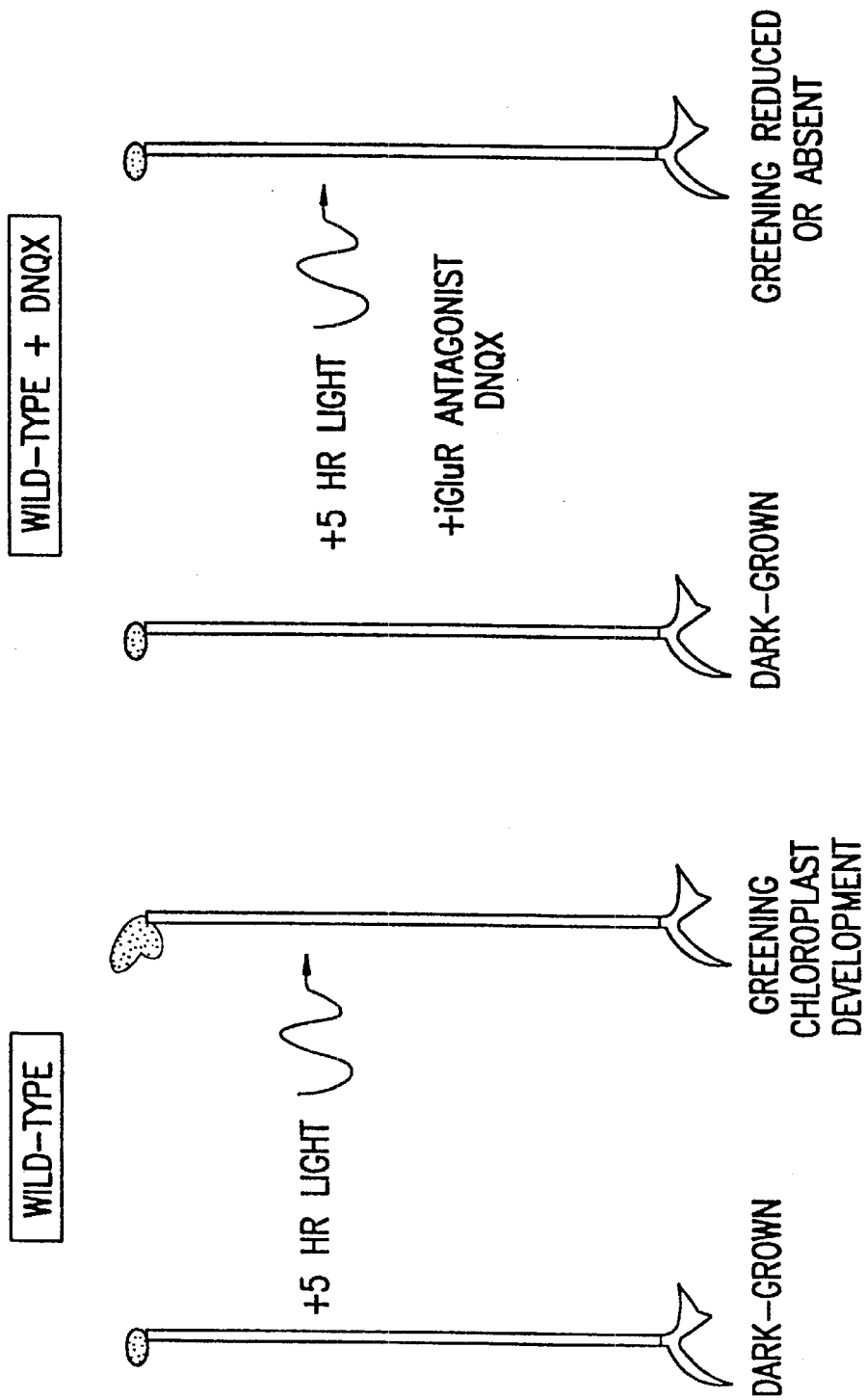

FIG. 22. DNQX, the iGluR antagonist blocks light-induced chloroplast development in Arabidopsis. Left panel. Plants grown in darkness have unopened yellow cotyledons. When these plants are exposed to light for 5 hrs, the cotyledons begin to green. If plants are grown in the dark with DNQX in the media, the cotyledons remain yellow and unopened after 5 hrs of light exposure. Thus, DNQX appears to block light-induced chloroplast development.

Figure 23:
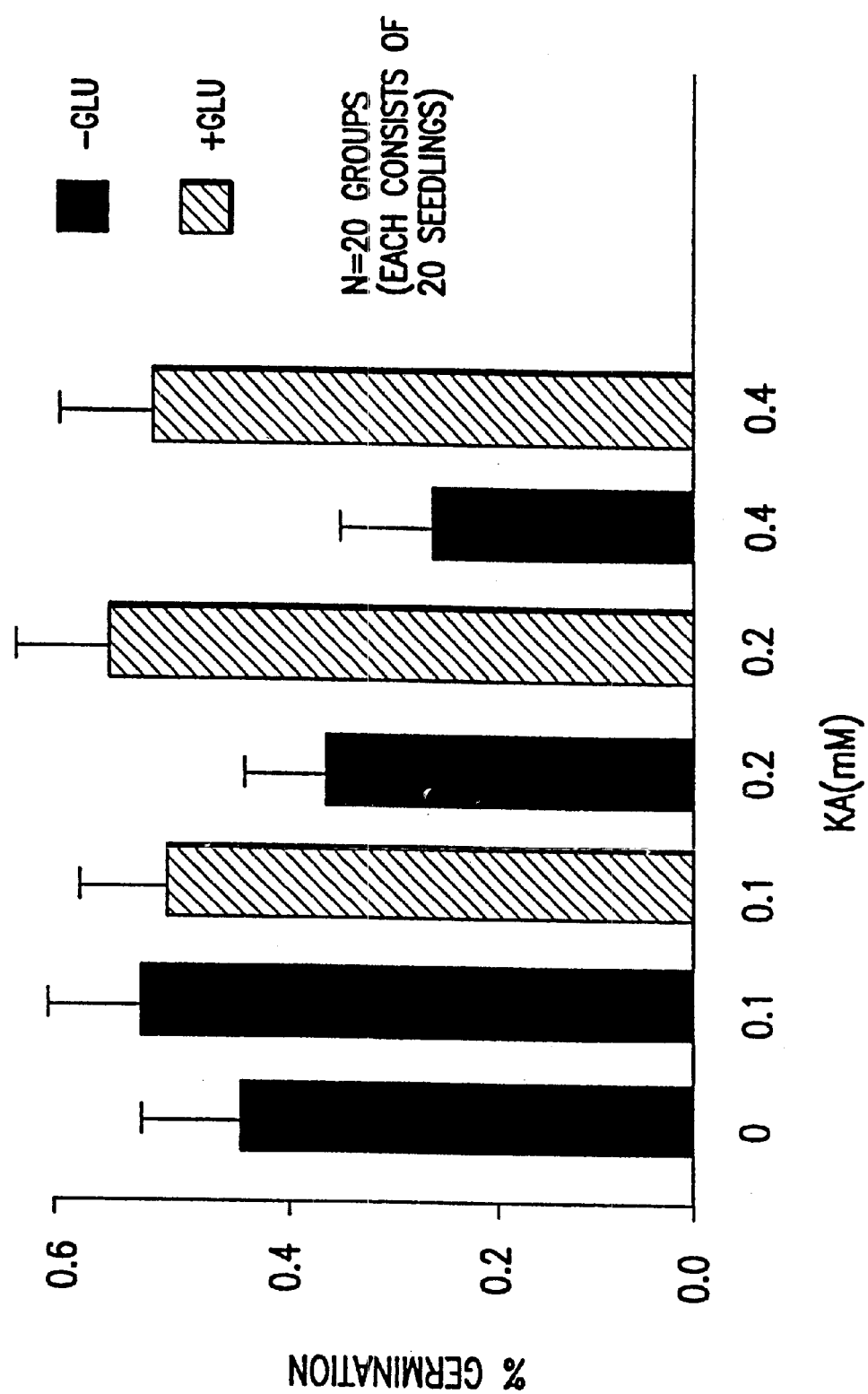

FIG. 23. Effects of kainate of germination of Arabidopsis in the dark. Arabidopsis seedlings germinated on media containing increasing amounts of kainate (200–400 uM) show a significant inhibition of germination of dark-grown seedlings. This inhibition of germination is likely to be specific to iGluR as it is specifically reversed by the supplementation of glutamate to the growth media.

Figure 24:
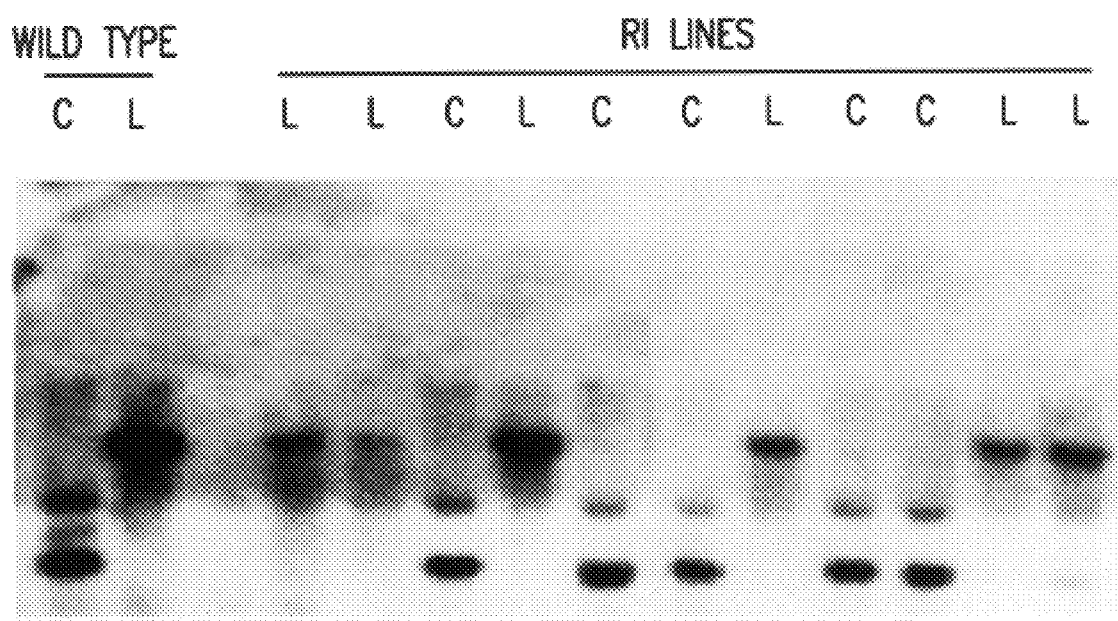

FIG. 24. The Arabidopsis iGlr1 gene was mapped using recombinant inbred lines of Arabidopsis. An RFLP for iGlr1 was identified in the wild-type Arabidopsis ecotypes Columbia (C) and Landsberg (L). This iGlr1-specific RFLP was used to identify the genotype of the iGlr1 gene in 30 Recombinant Inbred lines as being derived from the C or L parents. The "pattern" of inheritance of the iGlr1 gene in the recombinant inbred lines was compared to known markers and used to determine a map position (see FIG. 25).

Figure 25:
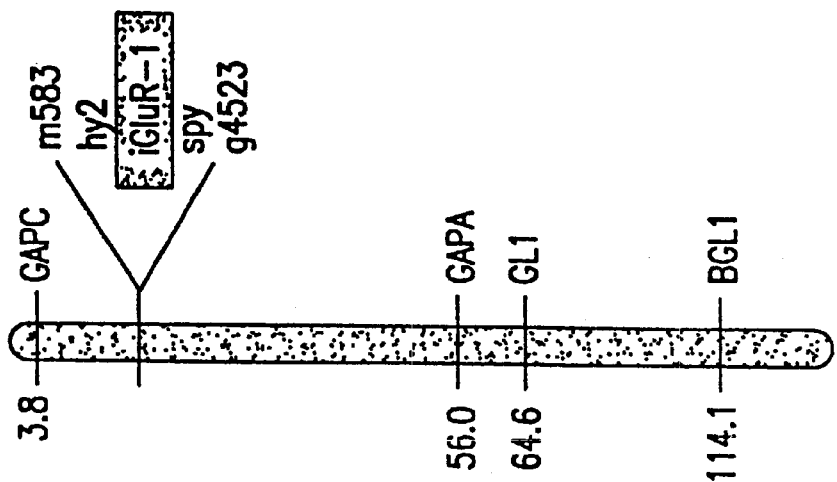

FIG. 25. iGlr1 maps to chromosome III to a similar position as two known mutants, hy2 and spy. Using data from recombinant inbred lines hy2 is a mutant impaired in light signal transduction (see review Whitelam & Harberd, Plant Cell Environment 1994, 17, 615–625). The spy mutant is impaired in GA hormone signal transduction (Jacobsen & Olszewski, 1993, Plant Cell 5, 887–896).

Figure 26A:
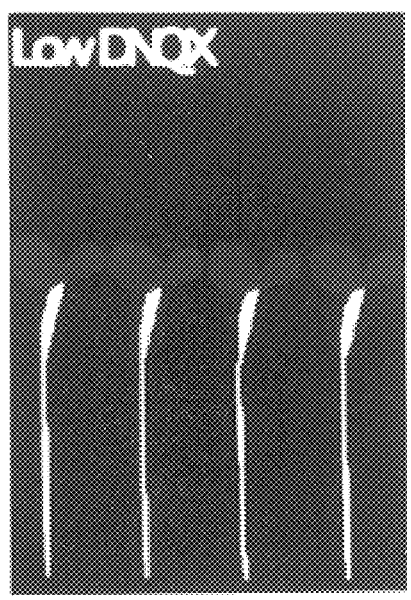
Figure 26B:
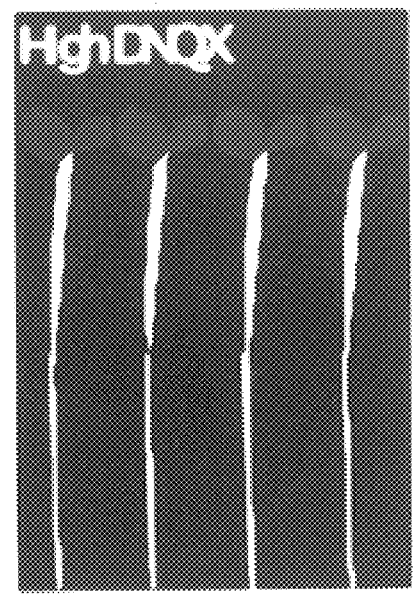
Figure 26C:
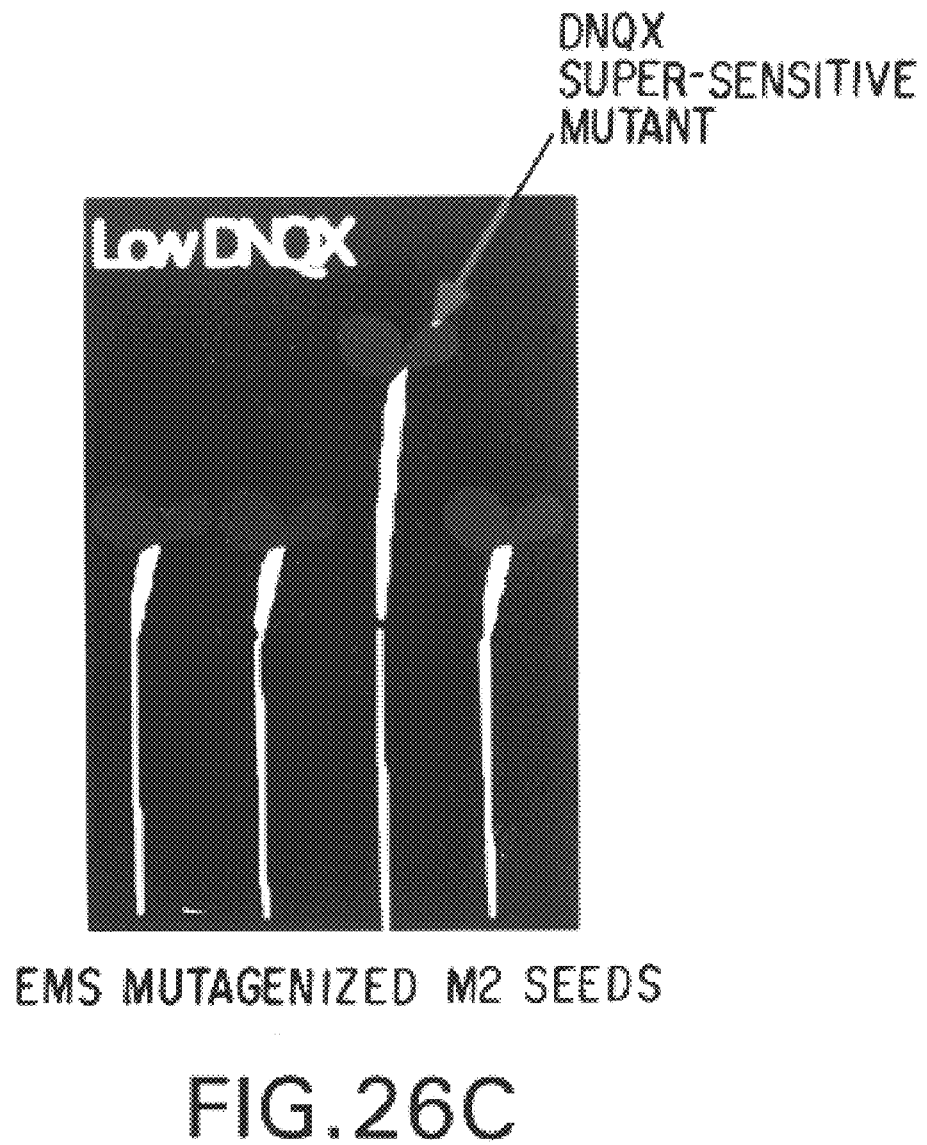

FIG. 26. Screen for Arabidopsis mutants with altered sensitivity to the iGluR antagonist DNQX. Mutants affected in iGluR can be used to test the in vivo function of plant iGluR and could also be mapped relative to the cloned gene. To isolate mutants in Arabidopsis iGluR we developed a screen for plants that are super-sensitive to the iGluR antagonist DNQX. Normally wild-type Arabidopsis only show an elongated hypocotyl phenotype when exposed to high doses of DNQX (200–400 μM) and show no hypocotyl elongation at low-concentrations (100 μM) (see FIG. 21). Therefore, ems mutagenized M2 seeds were germinated on media containing 100 uM DNQX and look for mutants that displayed an elongated hypocotyl at this low dose of DNQX.

Figure 27A:
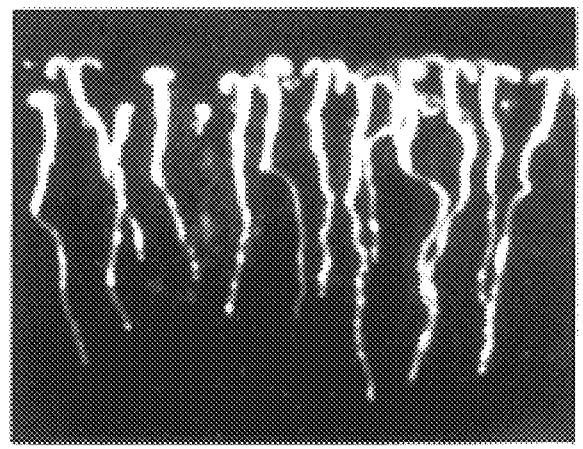
Figure 27B:
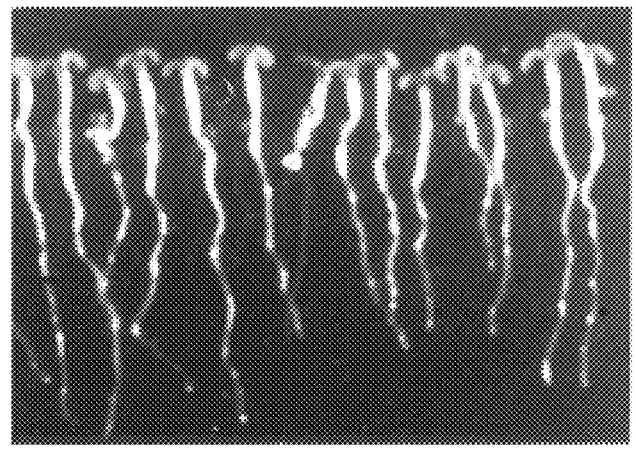
Figure 27C:
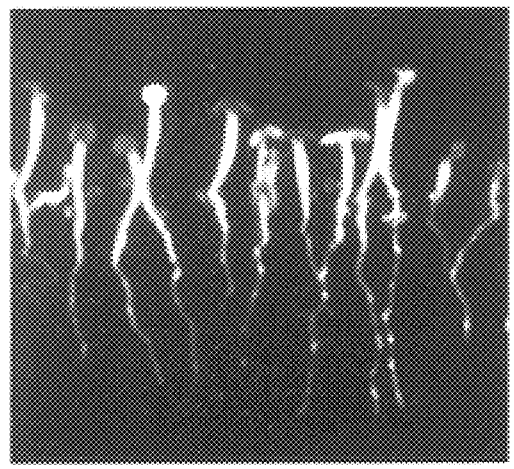
Figure 27D:
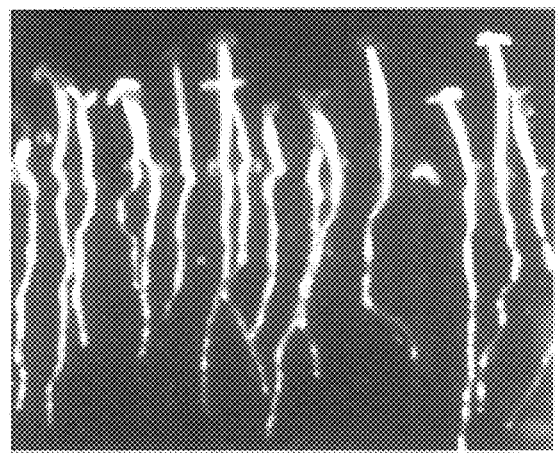

FIGS. 27A–D. Isolation of putative Arabidopsis mutants that are super-sensitive to the iGluR antagonist DNQX. Arabidopsis wild-type seedlings show no significant hypocotyl elongation when germinated on 100 uM DNQX (FIG. 27B) compared to control MS (FIG. 27A). By contrast, the putative DNQX supersensitive mutant shows an elongated hypocotyl when germinated on 100 uM DNQX (FIG. 27D). The putative super-sensitive mutant also shows an elongated hypocotyl compared to wild-type when germinated in the absence of DNQX (FIG. 27C). This is not unexpected that a mutation in iGluR would cause a phenotype of light-insensitivity.

Figure 28A:
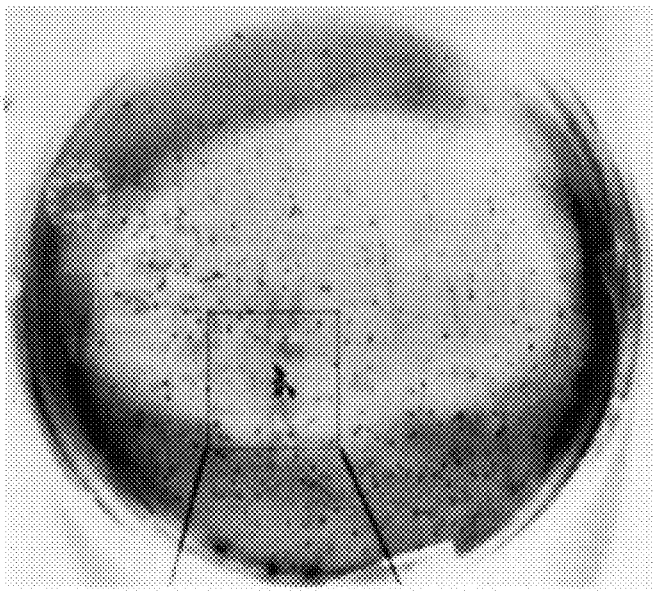
Figure 28B:
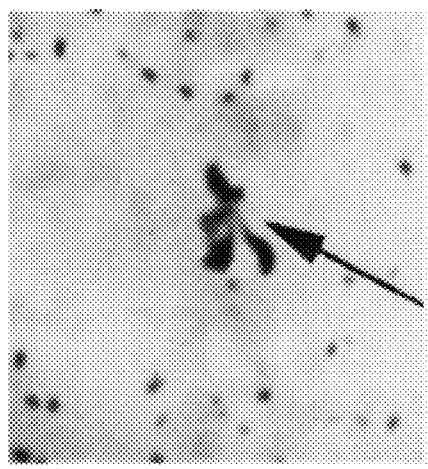

FIGS. 28A and 28B. Selection of Arabidopsis mutants resistant to the iGluR agonist Kainate. High doses of kainate (12 mM) kill wild-type seedlings. This is not unexpected as high doses of the iGluR agonist kainate function as a neurotoxin in animals. Arabidopsis mutants with putative defects in the KA binding site of iGluR were selected for the ability to grow in the presence of 12 mM kainate. FIG. 28A shows ems mutagenized Arabidopsis M2 seedlings sown on 12 mM kainate. Note the one KA-resistant plant is enlarged in FIG. 28B.

Figure 29A:
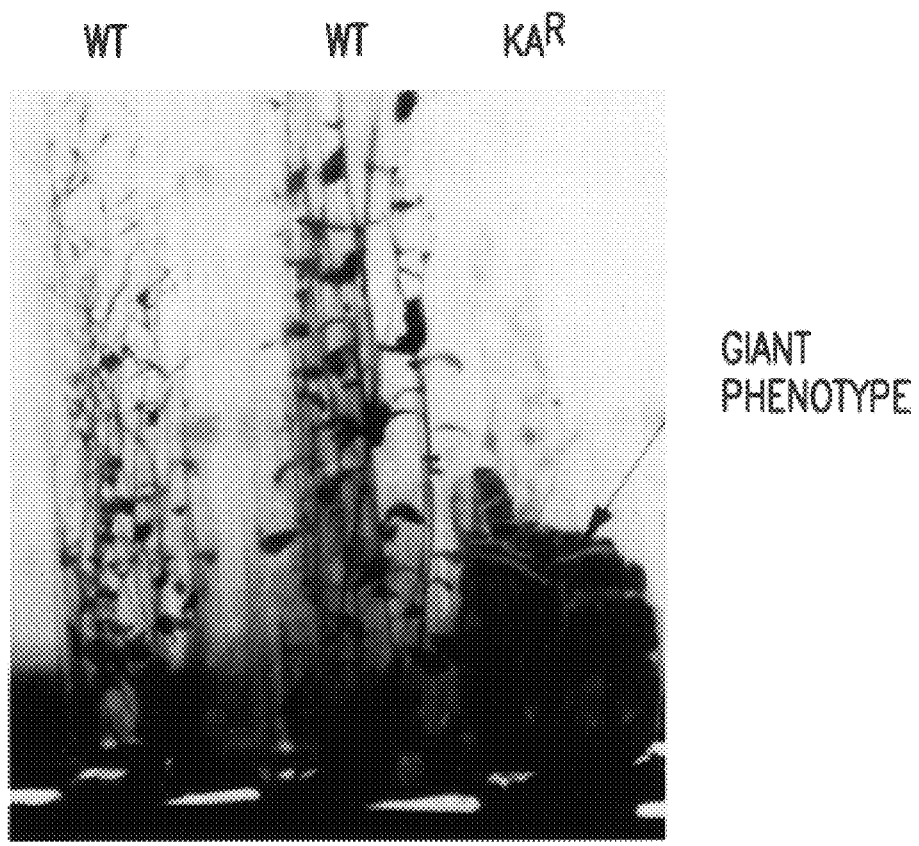
Figure 29B:
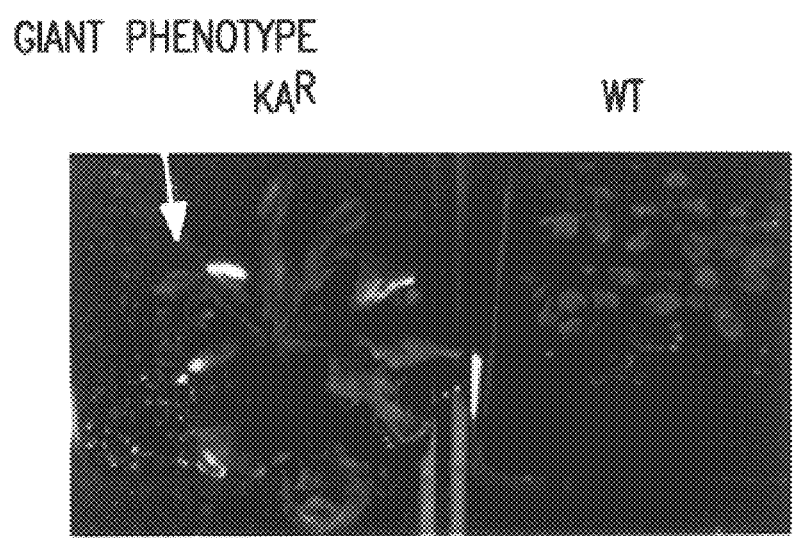

FIG. 29. Arabidopsis mutants resistant to the iGluR agonist kainate, display a Giant phenotype. Three independent Arabidopsis were mutants selected for growth on 12 mM KA (see FIG. 28). When the putative KA-resistant plants are transferred to soil, they each display varying degrees of a Giant vegetative phenotype. This result may indicate that iGluR affects/enhances overall plant growth.

Figure 30A:
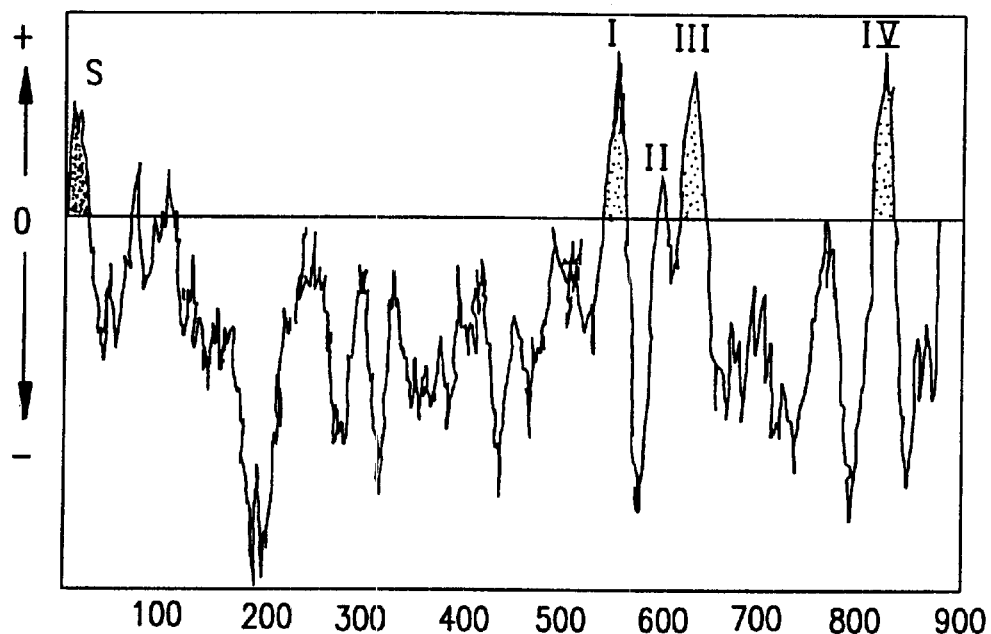
Figure 30B:
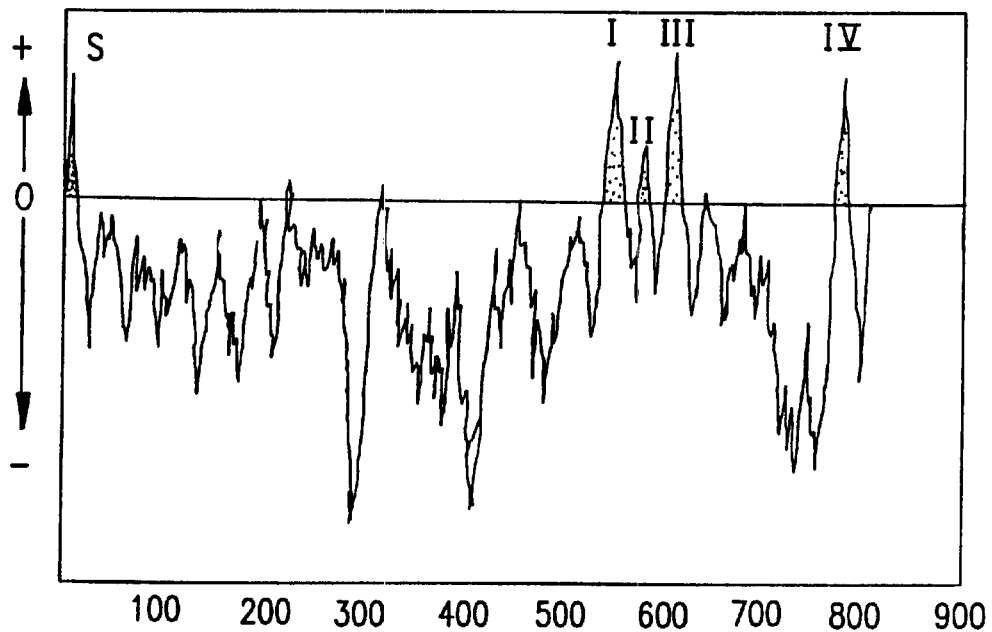

FIG. 30. Hydropathy plots of plant vs. animal iGluR. The hydropathy plot and prediction of transmembrane regions based on deduced primary sequence of rat iGluR K2 (upper panel) and Arabidopsis iGlr1 (lower panel) were performed with the program TMpred (K. Hofmann and W. Stoffel, TMbase—A database of membrane spanning proteins segments, Biol. Chem. Hoppe-Seyler 347,166 (1993)). Results showed that in both animal and plant iGluRs, there is a N-terminal signal peptide as well as a 3+1 transmembrane domain at the C-terminal region. These are structural features conserved in all iGluR genes.

Figure 31:
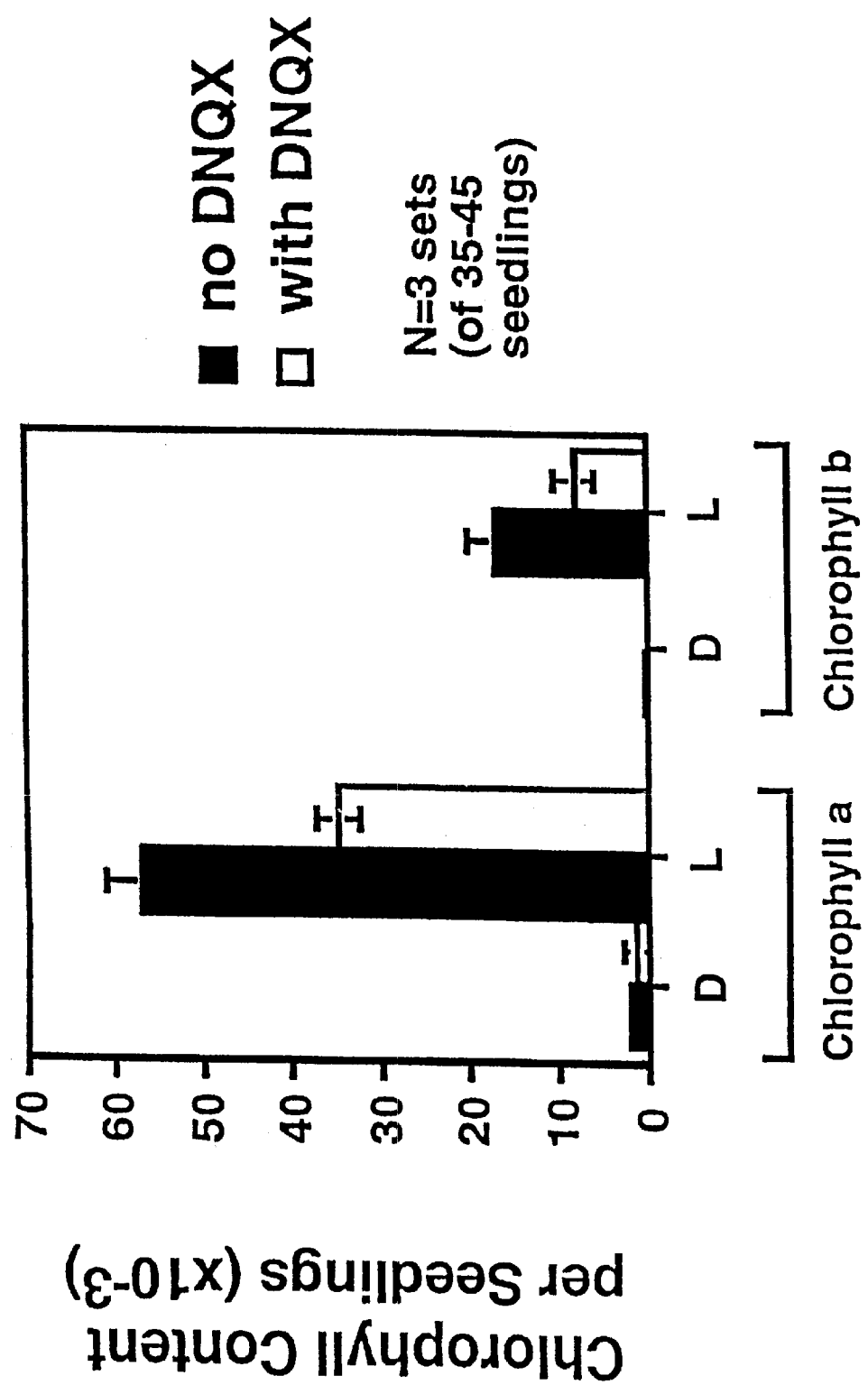

FIG. 31. Inhibitory effects of iGluR antagonist DNOX on light-induced chlorophyll synthesis in Arabidopsis. Seedlings were sown on MS+3% sucrose agar plates and grown in complete darkness (etiolated) for 5 days. On day 6, half of the seedlings were kept in the dark (D) and the other half were transferred to white light (L) for 7.5 hours. Levels of chlorphyll a and chlorophyll b were measured using the method by Moran (Plant Physiol. 1982, 69:1376–1381). The cotyledons of 30–40 plants were used for each data point. The results of each treatment were an average of three groups of plants. The error bars represent standard deviation. Black bar=no DNQX treatment. White bar=treatment with 0.4 mM DNQX. Treatment with DNQX resulted in a 30–35% reduction in light-induced chlorophyll synthesis.

Figure 32A:
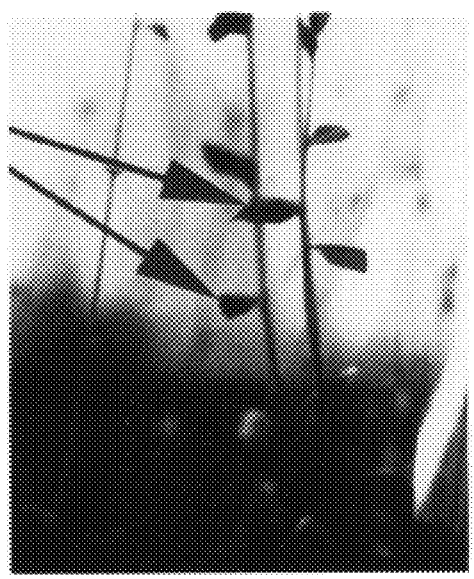
Figure 32B:

FIG. 32. Late flowering in KA-resistant "giant" mutants. Two independent KA-resistant mutants (KA-giant-1 and KA-Giant-2) show a giant, late flowering phenotype. Some of the cauline leaves from the flowering stalks of these KA-resistant giant mutants (panel B) display the morphology of rosette leaves in constrast to the normal morphology in wild type plants (panel A). These results suggest that iGluR may be involved in flowering and developmental processes.

Figure 33:
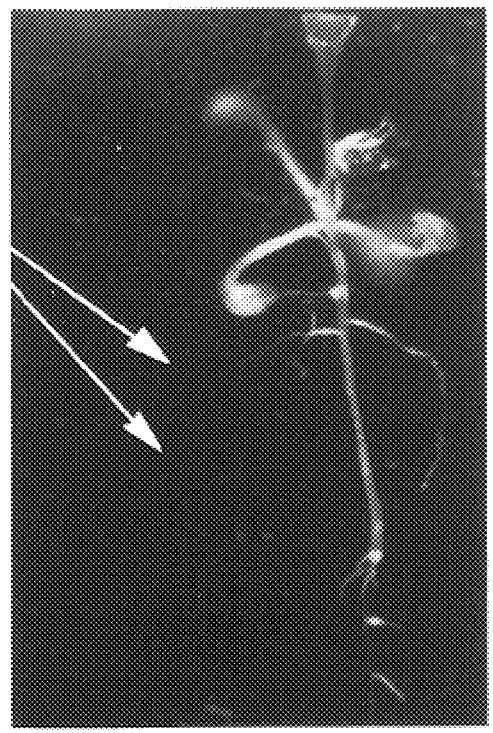

FIG. 33. Isolation of a homeotic mutant from the DNQX supersensitive screen. One DNXQ supersentitive mutant (0.1DNQX-10) showed a homeotic phenotype. Lateral roots emerged from the elongation hypocotyl of the plant (shown by the arrows). In wild type plants, lateral roots emerge only from roots.

5. DETAILED DESCRIPTION OF THE INVENTION

The present invention relates to a family of plant glutamate receptors, and glutamate-like receptors, the identification of compounds that modulate the activity of the plant GluR, and their use as plant growth regulators, including herbicides, or the identification of pharmaceutical agents used in animals, including man. The present invention is based, in part, on the discovery that glutamate may serve not only to transport nitrogen within a plant, but also act as a signaling molecule. A number of observations and discoveries described herein support the conclusion that the amino acids function as signaling molecules in plants. First, out of the 20 amino acids, only the amide amino acids, glutamate, glutamine, aspartate, and asparagine, accumulate to any significant levels as free amino acids in plant tissues, accounting for 64% of the total free amino acids in Arabidopsis leaves (FIG. 1). Second, out of the 20 amino acids only these four amide amino acids are found circulating within the plant vasculature to significant levels. Glutamate is the predominant amino acid transported within the phloem of light grown plants (FIG. 1 open bars). That glutamate may serve as a signaling molecule in plants is further supported by the fact that levels of free asparagine, glutamate, glutamine and aspartate are not static, but modulated by light. Glutamate levels are higher in the dark and low in the light (FIG. 1). In addition, the present invention is based on the discovery that glutamate, glutamine or asparagine each affects the expression of several nitrogen assimilatory genes in Arabidopsis (Lam et al., 1994, Plant Physiol. 106: 1347–1357; Vincentz et al., 1993, Plant J. 3:315–324). These amino acids have also been shown to affect the expression of genes involved in nitrate reduction to ammonia (Vincentz et al., 1993, The Plant Journal 3: 315–324).

The proposed role for glutamate is supported by the Applicants' identification of a full-length Arabidopsis cDNA, Glrl, that encodes a putative glutamate receptor most homologous to the iGluR class of animal glutamate receptors. The encoded GLrl protein contains all the characteristic features of ionotropic glutamate receptors (iGluR) including a signal peptide, two halves of the putative glutamate-binding domain and the three plus one transmembrane domains. Applicants have identified a family of iGluR genes in a variety of plants including Arabidopsis, dicots, legumes and monocots.

The proposed role for glutamate is supported by the identification of two Arabidopsis cDNAs with striking identity to iGluR and mGluR found previously only in the animal nervous system. The Applicants identified two cDNA clones each with identity to a distinct type of animal glutamate receptor. One Arabidopsis cDNA clone (EST#107M14T7, pAt-iGR-1) shares high identity to a class of glutamate receptors called ionotropic (iGluR) receptors which constitutes ligand-gated ion channels (Gasic, G. P. and Hollmann, 1992, Annu. Rev. Physiol. 54:507–536; Kanai et al., 1993, TINS 16:365–370; O'Hara et al., 1993, Neuron 11:41–52; Seeburg, 1993, TINS 16:359–365). In animals, binding of glutamate to membrane bound iGluR stimulates the influx of Ca++ resulting in and fast excitatory neurotransmission which will subsequently cause a wide variety of downstream responses (Gasic and Hollmann, 1992, Annu. Rev. Physiol. 54:507–536; Kanai et al., 1993, TINS 16:365–370; O'Hara et al., 1993, Neuron 11:41–52; Seeburg, 1993, TINS 16:359–365). For example, iGluRs may play a role in the activation of transcription factors such as c-fos and c-jun in primary neuronal cultures (Condorelli et al., 1993, J. Neurochem. 60:877–885; Condorelli et al., 1994, Neurochem. Res. 19:489–499).

The invention also relates to a second Arabidopsis cDNA (EST# 97C23T7, pAT-mGR-1) which shares identity to another class of animal glutamate receptors called metabotropic glutamate receptor, mGluR (Gasic and Hollmann, 1992, Annu. Rev. Physiol. 54:507–536). In animals, the mGluR class of glutamate receptors is coupled to a G protein that is linked to inositol phosphate/diacylglycerol formation which results in subsequent release of calcium from internal stores (Gasic, and Hollmann, 1992, Annu. Rev. Physiol. 54:507–536). In animals, mGluRs also have been reported to activate immediate early response genes, such as c-fos, c-jun, zif-268 (Condorelli et al., ibid).

The present invention is also based on the Applicants' discovery that in addition to possessing GluR genes, plants possess functional GluRs. The Arabidopsis iGluR cDNA (pAt-iGR-1) shows high identity to the animal GluR specifically activated by an iGluR agonist called kainic acid (KA). The plant iGluR is unique in that it has homology to both NMDA-type and KA-type GluR in animals. These kainate-selective iGluR receptors are competitively inhibited by an iGluR antagonist called 6,7-dinitroquinoxaline (DNQX). This iGluR agonist (KA) and antagonist (DNQX) are structurally distinct from glutamate (see FIG. 10), yet they bind to the iGluR receptor and stimulate or inhibit its action. Thus, any responses which these drugs may effect in plants, are likely to be due to their specific interaction with a iGluR-type receptor, rather than to general effects caused by inhibition of glutamate-utilizing enzymes. This iGluR agonist/antagonist pair can specifically affect the expression of nitrogen metabolic genes in Arabidopsis.

That plants possess a functional GluR is further supported by Applicants' discovery that specific iGluR against, KA, inhibits plant growth and this inhibition can at least partially be reversed by glutamate. A specific iGluR antagonist, DNQX, is able to phenocopy Arabidopsis mutants impaired in light and/or hormone signal transduction. These data combined strongly suggest that plant iGluRs are involved in plant signal transduction and may be involved in more than one signal transduction pathway.

The invention also relates to the use of the plant GluR as a target to select for new herbicides. The cloned plant GluR described herein can be utilized for the selection of new plant specific herbicides. Glumate analogs, such as L-methionine-S-sulfoximine (MSO) and phosphonothricin (PPT), are effective herbicides. MSO and PPT may be herbicides acting not only through target enzymes, but also through GluR.

As shown in the working examples, infra the present invention also provides methods of screening and identifying novel plant growth regulators and pharmaceutical drugs that mimic or antagonize glutamate in regulating plant metabolism, physiology and/or gene expression. The novel plant growth regulators may have structural homology to agonists or antagonists of animal glutamate receptors. Such agonists and antagonists have uses as stimulatory or inhibiting plant growth regulators. Due to their structural homologies with animal glutamate receptors, plant glutamate receptors proteins and polypeptides can also be used in in vitro screening for drugs that act on animal glutamate receptors.

The methods of identifying these novel plant growth regulators are based on in vivo screening of chemicals for their abilities to alter plant growth, development or gene expression in a manner that can be reversed or enhanced by glutamate or glutamate-antagonists.

In other embodiments, the methods are based on in vitro screening of chemicals for their abilities to compete or interfere with glutamate binding of plant or animal GluR.

The present invention also encompasses the use of the cDNA clones of the plant GluR to not only select for new herbicides, but to also genetically engineer herbicide resistant plants. Given that glutamate acts as an important signal for growth and development, the invention also encompasses modulating the activity of the iGluR and mGluR to alter growth and development patterns of the plants by techniques such as transgenic plants. Therefore gene constructs encoding the plant glutamate receptor protein and polypeptides can be used in genetic engineering of plants to improve their agronomic or industrial properties.

The present invention also encompasses the use of plant iGluR mutants to screen for new drugs affecting the central nervous system (CNS) in humans. Agonists and antagonists of iGluR receptors in animals are used as drugs for treating CNS disorders such as Epilepsy, stroke, dementia and CNS trauma. Arabidopsis mutants super-sensitive to mammalian iGluR agonists or antagonists could potentially be used to screen for new drugs to treat these types of neurodegenerative diseases in humans.

5.1. The Plant Glutamate Receptor Gene

The present invention encompasses the nucleotide coding sequence encoding plant GluR proteins and polypeptides. These nucleotide sequences were identified in Arabidopsis and shown to have homology to the animal glutamate receptor genes, iGluR and mGluR. Additional nucleotide sequences were identified in Arabidopsis as having a low degree of homology to the glutamate binding domain of the glutamate receptor, which are neither ionotropic nor metabotrobic, are also described herein. In a specific embodiment described herein, the plant GluR genes were identified by searching the Arabidopsis Expressed Sequence Taq (EST) databand (Newman et al., 1994, Plant Physiol. 106: 1241–1255) for cDNAs with identity to the glutamate receptor of animals. The five EST clones that are identified in the present invention were not previously known to contain a high enough degree of homology to animal glutamate receptors to be identified as such in the Genebank. In the present invention the five EST clones were identified as potential glutamate receptors due to sequence homology and then further characterized as such as described below.

The cDNA sequence and the deduced amirio acid sequence that encodes a plant glutamate receptor most homologous to the iGluR class of animal glutamate receptors are shown in FIG. 15.

The invention includes nucleic acid One Arabidopsis cDNA clone (EST#107M14T7, pAt-iGR-1) shares high identity to a class of glutamate receptors called ionotropic (iGluR) receptors which constitutes ligand-gated ion channels (Gasic and Hollmann, 1992, Annu. Rev. Physiol. 54:507–536; Kanai et al., 1993, TINS 16:365–370; O'Hara et al., 1993, Neuron 11:41–52; Seeburg, 1995, TINS 16:359–365). In animals, binding of glutamate to membrane bound iGluR stimulates the influx of Ca++ resulting in and fast excitatory neurotransmission which will subsequently cause a wide variety of downstream responses (Gasic and Hollmann, 1992, Annu. Rev. Physiol. 54:507–536; Kanai et al., 1993, TINS 16:365–370; O'Hara et al., 1993, Neuron 11:41–52; Seeburg, 1995, TINS 16:359–365).

A second Arabidopsis cDNA (EST# 97C23T7, pAT-mGR-1) shares identity to another class of animal glutamate receptors called metabotropic glutamate receptor, mGluR (Gasic and Hollmann, 1992, Annu. Rev. Physiol. 54:507–536). In animals, the mGluR class of glutamate receptors is coupled to a G protein that is linked to inositol phosphate/diacylglycerol formation which results in subsequent release of calcium from internal stores (Gasic and Hollmann, 1992, Annu. Rev. Physiol. 54:507–536).

Three additional clones (EST# T20773, EST# ATT50711, EST# ATS2655) were identified in Arabidopsis as having a low degree of homology to the glutamate binding domain of the animal glutamate receptor. However, these clones do not correspond to ionotropic nor metabotropic animal GluRs. Therefore these clones may represent a novel class of glutamate-like receptors in plants. The plant GluR of the present invention span the plant cellular membrane, as well as intracellular membranes including vacuolar membranes, chloroplast membranes and mitochondrial membranes.

The Arabidopsis iGluR cDNA, pAt-iGR-1, shares extensive identity with animal iGluRs. The plant GluR is unique in that it has homology to both NMDA-type and KA-type GluR in animals. About 700 nucleotides from the 5' end of the clone pAt-iGR-1 have been sequenced. This clone encodes a truncated peptide which shares an extended region of homology with the ionotropic glutamate receptors which covers part of the glutamate-binding site close to transmembrane domain I (TMI) and continues through TMII until the end of TMIII (FIG. 5 and FIG. 7A). The highest identity to animal iGluR is in the glutamate-binding domain (52%) (FIG. 6). The glutamate-binding region of animal iGluR is a two cleft domain shown by the hatched bars in FIG. 5. The Arabidopsis sequence shown in FIG. 7B, corresponds to the first of these glutamate-binding domains in animal iGluR (FIG. 5). The glutamate-binding domain shared between animal and plant iGluR has low but significant identity to the glutamine-binding domain of an *E. coli* permease gene (Nakanishi et al., 1990, Neuron 5:569–581) (FIG. 6). The ligand-binding R residue, which is conversed in all ionotropic glutamate receptors, is also conserved in the putative Arabidopsis iGluR (Kuryatov et al., 1994, Neuron 12:1291–1300).

In non-NMDA type animal iGluRs (kainate-binding iGluR and AMPA iGluR), their mRNAs are subject to RNA editing which modifies their function. For example, in the GluR2 subunit in AMPA type iGluR, RNA editing (Q to R) in TM II (FIG. 1) has been shown to regulate the Ca++ permeability. RNA editing leads to a decrease in Ca++ permeability (Choi, 1988, Neuron 1:623–634; Hume et al., 1991, Science 253:1028–1031). In Kainate-Binding type iGluR, both the GluR5 and GluR6 subunits also display the Q to R editing similar to the case of GluR2 of AMPA receptors (Sommer et al., 1991, Cell 67:11–19). GluR6 has two additional positions in TMI that are modified by RNA editing (Kohler et al., 1993, Neuron 10:491– 500). For GluR6, only when TMI is edited does editing in TMII (Q to R) influence Ca++ permeability (Kohler et al., 1993, Neuron 10:491–500). In contrast to the AMPA receptor channel, GluR6(R) channels edited in TMI show a higher Ca++ permeability than GluR6(Q) channels (Kohler et al., 1993, Neuron 10:491–500). In the case of NMDA type iGluR, all of the subunits do not show RNA editing in TMI and TMII. In fact all subunits contain an N at the site which Q to R editing occurs. NMDA receptors are highly permeable to Ca++.

Interestingly, the Q/R residue of animal non-NMDA-type ionotropic glutamate receptor which are subject to RNA editing or the corresponding non-editing. N residue of NMDA-type ionotropic glutamate receptor within TMII (Seeburg, 1995, TINS 16:359–365), are missing from the predicted peptide of Arabidopsis pAt-iGR-1. Since these residues are important for the regulation of permeability of Ca++ ions in animal ionotropic glutamate receptors (Burnashev et al., 1992, Neuron 8:189–198; Kohler et al., 1993, Neuron 10:491–500; Sommer et al., 1991, Cell 67:11–19) the Ca++ ion permeability in plant glutamate receptors may be regulated by a different mechanism.

The nucleotide sequences encoding Arabidopsis iGluR and mGluR genes can be used to screen cDNA libraries obtained from Arabidopsis and other plant species to identify further plant iGluR and mGluR genes. A plant cDNA library may be screened, under conditions of reduced stringency, using a radioactively or nonradioactively labeled fragment of the Arabidopsis iGluR and mGluR clones. Alternatively, the Arabidopsis iGlUR and mGluR sequences can be used to design degenerate or fully degenerate oligonucleotide probes which can be used as PCR probes or to screen plant cDNA libraries. Alternatively, the probes may be used to screen genomic libraries. As shown by working example, infra, this type of analysis has revealed the presence of both iGluR and mGluR genes in other dicots, such as tobacco, a legume, pea, and two monocots, corn and rice. For a review of cloning strategies which may be used, see e.g., Maniatis 1989 Molecular Cloning, A Laboratory Manual, Cold Spring Harbor Press, N.Y.

The plant GluR nucleotide sequences of the invention include (a) the DNA sequence shown in FIG. 15; (b) any nucleotide sequence that encodes the amino acid sequence shown in FIG. 15; (c) any nucleotide sequence that hybridizes to the complement of the cDNA sequence shown in FIG. 15 and encodes a functionally equivalent product; (d) any nucleotide sequence that hybridizes to the complement of of the DNA sequences that encode the amino acid sequence shown in FIG. 15 and encodes a functionally equivalent product; (e) any nucleotide sequence encoding a plant protein containing the amino acid sequence of the glutamate binding domain shown in FIG. 6; (f) any nucleotide sequence encoding a plant protein containing the amino acid sequences shown in FIG. 7A, 7B and/or 7C. Functional equivalents of the plant GluR include naturally occurring plant GluR in other plant species, and mutant GluR whether naturally occurring or engineered. The invention also includes degenerate variants of sequences (a) through (f).

The invention also includes nucleic acid molecules, preferably DNA molecules, that hybridize to, and are therefore the complements of, the nucleotide sequences (a) through (f), in the preceding paragraph. Such hybridization conditions may be highly stringent or less highly stringent, as described above. In instances wherein the nucleic acid molecules are deoxyoligonucleotides ("oligos"), highly stringent conditions may refer, e.g., to washing in 6×SSC/ 0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as plant GluR antisense molecules, useful, for example, in plant GluR gene regulation (for and/or as antisense primers in amplification reactions of plant GluR gene nucleic acid sequences). With respect to plant GluR gene regulation, such techniques can be used to regulate, for example, plant growth, development or gene expression. Further, such sequences may be used as part of ribozyme and/or triple helix sequences, also useful for plant GluR gene regulation.

In addition to the plant GluR nucleotide sequences described above, full length plant GluR cDNA or gene sequences present in the same species and/or homologs of the plant GluR gene present in other plant species can be identified and readily isolated, without undue experimentation, by molecular biological techniques well known in the art. The identification of homologs of plant GluR in related species can be useful for developing plant model systems for purposes of discovering plant iGluR agonists or antagonists to modify iGluR in plants to alter the following processes in either a positive or negative way: germination, growth rate, light-signal transduction and hormone signal transduction. Alternatively, such cDNA libraries, or genomic DNA libraries derived from the organism of interest can be screened by hybridization using the nucleotides described herein as hybridization or amplification probes. Furthermore, genes at other genetic loci within the genome that encode proteins which have extensive homology to one or more domains of the plant GluR gene product can also be identified via similar techniques. In the case of cDNA libraries, such screening techniques can identify clones derived from alternatively spliced transcripts in the same or different species.

Screening can be by filter hybridization, using duplicate filters. The labeled probe can contain at least 15–30 base pairs of the plant GluR nucleotide sequence, as shown in FIG. 15. The hybridization washing conditions used should be of a lower stringency when the cDNA library is derived from an organism different from the type of organism from which the labeled sequence was derived.

Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual, Cold Springs Harbor Press, N.Y.; and Ausubel et al., 1989, Current Protocols in Molecular Biology, Green Publishing Associates and Wiley Interscience, N.Y.

Alternatively, the labeled plant GluR nucleotide probe may be used to screen a genomic library derived from the organism of interest, again, using appropriately stringent conditions. The identification and characterization of plant genomic clones is helpful for designing diagnostic tests and clinical protocols for regulating plant growth rate, germination, light-signal transduction and hormone signal transduction. For example, sequences derived from regions adjacent to the intron/exon boundaries of the plant gene can be used to design primers for use in amplification assays to detect mutations within the exons, introns, splice sites (e.g. splice acceptor and/or donor sites), etc., that can be used in diagnostics.

Further, an plant GluR gene homolog may be isolated from nucleic acid of the organism of interest by performing PCR using two degenerate oligonucleotide primer pools designed on the basis of amino acid sequences within the plant GluR gene product disclosed herein. The template for the reaction may be cDNA obtained by reverse transcription of mRNA prepared from, for example, plant cell lines or tissue, known or suspected to express an plant GluR gene allele.

The PCR product may be subcloned and sequenced to ensure that the amplified sequences represent the sequences of a plant GluR gene. The PCR fragment may then be used to isolate a full length cDNA clone by a variety of methods. For example, the amplified fragment may be labeled and used to screen a cDNA library, such as a plant cDNA library. Alternatively, the labeled fragment may be used to isolate genomic clones via the screening of a genomic library.

PCR technology may also be utilized to isolate full length cDNA sequences. For example, RNA may be isolated, following standard procedures, from an appropriate cellular or tissue source (i.e., one known, or suspected, to express the plant GluR gene. A reverse transcription reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, cDNA sequences upstream of the amplified fragment may easily be isolated. For a review of cloning strategies which may be used, see e.g., Sambrook et al., 1989, supra.

The plant GluR gene sequences may additionally be used to isolate mutant plant GluR gene alleles. Such mutant alleles may be isolated from plant species either known or proposed to have a genotype which contributes to the symptoms plant growth rate, germination, light-signal transduction or hormone-signal transduction. Mutant alleles and mutant allele products may then be utilized in the therapeutic and diagnostic systems described below. Additionally, such plant GluR gene sequences can be used to detect plant GluR gene regulatory (e.g., promoter or promotor/enhancer) defects which can affect plant growth.

A cDNA of a mutant plant GluR gene may be isolated, for example, by using PCR, a technique which is well known to those of skill in the art. In this case, the first cDNA strand may be synthesized by hybridizing an oligo-dT oligonucleotide to mRNA isolated from tissue known or suspected to be expressed in a plant species putatively carrying the mutant plant GluR allele, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well known to those of skill in the art. By comparing the DNA sequence of the mutant plant GluR allele to that of the normal plant GluR allele, the mutation(s) responsible for the loss or alteration of function of the mutant plant GluR gene product can be ascertained.

Alternatively, a genomic library can be constructed using DNA obtained from a plant species suspected of or known to carry the mutant plant GluR allele, or a cDNA library can be constructed using RNA from a tissue known, or suspected, to express the mutant plant GluR allele. The normal plant GluR gene or any suitable fragment thereof may then be labeled and used as a probe to identify the corresponding mutant plant GluR allele in such libraries. Clones containing the mutant plant GluR gene sequences may then be purified and subjected to sequence analysis according to methods well known to those of skill in the art.

Additionally, an expression library can be constructed utilizing cDNA synthesized from, for example, RNA isolated from a tissue known, or suspected, to express a mutant plant GluR allele in a plant species suspected of or known to carry such a mutant allele. In this manner, gene products made by the putatively mutant tissue may be expressed and screened using standard antibody screening techniques in conjunction with antibodies raised against the normal plant GluR gene product, as described, below, in Section 5.3. (For screening techniques, see, for example, Harlow, E. and Lane, eds., 1988, "Antibodies: A Laboratory Manual", Cold Spring Harbor Press, Cold Spring Harbor.) Additionally, screening can be accomplished by screening with labeled GluR fusion proteins. In cases where a plant GluR mutation results in an expressed gene product with altered function (e.g., as a result of a missense or a frameshift mutation), a polyclonal set of antibodies to plant GluR are likely to cross-react with the mutant plant GluR gene product. Library clones detected via their reaction with such labeled antibodies can be purified and subjected to sequence analysis according to methods well known to those of skill in the art.

The invention also encompasses nucleotide sequences that encode mutant plant GluR, peptide fragments of the plant GluR, truncated plant GluR. and plant GluR fusion proteins. These include, but are not limited to nucleotide sequences encoding mutant plant GlUR described in section 5.2 infra; polypeptides or peptides corresponding to the signal peptide, two halves of the putative glutamate-binding domain and the three plus one transmembrane (TM) domains; truncated plant GluR in which one or two of the domains is deleted, e.g., a soluble plant GluR lacking the signal peptide, the glutamate-binding domain, or the TM domains, or a truncated, nonfunctional plant GluR lacking all or a portion of the glutamate binding domain. Nucleotides encoding fusion proteins may include by are not limited to full length plant GluR, truncated plant GluR or peptide fragments of plant GluR fused to an unrelated protein or peptide, such as for example, a transmembrane sequence, which anchors the plant GluR ECD to the cell membrane or an enzyme, fluorescent protein, luminescent protein which can be used as a marker.

The invention also encompasses (a) DNA vectors that contain any of the foregoing plant GluR coding sequences and/or their complements (i.e., antisense); (b) DNA expression vectors that contain any of the foregoing GluR coding sequences operatively associated with a regulatory element that directs the expression of the coding sequences; and (c) genetically engineered host cells that contain any of the foregoing plant GluR coding sequences operatively associated with a regulatory element that directs the expression of the coding sequences in the host cell. As used herein, regulatory elements include but are not limited to inducible and non-inducible promoters, enhancers, operators and other elements known to those skilled in the art that drive and regulate expression. Such regulatory elements include but are not limited to the promoters derived from the genome of plant cells (e.g., heat shock promoters; the promoter for the small subunit of RUBISCO; the promoter for the chlorophyll a/b binding protein) or from plant viruses (e.g., the 355 RNA promoter of CaMV; the coat protein promoter of tobacco mosaic virus (TMV), cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors.

5.2. Plant GluR Proteins and Polypeptides

Plant GluR protein, polypeptides and peptide fragments, mutated, truncated or deleted forms of the plant GluR and/or plant GluR fusion proteins can be prepared for a variety of uses, including but not limited to the generation of antibodies, the identification of other cellular gene products involved in the regulation of plant growth, as reagents in assays for screening for compounds that can be used as herbicides, and as pharmaceutical reagents useful in the treatment of CNS related disorders the plant GluR protein.

FIGS. 15, 6, 7A, 7B, and/or 7C show the amino acid sequence of the plant GluR protein respectively. As shown in FIG. 15 in this form of the plant GluR, the glutamate binding domain 1 spans from amino acid 466 to about 537; the TMI spans from amino acid 555 to about 580; the TMII spans from amino acid 592 to 608; the TMIII spans from about amino acid 614 to 634; the glutamate binding domain 2 spans from about amino acid 714 to 748; and TMIV spans from about amino acid 782 to 809. FIGS. 17 and 18 show the amino acid sequence alignment with these domains.

The plant GluR sequence begins with a methionine in a DNA sequence context consistent with a translation initiation site, followed by a typical hydrophobic signal sequence of peptide secretion.

The plant GluR amino acid sequences of the invention include the amino acid sequence shown in FIG. 15, FIG. 6 or FIGS. 7A, 7B and/or 7C, or the amino acid sequence encoded by cDNA clone PAT-iGR-1 (EST #107M14T7), or encoded by cDNA clone PAT-mGR-1 (EST #97C23T7). Further, plant GluR of other plant species are encompassed by the invention. In fact, any plant GluR protein encoded by the plant GluR nucleotide sequences described in Section 5.1, above, are within the scope of the invention.

The invention also encompasses proteins that are functionally equivalent to the plant GluR encoded by the nucleotide sequences described in Section 5.1, as judged by any of a number of criteria, including but not limited to the ability to bind glutamate, the binding affinity for glutamate, the resulting biological effect of glutamate binding, e.g., signal transduction, a change in cellular metabolism (e.g., ion flux, tyrosine phosphorylation) or change in phenotype when the plant GluR equivalent is present in an appropriate cell type such as, an increase in plant growth. Such functionally equivalent plant GluR proteins include but are not limited to additions or substitutions of amino acid residues within the amino acid sequence encoded by the plant GluR nucleotide sequences described, above, in Section 5.1, but which result in a silent change, thus producing a functionally equivalent gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

While random mutations can be made to plant GluR DNA (using random mutagenesis techniques well known to those skilled in the art) and the resulting mutant plant GluRs tested for activity, site-directed mutations of the GluR coding sequence can be engineered (using site-directed mutagenesis techniques well known to those skilled in the art) to generate mutant plant GluRs with increased function, e.g., higher binding affinity for glutamate, and/or greater signalling capacity; or decreased function, e.g., lower binding affinity for glutamate, and/or decreased signal transduction capacity.

For example, the alignment of animal form of GLuR and the plant GluR homolog is shown in FIG. 18 in which identical amino acid residues are indicated by vertical lines and conserved residues are indicated by dots. Conservative alterations at the variable positions can be engineered in order to produce a mutant plant GLuR that retains function; e.g., glutamate binding affinity or signal transduction capability or both. Non-conservative changes can be engineered at these variable positions to alter function, e.g., glutamate binding affinity or signal transduction capability, or both. Alternatively, where alteration of function is desired, deletion or non-conservative alterations of conserved residues in the glutamate binding domain (indicated in FIG. 18) can be engineered. For example, deletion or non-conservative alterations (substitutions or insertions) of the glutamate binding domains, e.g., amino acid residues 466 to 537 and 714 to 748 (FIG. 18) of plant GluR or portions of the glutamate binding domain, e.g., amino acid residues 466–537 (FIG. 18) of plant GluR, or amino acid residues 714–748 can be engineered to produce a mutant plant GluR that binds glutamate but is signalling-incompetent. Non-conservative alterations to the residues in the TMs shown in FIG. 18 can be engineered to produce mutant plant GluRs with altered binding affinity for glutamate.

Other mutations to the plant GluR coding sequence can be made to generate plant GluRs that are better suited for expression, scale up, etc. in the host cells chosen. For example, cysteine residues can be deleted or substituted with another amino acid in order to eliminate disulfide bridges; N-linked glycosylation sites can be altered or eliminated to achieve, for example, expression of a homogeneous product that is more easily recovered and purified from yeast hosts which are known to hyperglycosylate N-linked sites. To this end, a variety of amino acid substitutions at one or both of the first or third amino acid positions of any one or more of the glycosylation recognition sequences which occur in the extracellular domain (ECD) (N-X-S or N-X-T), and/or an amino acid deletion at the second position of any one or more such recognition sequences in the ECD will prevent glycosylation of the plant GluR at the modified tripeptide sequence.

Peptides corresponding to one or more domains of the plant GluR (e.g., ECD, TM or CD), truncated or deleted plant GluR (e.g., GluR in which the TM and/or CD is deleted) as well as fusion proteins in which the full length GluR, a GluR peptide or truncated GluR is fused to an unrelated protein are also within the scope of the invention and can be designed on the basis of the GluR nucleotide and GluR amino acid sequences disclosed in this Section and in Section 5.1, above. Such fusion proteins include but are not limited to IgFc fusions which stabilize the plant GluR protein or peptide and prolong half-life in vivo; or fusions to any amino acid sequence that allows the fusion protein to be anchored to the cell membrane, allowing the ECD to be exhibited on the cell surface; or fusions to an enzyme, fluorescent protein, or luminescent protein which provide a marker function.

While the plant GluR polypeptides and peptides can be chemically synthesized (e.g., see Creighton, 1983, Proteins: Structures and Molecular Principles, W.H. Freeman & Co., N.Y.), large polypeptides derived from the GluR and the full length GluR itself may advantageously be produced by recombinant DNA technology using techniques well known in the art for expressing nucleic acid containing plant GluR gene sequences and/or coding sequences. Such methods can be used to construct expression vectors containing the plant GluR nucleotide sequences described in Section 5.1 and appropriate transcriptional and translational control signals. These methods include, for example, in vitro recombinant DNA techniques, synthetic techniques, and in vivo genetic recombination. See, for example, the techniques described in Sambrook et al., 1989, supra, and Ausubel et al., 1989, supra. Alternatively, RNA capable of encoding plant GluR nucleotide sequences may be chemically synthesized using, for example, synthesizers. See, for example, the techniques described in "Oligonucleotide Synthesis", 1984, Gait, M. J. ed., IRL Press, Oxford, which is incorporated by reference herein in its entirety.

A variety of host-expression vector systems may be utilized to express the plant GluR nucleotide sequences of the invention. Where the GluR peptide or polypeptide is a soluble derivative (e.g., GluR peptides corresponding to the ECD; truncated or deleted GluR in which the TM and/or CD are deleted) the peptide or polypeptide can be recovered from the culture, i.e., from the host cell in cases where the GluR peptide or polypeptide is not secreted, and from the culture media in cases where the GluR peptide or polypeptide is secreted by the cells. However, the expression systems also encompass engineered host cells that express the plant GluR or functional equivalents in situ, i.e., anchored in the cell membrane. Purification or enrichment of the plant GluR from such expression systems can be accomplished using appropriate detergents and lipid micelles and methods well known to those skilled in the art. However, such engineered host cells themselves may be used in situations where it is important not only to retain the structural and functional characteristics of the plant GluR, but to assess biological activity, e.g., in herbicide screening assays.

Methods which are well known to those skilled in the art can be used to construct expression vectors containing the plant GluR coding sequence and appropriate transcriptional/translational control signals. These methods include in vitro recombinant DNA techniques, synthetic techniques and in vivo recombination/genetic recombination. See, for example, the techniques described in Maniatis et al., 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y.

A variety of host-expression vector systems may be utilized to express the plant GluR coding sequence. These include but are not limited to microorganisms such as bacteria transformed with recombinant bacteriophage DNA, plasmid DNA or cosmid DNA expression vectors containing the plant GluR coding sequence; yeast transformed with recombinant yeast expression vectors containing the plant GluR coding sequence; insect cell systems infected with recombinant virus expression vectors (e.g., baculovirus) containing the plant GluR coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the plant GluR coding sequence; or animal cell systems infected with recombinant virus expression vectors (e.g., adenovirus, vaccinia virus) including cell lines engineered to contain multiple copies of the plant GluR either stably amplified (CHO/dhfr) or unstably amplified in double-minute chromosomes (e.g., murine cell lines).

The expression elements of these systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of-the plant GluR DNA SV40-, BPV- and EBV-based vectors may be used with an appropriate selectable marker.

In bacterial systems a number of expression vectors may be advantageously selected depending upon the use intended for the plant GluR expressed. For example, when large quantities of plant GluR are to be produced for the generation of antibodies or to screen peptide libraries, vectors which direct the expression of high levels of fusion protein products that are readily purified may be desirable. Such vectors include but are not limited to the E. coli expression vector pUR278 (Ruther et al., 1983, EMBO J. 2:1791), in which the plant GluR coding sequence may be ligated into the vector in frame with the lac Z coding region so that a hybrid GluR lac Z protein is produced; pIN vectors (Inouye & Inouye, 1985, Nucleic acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned polypeptide of interest can be released from the GST moiety.

In yeast, a number of vectors containing constitutive or inducible promoters may be used. For a review see, Current Protocols in Molecular Biology, Vol. 2, 1988, Ed. Ausubel et al., Greene Publish. Assoc. & Wiley Interscience, Ch. 13; Grant et al., 1987, Expression and Secretion vectors for Yeast, in Methods in Enzymology, Eds. Wu & Grossman, 1987, Acad. Press, N.Y., Vol. 153, pp. 516–544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673–684; and The Molecular Biology of the Yeast Saccharomyces, 1982, Eds. Strathern et al., Cold Spring Harbor Press, Vols. I and II.

In cases where plant expression vectors are used, the expression of the plant GluR coding sequence may be driven by any of a number of promoters. For example, viral promoters such as the 35S RNA and 19S RNA promoters of CaMV (Brisson et al., 1984, Nature 310:511–514), or the coat protein promoter of TMV. (Takamatsu et al., 1987, EMBO J. 6:307–311) may be used; alternatively, plant promoters such as the small subunit of RUBISCO (Coruzzi et al., 1984, EMBO J. 3:1671–1680; Broglie et al., 1984, Science 224:838–843); or heat shock promoters, e.g., soybean hsp17.5-E or hsp17.3-B (Gurley et al., 1986, Mol. Cell. Biol. 6:559–565) may be used. These constructs can be introduced into plant cells using Ti plasmids, Ri plasmids, plant virus vectors, direct DNA transformation, microinjection, electroporation, etc. For reviews of such techniques see, for example, Weissbach & Weissbach, 1988, Methods for Plant Molecular Biology, Academic Press, NY, Section VIII, pp. 421–463; and Grierson & Corey, 1988, Plant Molecular Biology, 2d Ed., Blackie, London, Ch. 7–9.

For long-term, high-yield production of recombinant proteins, stable expression is preferred. For example, cell lines which stably express the plant GluR may be engineered. Rather than using expression vectors which contain viral origins of replication, host cells can be transformed with the plant GluR DNA controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the plant GluR on the cell surface, and which respond to glutamate mediated signal transduction. Such engineered cell lines are particularly useful in screening glutamate analogs.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy et al., 1980, Cell 22:817) genes can be employed in tk$^-$, hgprt$^-$ or aprt$^-$ cells, respectively. Also, antimetabolite resistance can be used as the basis of selection for dhfr, which confers resistance to methotrexate (Wigler et al., 1980, Natl. Acad. Sci. USA 77:3567; O'Hare et al., 1981, Proc. Natl.. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin et al., 1981, J. Mol. Biol. 150:1); and hygro, which confers resistance to hygromycin genes (Santerre, et al., 1984, Gene 30:147). Recently, additional selectable genes have been described, namely trpB, which allows cells to utilize indole in place of tryptophan; hisD, which allows cells to utilize histinol in place of histidine (Hartman & Mulligan, 1988, Proc. Natl. Acad. Sci. USA 85:8047); and ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.). The invention also encompasses (a) DNA vectors that contain any of the foregoing coding sequences and/or their complements (i.e., antisense); (b) DNA expression vectors that contain any of the foregoing coding sequences operatively associated with a regulatory element that directs the expression of the coding sequences; and (c) genetically engineered host cells and/or plants that contain any of the foregoing coding sequences operatively associated with a regulatory element that directs the expression of the coding sequences in the host cell. As used herein, regulatory elements include but are not limited to inducible and non-inducible promoters, enhancers, operators and other elements known to those skilled in the art that drive and regulate expression.

In addition to the gene sequences described above, homologues of such sequences, as may, for example, be present in other plant species may be identified and may be readily isolated, without undue experimentation, by molecular biological techniques well known in the art. Further, there may exist genes at other genetic loci within the genome that encode proteins which have extensive homology to one or more domains of such gene products. These genes may also be identified via similar techniques.

For example, the isolated GluR gene sequence may be labeled and used to screen a cDNA library constructed from mRNA obtained from the organism of interest. The hybridization conditions used should be of a lower stringency when the cDNA library is derived from an organism different from the type of organism from which the labeled sequence was derived. Alternatively, the labeled fragment may be used to screen a genomic library derived from the organism of interest, again, using appropriately stringent conditions. Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual, Cold springs Harbor Press, N.Y.; and Ausubel et al., 1989, Current Protocols in Molecular Biology, Green Publishing Associates and Wiley Interscience, N.Y.

Further, previously unknown GluR gene-type sequences may be isolated by performing PCR using two degenerate oligonucleotide primer pools designed on the basis of amino acid sequences within the gene of interest. The template for the reaction may be cDNA obtained by reverse transcription of mRNA prepared from cell lines or tissue known or suspected to express an GluR gene allele.

The PCR product may be subcloned and sequenced to ensure that the amplified sequences represent the sequences of an GluR gene-like nucleic acid sequence. The PCR fragment may then be used to isolate a full length cDNA clone by a variety of methods. For example, the amplified fragment may be labeled and used to screen a bacteriophage cDNA library. Alternatively, the labeled fragment may be used to screen a genomic library.

PCR technology may also be utilized to isolate full length cDNA sequences. For example, RNA may be isolated, following standard procedures, from an appropriate cellular or tissue source. A reverse transcription reaction may be performed on the RNA using an oligonucleotide primer specific for the most 5'end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, cDNA sequences upstream of the amplified fragment may easily be isolated. For a review of cloning strategies which may be used, see e.g., Sambrook et al., 1989, supra.

In cases where the GluR gene identified is the normal, or wild type gene, this gene may be used to isolate mutant alleles of the gene. Mutant alleles may be isolated from plants either known or proposed to have a genotype which contributes abnormal growth characteristics. Mutant alleles and mutant allele products may then be utilized in the development of in vitro assays, plant assay systems, and transgenic plants as described below.

A cDNA of the mutant gene may be isolated, for example, by using PCR, a technique which is well known to those of skill in the art. In this case, the first cDNA strand may be synthesized by hybridizing an oligo-dT oligonucleotide to mRNA isolated from tissue known or suspected to be expressed in an individual putatively carrying the mutant allele, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well known to those of skill in the art. By comparing the DNA sequence of the mutant gene to that of the normal gene, the mutation(s) responsible for the loss or alteration of function of the mutant gene product can be ascertained.

Alternatively, a genomic or cDNA library can be constructed and screened using DNA or RNA, respectively, from plant cells, tissues or whole plants suspected of expressing the gene of interest in an individual suspected of or known to carry the mutant allele. The normal gene or any suitable fragment thereof may then be labeled and used as a probed to identify the corresponding mutant allele in the library. The clone containing this gene may then be purified and subjected to sequence analysis according to methods well known to those of skill in the art.

Additionally, an expression library can be constructed utilizing DNA isolated from or cDNA synthesized from plant cells, tissues or whole plants suspected of expressing the gene of interest in an individual suspected of or known to carry the mutant allele. In this manner, gene products made by the putatively mutant tissue may be expressed and screened using standard antibody screening techniques in conjunction with antibodies raised against the normal gene product, as described, below, in Section 5.3. (For screening techniques, see, for example, Harlow, E. and Lane, eds., 1988, "Antibodies: A Laboratory Manual", Cold Spring Harbor Press, Cold Spring Harbor.) In cases where the mutation results in an expressed gene product with altered function (e.g., as a result of a missense mutation), a polyclonal set of antibodies are likely to cross-react with the mutant gene product. Library clones detected via their reaction with such labeled antibodies can be purified and subjected to sequence analysis according to methods well known to those of skill in the art.

5.2.1. Identification of Transfectants or Transformants Expressing the Plant GluR Gene Product The host cells which contain the plant GluR coding sequence and which express the biologically active gene product may be identified by at least four general approaches: (a) DNA-DNA or DNA-RNA hybridization; (b) the presence or absence of "marker" gene functions; (c) assessing the level of transcription as measured by the expression of plant GluR mRNA transcripts in the host cell; and (d) detection of the gene product as measured by immunoassay or by its biological activity.

In the first approach, the presence of the plant GluR coding sequence inserted in the expression vector can be detected by DNA-DNA or DNA-RNA hybridization using probes comprising nucleotide sequences that are homologous to the plant GluR coding sequence or portions or derivatives thereof.

In the second approach, the recombinant expression vector/host system can be identified and selected based upon the presence or absence of certain "marker" gene functions (e.g., thymidine activity, resistance to antibiotics, resistance to methotrexate, transformation phenotype, occlusion body formation in baculovirus, etc.). For example, if the plant GluR coding sequence is within a marker gene sequence of the vector, recombinants containing the plant GluR coding sequence can be identified by the absence of the marker gene function. Alternatively, a marker gene can be placed in tandem with the plant GluR sequence under the control of the same or different promoter used to control the expression of the plant GluR coding sequence. Expression of the marker in response to induction or selection indicates expression of the plant GluR coding sequence.

In the third approach, transcriptional activity for the plant GluR coding region can be assessed by hybridization assays. For example, RNA can be isolated and analyzed by Northern blot using a probe homologous to the plant GluR coding sequence or particular portions thereof substantially as shown in FIGS. 6 and 7. Alternatively, total nucleic acids of the host cell may be extracted and assayed for hybridization to such probes.

In the fourth approach, the expression of the plant GluR protein product can be assessed immunologically, for example by Western blots, immunoassays such as radioimmuno-precipitation, enzyme-linked immunoassays and the like. The ultimate test of the success of the expression system, however, involves the detection of the biologically active plant GluR gene product. Where the host cell secretes the gene product, the cell free media obtained from the cultured transfectant host cell may be assayed for plant GluR activity. Where the gene product is not secreted, cell lysates may be assayed for such activity. In either case, a number of assays can be used to detect plant GluR activity including but not limited to the following: cycloxygenase activity may be determined in the culture medium by the addition of exogenous arachidonic acid substrate (30 $\mu$M for 15 min. at 37° C.) followed by conversion of the prostayalandin $E_{20}$ product to a methyl oximate form. This bicyclic derivative may then be quantitated by radioimmunoassay (kit from Amersham Corp).

Desired plants and plant cells may be obtained by engineering the gene constructs described herein into a variety of plant cell types, including but not limited to, protoplasts, tissue culture cells, tissue and organ explants, pollen, embryos as well as whole plants. In an embodiment of the present invention, the engineered plant material is selected or screened for transformants (i.e., those that have incorporated or integrated the introduced gene construct(s)) following the approaches and methods described below. An isolated transformant may then be regenerated into a plant. Alternatively, the engineered plant material may be regenerated into a plant or plantlet before subjecting the derived plant or plantlet to selection or screening for the marker gene traits. Procedures for regenerating plants from plant cells, tissues or organs, either before or after selecting or screening for marker gene(s), are well known to those skilled in the art.

A transformed plant cell, callus, tissue or plant may be identified and isolated by selecting or screening the engineered plant material for traits encoded by the marker genes present on the transforming DNA. For instance, selection may be performed by growing the engineered plant material on media containing inhibitory amounts of the antibiotic or herbicide to which the transforming marker gene construct confers resistance. Further, transformed plants and plant cells may also be identified by screening for the activities of any visible marker genes (e.g., the $\beta$-glucuronidase, luciferase, B or C1 genes) that may be present on the recombinant nucleic acid constructs of the present invention. Such selection and screening methodologies are well known to those skilled in the art.

Physical and biochemical methods also may be used to identify a plant or plant cell transformant containing the gene constructs of the present invention. These methods include but are not limited to: 1) Southern analysis or PCR amplification for detecting and determining the structure of the recombinant DNA insert; 2) Northern blot, S-1 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct; 4) protein gel electrophoresis, western blot techniques, immunoprecipitation, or enzyme-linked immunoassays, where the gene construct products are proteins; 5) biochemical measurements of compounds produced as a consequence of the expression of the introduced gene constructs. Additional techniques, such as in situ hybridization, enzyme staining, and immunostaining, also may be used to detect the presence or expression of the recombinant construct in specific plant organs and tissues. The methods for doing all these assays are well known to those skilled in the arts.

5.2.2. Purification of the Plant GluR Gene Product

Once a cell that produces high levels of biologically active plant GluR is identified, the cell may be clonally expanded and used to produce large quantities of the receptor. The receptor may be purified using techniques well-known in the art including, but not limited to, immunoaffinity purification, chromatographic methods including high performance liquid chromatography and the like. Where the gene product is secreted by the cultured cells, plant GluR polypeptides or peptides may be readily recovered from the culture medium.

Where the plant GluR coding sequence has been engineered to encode a cleavable fusion protein, the purification of lant GluR may be readily accomplished using affinity purification techniques. For example, an antibody specific for the heterologous peptide or protein can be used to capture the durable fusion protein; for example, on a solid surface, a column etc. The plan GluR moiety can be released by treatment with the appropriate enzyme that cleaves the linkage site.

The ease of cDNA construction using the polymerase chain reaction, transfection and purification of the expressed protein permits the isolation of small, but sufficient amount of plant GluR for characterization of the receptor's physical and kinetic properties. Using site-directed mutagenesis or naturally occurring mutant sequences, this system provides a reasonable approach to determine the effects of the altered primary structure on the function of the protein. Fusion constructs having the domain of plant GluR preceding the amino terminus of the cleavable protein versus constructs having the opposite arrangement, may also be engineered to evaluate which fusion construct will interfere the least, if at all, with the protein's biologic function and the ability to be purified.

Using this aspect of the invention, any cleavage site or enzyme cleavage substrate may be engineered between the plant GluR sequence and a second peptide or protein that has a binding partner which could be used for purification, e.g, any antigen for which an immunoaffinity column can be prepared.

5.3. Antibodies to GluR Proteins

Antibodies that define the GluR gene product are within the scope of this invention, and include antibodies capable of specifically recognizing one or more GluR gene product epitopes. Such antibodies may include, but are not limited to, polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above. Such antibodies may be used, for example, in the detection of an GluR gene product in a biological sample, including, but not limited to, blood plasma and serum. Alternatively, the antibodies may be used as a method for the inhibition of abnormal GluR gene product activity.

Monoclonal antibodies, which are homogeneous populations of antibodies to a particular antigen, may be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce single chain antibodies against GluR gene products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity.

5.4. Transgenic Plants that Express Mutant GluR

Glutamate in plants may also act as an important signal for growth and development. It is therefore possible to alter the growth and development patterns of the plants by modulating the iGluR or mGluR or glutamate-like receptor activities by engineering transgenic plants express either wild type or mutant forms of plant GluR as discussed in Sections 5.1 and 5.2. Glutamate has potential activity in regulating circadium rythym, therefore it is possible to engineer transgenic plants expressing mutated GluR to alter the plant's response to light and the biological clock. Thus, for example it would be possible to engineer plants which flower early or later, etc. The overexpression of AS and GS genes results in plants with excellent growth traits, that is, they grow faster and larger. Therefore, it is possible by altering the GluR to stimulate over expression of the AS gene, to genetically engineer plants with similar growth traits. In addition, by altering the GluR in genetically engineered cells it may also be possible to synchronize cells in culture, as well as synchronizing plants and seed germination.

According to the present invention, a desirable plant or plant cell may be obtained by transforming a plant cell with the nucleic acid. constructs described in Section 5.1. In some instances, it may be desirable to engineer a plant or plant cell with several different gene constructs. Such engineering may be accomplished by transforming a plant or plant cell with all of the desired gene constructs simultaneously. Alternatively, the engineering may be carried out sequentially. That is, transforming with one gene construct, obtaining the desired transformant after selection and screening, transforming the transformant with a second gene construct, and so on.

In an embodiment of the present invention, Agrobacterium can be employed to introduce the gene constructs into plants. Such transformations preferably use binary Agrobacterium T-DNA vectors (Bevan, 1984, Nuc. Acid Res. 12:8711–8721), and the co-cultivation procedure (Horsch et al., 1985, Science 227:1229–1231). Generally, the Agrobacterium transformation system is used to engineer dicotyledonous plants (Bevan et al., 1982, Ann. Rev. Genet 16:357–384; Rogers et al., 1986, Methods Enzymol. 118:627–641). The Agrobacterium transformation system may also be used to transform as well as transfer DNA to monocotyledonous plants and plant cells. (see Hernalsteen et al., 1984, EMBO J 3:3039–3041 ; Hooykass-Van Slogteren et al., 1984, Nature 311:763–764; Grimsley et al., 1987, Nature 325:1677–179; Boulton et al., 1989, Plant Mol. Biol. 12:31–40.; Gould et al., 1991, Plant Physiol. 95:426–434).

In other embodiments, various alternative methods for introducing recombinant nucleic acid constructs into plants and plant cells may also be utilized. These other methods are particularly useful where the target is a monocotyledonous plant or plant cell. Alternative gene transfer and transformation methods include, but are not limited to, protoplast transformation through calcium-, polyethylene glycol (PEG)- or electroporation-mediated uptake of naked DNA (see Paszkowski et al., 1984, EMBO J 3:2717–2722, Potrykus et al. 1985, Molec. Gen. Genet. 199:169–177; Fromm et al., 1985, Proc. Nat. Acad. Sci. USA 82:5824–5828; Shimamoto, 1989, Nature 338:274–276) and electroporation of plant tissues (D'Halluin et al., 1992, Plant Cell 4:1495–1505). Additional methods for plant cell transformation include microinjection, silicon carbide mediated DNA uptake (Kaeppler et al., 1990, Plant Cell Reporter 9:415–418), and microprojectile bombardment (see Klein et al., 1988, Proc. Nat. Acad. Sci. USA 85:4305–4309; Gordon-Kamm et al., 1990, Plant Cell 2:603–618).

According to the present invention, a wide variety of plants and plant cell systems may be engineered for the desired physiological and agronomic characteristics described herein using the nucleic acid constructs of the instant invention and the various transformation methods mentioned above. In preferred embodiments, target plants and plant cells for engineering include, but are not limited to, those of maize, wheat, rice, soybean, tomato, tobacco, carrots, peanut, potato, sugar beets, sunflower, yam, Arabidopsis, rape seed, and petunia.

The present invention also encompasses the use of the cDNA clones of the plant GluR to not only select for new herbicides, but to also genetically engineer herbicide resistant plants. Gene constructs encoding the plant glutamate receptor protein and polypeptides can be used in genetic engineering of plants to alter the plant's growth requirements or conditions. The invention also encompasses genetically engineered plants that express mutagenized forms of the plant GluR so that the plants are able to utilize alternative nitrogen sources, which may prove to be beneficial, for example in improving plant growth in nitrogen limited soil. Given the important role that glutamate signaling plays in timing of cell division or flowering, transgenic plants may be engineered to produce more flowers or fruit in response to a specific nitrogen source. Therefore the present invention has many utilities in.genetic engineering of plants to improve their agronomic or industrial properties.

The invention further encompasses transgenic plants expressing chimeric GluR. By exchanging portions of the glutamate binding domain with segments of receptors sensitive to other compounds it is possible to engineer a receptor with specific resistance or growth response to that specific compound. Animal GluR subunits with specificity to particular agonists have been identified. (Bach et al., 1994, Neuron 13: 1343–1357). Through mutagenesis of the plant GluR it is possible to identify similar segments in plants and to genetically engineer GluR responsive to one specific agonist or analog of glutamate. Transgenic plants expressing such receptors would have improved agronomic and industrial properties.

5.5. Screening Assays for Herbicides

The present invention also encompasses screening assays to identify agonists and antagonists of glutamate induced signaling. This invention provides a novel, rapid and cost effective means of screening or identifying novel plant growth regulators and pharmaceutical drugs. The methods are based in some cases on in vivo screening of drugs for their abilities to alter plant growth, development or gene expression in a manner that can be reversed or enhanced by glutamate or glutamate-antagonists. In other embodiments, the methods are based on in vitro screening of drugs for their abilities to compete or interfere with glutamate binding of plant or animal glutamate receptors. These methods may be used to identify novel stimulatory or inhibitory plant growth regulatory compounds.

5.5.1. In Vitro Assays

The present invention also encompasses the use of in vitro screens to identify drugs for their ability to interefere with glutamate binding of plant or animal glutamate receptors. A potential method for in vitro screening involves linking the isolated plant glutamate receptor to a solid matrix, such as a sepharose. A solution containing glutamate along with the specific drug in varying concentrations. After several washes, the amount of glutamate bound to the receptor can be measured by applying a radioactively or fluorescently tagged antibody directed to the glutamate binding domain. The effectiveness of the inhibitors would be measured by the amount of antibody in the flow through. This would be a very rapid and cost effective assay to initially screen for potential inhibitors of glutamate bindinding to its receptor.

5.5.2. Cell Culture Assays

The present invention encompasses the use of cell lines, that express the plant GluR, in in vitro assays to screen drugs for their effects on plant growth mediated by the GluR. Preferably, continuous cell lines stably expressing the GluR gene product or mutants thereof as described above and preferably which respond to the signal generated by glutamate binding are utilized in assays to ideatify novel drugs that either mimic the effects of glutamate or act as glutamate antagonists. Cell lines that may be used in the cell culture assay include any cells, including animal, human or plant cells, that are engineered (as described in Section 5) to express the plant GluR. Glutamate receptor gene products encoding plant iGluR, mGluR, glutamate-like receptors, or any other glutamate receptor expressed in plants, as described in Section 5.1. may be expressed in cells for use in cell culture assay system.

In this assay, cells expressing the GluR in culture mdium will be treated with potential agonists and antagonists. These drugs will be added in serial dilution to the culture medium. The effects of these drugs will be measured as changes in cell metabolism or growth, changes in gene expression, changes in downstream signaling events and changes in membrane potential. The effects of the drugs should be reversed by glutamate supplemention, which idnicates that the inhibitory effects are specific to the glutamate-related process.

The cell culture assay will include cells expressing glutamate responsive gene promoters linked to reporter genes. AS and GS genes are induced in response to glutamate binding its receptor. Therefore, drugs can be tested for their ability to activate the GluR by induction of AS and GS genes. Induction of gene expression will be measured by linking the AS and GS promoters to reporter genes, such as chloramphenicol transferese, which are commonly used in the art. Induction of the GluR will be rapdily measured by assaying for the reporter genes activity.

The cell culture assay will also include assaying for GluR activators or inhibitors by measuring an electrophysiological response. Cells, i.e. Hela cells, expressing the plant GluR can be used to assay for inhibitors or activators of the GluR by measuring changes in membrane potential. Ionotropic GluR are known to be ion gated therefore activation or inhibition of the GluR may be measured as a change in membrane potential by methods well known to those skilled in the art.

The in vitro cell assay will provide a very rapid method to screen potential agonists and antagonists of the GluR. The use of cell lines expressing mutants of the GluR will provide more information regarding the action of these compounds. Primary cell cultures, protoplast and/or cell lines stably expressing the GluR which also express mutations in the signal transduction pathways will be a very useful tool in determining the downstream signaling events. For example, cell lines stably expressing the GluR may also express a mutant of the plant ras homolog or the plant mitogen-activated kinase (MAPK) homolog in order to determine whether ras or MAPK is required by glutamate mediated effects on cell metabolism and gene expression. Changes in MAPK activity or phosphorylation may also be utilized as an indicator of GluR activation.

This in vitro assay system is useful for screening and identifying potential inhibitors or activators of signaling cascades activated by plants. Cell lines expressing mutagenized GluR will provide a means of identifying inhibitors of GluR activated signaling events which may be potential herbicides. The effects or inhibitors or activators may be observed by measuring changes in gene expression and phosphorylation events by methods well known by those skilled in the art.

In another embodiment, the methods are based on in vitro screening of drugs for their abilities to compete or interfere with glutamate binding of animal glutamate receptors. Therefore the invention also encompasses plant cells expressing both wild-type and mutant forms of the animal GluR. In order to perform cell culture assays for drugs which would stimulate or inhibit animal glutamate receptors.

5.5.3. Plant Growth Assay

In order to screen for potential plant growth regulators, assays measuring changes in plant growth in response to potential GluR agonists and antagonists in encompassed by the present invention. Assay measuring changes in plant growth include changes in root, stem, or leaf growth. The use of transgenic plants as described in Section 5.4. is also included.

The following assay may be utilized in order to screen drugs for their effects on plant growth mediated by the GluR. Arabidopsis seedlings expressing or overexpressing the GluR are treated with the potential agonist or antagonist. In this plant growth assay, Arabidopsis seeds are plated on tissue culture plates in MS Medium (Murashige and Skoog Salt Mixture-plant basic medium available from Gibco (BRL)). A dose-response curve is determined using various concentrations of the potential agonist or antagonist added to the medium. The plants are grown vertically in a growth chamber at 22° C. with a 16 hour light/8 hour dark cycle for two weeks. The effects of each herbicide on plant growth is assessed by measuring root length on vertical tissue culture plates. The effectiveness of the drug is measured by a increase or reduction in root growth. The effect of the drug should be reversed by glutamate supplementation, which indicates that the inhibitory effects are specific to a glutamate-related process.

This assay also has utility in the selection of new pharmacological agonists and antagonist for use as human drugs. The pathophysiological involvement of GluR receptors in animals has been reviewed (Gasic et al., 1992, Annu. Rev. Physiol. 54: 507–536). As summarized by Gasic and Hollmann (1992), glutamate receptors in animals are involved in CNS disorders such as Huntington's disease, Parkinson's disease, and Alzheimer's disease. GluR is also involved in the initiation and propagation of seizures and in massive neuronal cell death during periods of ischemia and hypoglycemia. It has also been reported that NMDA receptor antagonists may confer protection to some neurotoxicity in an experimental model of Parkinson's disease (Graham et al. 1990, Life Sci 47:PL91-PL97). Moreover, both non-competitive NMDA receptor antagonist (dizocilpine) and competitive NMDA receptor antagonist (DlL-(E)-2-amino-4-methyl-5-phosphono-3-pentonoic acid) may act as antidepressant (Papp et al., 1994, Eur. J. Pharmacol. 263:1–7). Isolated Arabidopsis mutants which are supersensitive to GluR agonists or antagonists will be utilized to screen for new pharmaceutical drugs such as new antidepressants. The bioassay for new GluR acting drugs would be sensitive, rapid, and cost-effective to operate.

This assay will also have utility to screen and identify potential inhibitors or activators of signaling cascades activated by the plant GluR. The activation of the GluR leads to activation of downstream signaling events which are required for the observed changes in plant metabolism and development. Therefore the mutagenized Arabidopsis seedlings will have utility in assaying potential inhibitors or activators of the GluR activated signaling events. The effects of the inhibitors or activators will be observed by measuring changes in root length on vertical tissue plates.

5.6. Herbicides that Block the GluR Signal

A further aspect of the invention relates to novel plant growth regulators that mimic or antagonize glutamate in regulating plant metabolism, physiology and/or gene expression. The novel plant growth regulators may have structural homology to agonists or antagonists of animal glutamate receptors. Plant growth regulators that mimic or antagonize the GluR may also be useful in synchronizing plant development and seed germination, as well as synchronizing cells in culture. The novel plant growth regulators may also have activities as agonists or antagonists of animal glutamate receptors.

Glutamate analogs should be effective herbicide targets, given that they are all acting not only through some target enzymes, but through plant amino acids receptors which signal downstream responses. The short-term and long-term herbicidal effects on the downstream reactions of these receptors would be more profound than the inhibition of a single biochemical reaction. The suggestion that some herbicides can affect a whole series of downstream responses have been implicated in Balke's review (Balke, 1985, In: Weed Physiology. CRC Press, Inc., p113–139). Several herbicides are suggested to be able to affect the hormonal and environmental regulation of membrane functions. For example, both the auxin and auxin antagonist herbicides affect membrane functions that are associated with the action of IAA in plant cells. Several herbicides can also affect the phytochrome-regulated Ca++ transport and blue light induced absorbance change. However, the detailed mechanisms of these herbicidal effects are yet to be fully elucidated and the corresponding receptors of the signals are poorly understood.

The present invention also includes plant growth regulators, including herbicides that prevent glutamate from binding to the glutamate receptor. Potential herbicides include, but are not limited to, peptides corresponding to extracellular domain of the glutamate receptor. These peptides would bind to glutamate and prevent binding to the receptor.

The present invention also includes herbicides that would not only act by binding to the GluR, but rather act intracellularly to inhibit downstream signaling pathways. Activation of the plant GluR results in the activation of signaling cascades. These signaling cascades and inhibitors thereof are well characterized in animals. Therefore given the strong identity between the animal and plant glutamate receptors, it is likely that similar signaling pathways are activated downstream and therefore inhibitors of these pathways in animal cells would have utility in plants. Therefore potential herbicides include, but are not limited to, inhibitors of plant homologues of ras, raf, protein tyrosine kinases, protein tyrosine phosphatases. Potential herbicides also include reagents which would inhibit intracellular activation of the glutamate receptor therefore blocking activation of downstream signaling cascades.

Herbicides which act via the GluR signaling pathway but are too large to cross the blood-brain barrier are especially preferred since they would be relatively non-toxic to humans and animals. For example, glutamate analogs such as PPT in theory should also be toxic to animals, as animals possess GS and glutamate receptors. However, PPT is not toxic to animals, as it does not pass the blood-brain barrier and effectively excreted in kidneys. This indicates that there may be plenty of room for constructing a herbicide which only affects plants but not animals. In addition, since the plant iGluR described herein appears to be "novel" in structure (combines kainate and NMDA domains), it is possibly distinct from those animal iGluRs and may be used to develop plant-specific herbicides.

In examples described below, glutamate is shown to induce the expression of a gene for asparagine synthetase (ASN1) in *Arabidopsis thaliana*. Thus, glutamate, an amino acid thought to be involved in nitrogen transport, can also act as a signaling molecule in plants. Arabidopsis cDNAs with high identity to a ionotropic animal glutamate receptor (iGluR) as well as one with high identity to animal metabotropic glutamate receptor (mGluR) are identified herein. The data described below shows that kainate, an iGluR agonist, can mimic the glutamate-stimulated induction of ASN1 mRNA. Conversely, an iGluR antagonist (DNQX) partially blocks the induction of ASN1 mRNA by glutamate. These data indicate that Arabidopsis possesses a functional iGluR.

6. EXAMPLE

Identification and Characterization of Arabidopsis Homologs of the Animal Glutamate Receptor Gene Two Arabidopsis cDNA clones contained in the Arabidopsis Expressed Sequence Tag (EST) databank (Newman et al., 1994, Plant Physiol. 106:1241–1255). Two cDNA clones each with identity to a distinct type of animal glutamate receptor. One Arabidopsis cDNA clone (EST#107M14T7, pAt-iGR-1) shares high identity to a class of glutamate receptors called ionotropic (iGluR) receptors which constitutes ligand-gated ion channels (Gasic, G. P. and Hollmann, 1992, Annu. Rev. Physiol. 54:507–536; Kanai et al., 1993, TINS 16:36–370; O'Hara et al., 1993, Neuron 11:41–52; Seeburg, Ph.D., 1995, TINS 16:359–365. A second Arabidopsis cDNA (EST# 97C23T7, pAT-mGR-1) shares identity to another class of animal glutamate receptors called metabotropic glutamate receptor, mGluR (Gasic, G. P. and Hollmann, 1992, Annu. Rev. Physiol. 54:507–536).

6.1. The iGluR cDNA Clone

Sequence analysis of each clone indicates that the Arabidopsis iGluR cDNA, pAt-iGR-1, shares extensive identity with animal iGluRs. About 700 nucleotides from the 5' end of the clone pAt-iGR-1 have been sequenced. This clone encodes a truncated peptide which shares an extended region of homology with the ionotropic glutamate receptor which cover part of the glutamate-binding site close to transmembrane domain I (TMI) and continues through TMII until the end of TMIII (FIG. 5 and FIG. 7A). The highest identity to animal iGluR is in the glutamate-binding domain (52%) (FIG. 6). The glutamate-binding region of animal iGluR is a two cleft domain shown by the hatched bars in FIG. 5. The Arabidopsis sequence shown in FIG. 6, corresponds to the first of these glutamate-binding domains in animal iGluR (FIG. 5). The glutamate-binding domain shared between animal and plant iGluR has low but significant identity to the glutamine-binding domain of an *E. coli* permease gene (Nakanishi et al., 1990, Neuron 5:569–581) (FIG. 6). The ligand-binding R residue, which is conserved in all ionotropic glutamate receptors, is also conserved in the Arabidopsis iGluR (Kuryatov et al., 1994, Neuron 12:1291–1300).

The mRNAs of non-NMDA type iGluRs (kainate-binding iGluR and AMPA iGluR) are subject to RNA editing which modifies their function. For example, in the GluR2 subunit in AMPA type iGluR, RNA editing (Q to R) in TM II (FIG. 1) has been shown to regulate the Ca++ permeability. RNA editing leads to a decrease in Ca++ permeability (Choi, D. W., 1988, Neuron 1:623–634; Hume et al., 1991, Science 253:1028–1031). In Kainate-binding type iGluR, both the GluR5 and GluR6 subunits display Q to R editing similar to that of the GluR2 subunit of AMPA receptors (Sommer et al., 1991, Cell 67:11–19). GluR6 has two additional positions in TMI that are modified by RNA editing (Kohler et al., 1993, Neuron 10:491–500). For GluR6, only when TMI is edited does editing in TMII (Q to R) influence Ca++ permeability (Kohler et al., 1993, Neuron 10:491–500). In contrast to the AMPA receptor channel, GluR6(R) channels edited in TMI show a higher Ca++ permeability than GluR6 (Q) channels (Kohler et al., 1993, Neuron 10:491–500). In the case of NMDA type iGluR, all of the subunits do not show RNA editing in TMI and TMII. In fact all subunits contain an N at the site at which Q to R editing occurs. NMDA receptors are highly permeable to Ca++.

Interestingly, the Q/R residue of non-NMDA-type ionotropic glutamate receptor which are subject to RNA editing or the corresponding non-editing N residue of NMDA-type ionotropic glutamate receptor within TMII (Seeburg, P. H., 1995, TINS 16:359–365), are missing from the predicted peptide of Arabidopsis pAt-iGR-1. Since these residues are important for the regulation of permeability of Ca++ ions in animal ionotropic glutamate receptors (Burnashev et al., 1992, Neuron 8:189–198; Kohler et al., 1993, Neuron 10:491– 500; Sommer et al., 1991, Cell 67:11–19) the Ca++ ion permeability in plant glutamate receptors may be regulated by a different mechanism.

Sequence searches of GeneBank data using FASTA program show that the peptide encoded by Arabidopsis pAt-iGR-1 has a strong homology to all of the kainate-binding, NMDA, and AMPA types of animal iGluRs, although it seems to have a slightly higher overall homology to kainate-binding type of iGluRs. FIG. 7A shows the extensive homology between the peptide encoded by the first 700 nucleotides of Arabidopsis pAt-iGR-1 to a NMDA and a kainate-binding iGluR (FIG. 7A). In contrast to animals which have distinct kainate and NMDA receptors, plants may possess a "novel" type of iGluR that combines domains of kainate and NMDA receptors.

Northern blot analysis of leaf, root and flower tissues show that the iGluR mRNA is expressed at detectable levels (FIG. 9). In these experiments twenty μg of total RNA isolated from each of the leaf, root and flower tissues were electrophoresed on a 1% formaldehyde agarose gel. The Northern blot analyses were performed with high-stringency conditions at a temperature of 42° C. in 50% (v/v) formamide hybridization solution. Washing and chemiluminescent detection were performed according to the Boehringer-Mannheim Genius System User's Guide. This Northern shows iGluR mRNA is detected in 20 μg of total RNA. This Northern blot analysis also shows that Arabidopsis iGluR in RNA (2.7 Kb) is of comparable size to animal iGluR mRNA (3.0 Kb) (FIG. 8). The Arabidopsis iGluR mRNA is expressed predominantly in leaves and also at lower levels in roots and flowers of Arabidopsis.

6.2. The mGluR cDNA Clone

The Arabidopsis clone pAT-mGR-1 (EST #97C23T7) shares a high degree of homology to an animal mGluR as shown in FIG. 7B. The homologous region between Arabidopsis mGluR and animal mGluR includes part of the cysteine-rich region of animal mGluR and spans part of the 7 transmembrane domains (O'Hara et al., 1993, Neuron 11:41–52). In the Arabidopsis pAt-mGR-1 clone, there are several C residues in the cysteine-rich signature region as well (FIG. 7B).

Genomic Southern analyses demonstrate that the iGluR of Arabidopsis are bona-fide Arabidopsis genes as shown by the strongly hybridizing DNA fragments in Arabidopsis genomic DNA under high stringency condition (FIG. 8). The weakly hybridizing bands in each lane indicate that there may be additional GluR genes in the Arabidopsis genome. In these Southern blot analyses, two μg of CsCl-purified Arabidopsis genomic DNA was digested with different restriction enzymes. The digested DNA was electrophoresed on a 1% (w/v) Tris-phosphate-EDTA agarose gel. The DNA was transferred to a nylon membrane after depurination, denaturation and neutralization steps. Hybridization steps were carried out under high stringency conditions (65° C. in 0.5×SSC) or low stringency conditions (50° C. in 1×SSC).

Southern blot analyses using the Arabidopsis iGluR cDNAs on genomic DNA from other dicots (tobacco), a legume (pea), and two monocots (corn and rice) were performed under low-stringency conditions. This Southern blot analysis demonstrates that all plant species possess the iGluR genes described for Arabidopsis.

Genomic Southern blot analysis using Arabidopsis mGluR cDNA on genomic DNA from other dicots (tobacco), a legume (pea) and two monocots (corn and rice) were performed under low stringency conditions (50° C. in 1×SSC). The analysis demonstrated bands hybridizing to the mGluR in all species.

7. EXAMPLE

Use of iGluR Agonist (KA) and Antagonist (DNQX) to Define a Functional iGluR in Arabidopsis The Arabidopsis iGluR cDNA (pAt-iGR-1) shows high identity to the animal glutamate receptors specifically activated by an iGluR agonist called kainic acid (KA). These kainate-selective iGluR receptors are competitively inhibited by an iGluR antagonist called 6,7-dinitroquinoxaline (DNQX). This iGluR agonist (KA) and antagonist (DNQX) are structurally distinct from glutamate (see FIG. 10), yet they bind to the iGluR receptor and stimulate or inhibit its action. Thus, any responses which these drugs may effect in plants, are likely to be due to their specific interaction with a iGluR-type receptor, rather than to general effects caused by inhibition of glutamate-utilizing enzymes. The experiments described below show that agonists, such as KA, mimic the effects of glutamate on gene induction and by contrast, that antagonists such as DNQX suppress glutamate gene induction. Thus, these experiments provide evidence that plants express a functional GluR.

7.1. Effect of GluR Agonists and Antagonists on Plant Growth

A dose-response curve using various concentrations of KA or DNQX was performed and the effects of each drug on plant growth was determined by measuring root length on vertical tissue culture plates (see FIG. 11). Low concentrations of agonist (KA) have no adverse effects on plant growth (FIG. 1A, left panel, compare 0 to 0.3 mM KA). Low concentrations of DNQX also have no adverse affects on growth (FIG. 11B, left panel, compare 0 to 0.1 mM KA). At high concentrations of agonist (KA) or antagonist (DNQX), a reduction in root growth is observed (FIGS. 11A & B, right panels, black bars). In each case, the effect of high doses of KA or DNQX is at least partially reversed by glutamate supplementation (FIGS. 12A & B, right panels, white bars). The partial rescue by glutamate indicates that the inhibitory effects of high KA or DNQX are specific to a glutamate-related process.

7.2. The iGluR Agonist (KA) is Able to Induce the Expression of Plant Nitrogen-Assimilatory Genes The ability of a iGluR agonist to mimic the glutamate-stimulated expression of nitrogen assimilatory genes in Arabidopsis was tested using low concentrations of agonist KA and monitoring ASN1 mRNA levels as a measure of gene induction by KA. The results demonstrate that this iGluR agonist pair can specifically affect the expression of nitrogen metabolic genes in Arabidopsis. These data provide evidence that plants possess a functional glutamate receptor.

ASN1 mRNA accumulates to high levels specifically in dark-treated plants (FIG. 12A, lane 2), and is repressed by light (FIG. 12A, lane 1) or sucrose (FIG. 12A, lane 3). The results demonstrate that glutamate is able to partially relieve this sucrose repression (FIG. 12A, compare lane 6 to lane 3). Two concentrations of the iGluR agonist KA (300 uM and 30 μM) are each able to relieve the: sucrose repression of ASN1 mRNA (FIG. 12A, lanes 4 & 5). ASN1 mRNA levels-are determined by Northern blot analysis. FIG. 12B shows a quantitative bar graph of these Northern blot results.

Quantitatively, KA and glutamate are each able to relieve the sucrose repression of ASN1 mRNA to nearly equivalent levels (FIG. 12C). This roughly 2-fold induction of ASN1 mRNA by KA or glutamate is comparable to the level of metabolic induction of several amino acid genes in yeast (2–4 fold) (Zalkin, H. and Yanofsky, C., 1982, J. Biol. Chem. 257:1491–1500). Conversely, the iGluR antagonist DNQX seems to partially inhibit glutamate-induction of ASN1 mRNA (FIGS. 12A & B, compare lanes 6 & 7). The discovery that an iGluR agonist can mimic glutamate induction of a plant gene indicates that a functional iGluR glutamate receptor exists in plants.

7.3. Linking the Arabidopsis iGluR Gene to a Functional Glutamate Receptor in Plants The next experiments demonstrate that the iGluR gene(s) is responsible for the observed in vivo responses of ASN1 gene expression to iGluR agonist (KA) or iGluR antagonist (DNQX), using a genetic approach. Arabidopsis mutants are screened for insensitivity or supersensitivity to the iGluR agonist KA or antagonist DNQX. Arabidopsis mutants were selected in which a mutation in a iGluR gene may improve or disturb the binding affinity of the agonist or antagonist. In this assay, Arabidopsis seeds are plated on tissue culture plates in Ms Medium (Murashige & Skoog Salt Mixture-plant basic medium available from Gibco (BRL). Agonists and antagonists are added in serial dilution to the medium. The plates are grown vertically in a growth chamber at 22° C. with a 16 hour light/8 hour dark cycle for two weeks. The effect of agonists and antagonists is determined by changes in root length. Mutagenized M2 Arabidopsis seedlings were screened for those which are insensitive (resistant) to the iGluR agonist (KA) or antagonist (DNQX) by screening for long roots on high concentrations of either drug (FIG. 15A). Conversely, mutants that are super-sensitive to either drug are being identified by screening for seedlings with short roots on low doses of KA or DNQX (FIG. 14B).

8. EXAMPLE

Use of Agonists and Antagonists to Define a Functional mGluR in Arabidopsis

The Arabidopsis mGluR cDNA (pAt-mGR-1) shows high identity to the animal glutamate receptors specifically activated by mGluR agonists called L-AP4 and ACPD. These mGluR receptors are specifically inhibited by mGluR antagonists L-AP3 (L-(+) amino phosphoropropionate) and L-ABHA (L-aspartate-B-hydroxymate). Any responses which these drugs may effect in plants are likely due to their specific interaction with an mGluR-type receptor, rather than to general effects caused by inhibition of glutamate-utilizing enzymes. In order to test that plants express a functional mGluR the assay described herein can be used, wherein agonists such as L-AP4 and ACPD will mimic the effects of glutamate on gene induction and by contrast antagonists such as L-AP3 and L-ABHA suppress glutamate gene induction. The effects of these agonists/antagonists can be tested using the vertical root growth assay as described in the working example, Section 7. Serial dilutions of the agonists/antagonists to be tested can range from 3 mM to 0 mM. In each case, the effects of doses of L-AP3, L-ABHA, L-AP4 and ACPD should be reversed by glutamate supplementation, indicating that the effect of these drugs are specific to glutamate related processes.

9. EXAMPLE

The Complete Sequence of the iGluR cDNA

The nucleotide deduced amino acid sequence of the full length Arabidopsis iGluR cDNA called iGlr1 was determined (five pages long) (FIG. 15). The nucleotide sequence of the full-length Arabidopsis iGlr1 cDNA clone (see below) is shown, as is the deduced encoded protein. The regions of highest homology to animal iGluR are denoted in FIGS. 17 & 18. The full-length Arabidopsis iGlr1 cDNA clone was constructed as follows: the partial EST cDNA clone 107M14T7 was used as a hybridization probe to isolate two additional iGlr cDNA clones (HM299 and HM262) from two different Arabidopsis cDNA libraries, KC-HM1 and CD4–7 (obtained from the Arabidopsis stock center, Ohio). Portions of each iGlr cDNA clone were annealed to generate a full-length Arabidopsis iGlr1 cDNA which was given the trivial name HM330.

10. EXAMPLE iGluR Antagonist DNQX Phenocopies Plant Mutants Impaired in Light Signal Transduction This example demonstrates that a specific antagonist of iGluR, DNQX, phenocopies plant mutants impaired in light signal transduction. Light induces leaf expansion and chloroplast development (greening) in Arabidopsis. Light also inhibits hypocotyl elongation. Plants germinated in the dark show an etiolated morphology, yellow unopened cotyledons and long hypocotyl.

Light normally promotes greening and inhibits hypocotyl elongation in wild-type seedlings. hy mutants are impaired in light perception/signal transduction. hy mutants when grown in light take on the morphology of dark-grown seedlings (long-hypocotyl) (FIG. 20). When wild-type plants are treated with DNQX, an iGluR antagonist, they grow as hy mutants (long hypocotyl). Plants grown on normal MS media show a short hypocotyl, while plants grown on media containing 400 $\mu$M DNQX show elongated hypocotyl, similar to hy mutants (FIG. 21).

Plants grown in darkness have unopened yellow cotyledons, but if exposed to light for 5 hrs. the cotyledons begin to green. If plants are grown in the dark with DNQX in the media, the cotyledons remain yellow and unopened even after 5 hrs. of light exposure. Thus DNQX blocks light-induced chloroplast development in Arabidopsis (FIG. 22).

In conclusion, DNQX a specific antagonist of iGlur, inhibits the plant's responses to light signal transduction, e.g., induction of leaf expansion and chloroplast development (greening).

11. EXAMPLE iGluR Antagonist DNQX Inhibits Light Induced Chlorophyll Synthesis

This example demonstrates that a specific antagonist of iGluR, DNQX, phenocopies plant mutants impaired in light signal transduction. Light induces synthesis of chlorophyll a and chlorophyll b in Arabidopsis, and treatment with DNQX inhibits this light induced response.

Arabidopsis seedlings were sown on MS+3% sucrose agar plates and grown in complete darkness for 5 days. On day 6, half of the seedlings were kept in the dark (D) and the other half were transferred to white light (L) for 7.5 hours and were grown in the presence or absence of 0.4 mM DNXQ (FIG. 31). Levels of chlorophyll a and chlorophyll b were measured using the method of Moran (Moran et al., 1982, Plant Physiol. 69:1376–13810). The cotyledons of 30–40 plants were used for each data point.

The presence of DNQX significantly inhibits synthesis of chlorophyll a and b in Arabidopsis plants grown in the light.

Therefore DNQX, a specific antagonist of iGluR, inhibits the plant's responses to light signal transduction to induce synthesis of chlorophyll.

12. EXAMPLE

The iGluR Agonist Kainate (KA) Inhibits Light-Induced Germination

Kainate inhibition of germination in the dark is reversed by glutamate. Plants germinated in the dark on "normal" MS media (MS) as a positive control. Kainate, the iGluR agonist, causes a specific inhibition of germination of plants grown in MS media containing KA. The inhibition of germination by KA is reversed by the addition of glutamate to the media (MS+KA+Glu) (FIG. 23). Germination involves a light signal. Dark-grown seedlings are sown in the light and transferred to the dark. These results indicate that at high concentrations, the iGluR agonist is able to block light-induced germination, and that glutamate the natural agonist for iGluR can reverse the inhibitory effect of high KA. High doses of KA an agonist of iGluR in animals functions as a neurotoxin.

The effects of kainate on germination of Arabidopsis in the dark was determined. Arabidopsis seedlings germinated on media containing increasing amounts of kainate (200–400 uM) show a significant inhibition of germination of dark-grown seedlings. This inhibition of germination is likely to be specific to iGluR as it is specifically reversed by the supplementation of glutamate to the growth media (FIG. 23).

13. EXAMPLE

The Arabidopsis iGlr-1 Gene Maps to Chromosome III

The Arabidopsis iGlr-1 gene was mapped using recombinant inbred lines of Arabidopsis. An RFLP for iGlr1 was identified in the wild-type Arabidopsis ecotypes Columbia (C) and Landsberg (L). This iGlr1-specific RFLP was used to identify the genotype of the iGlr1 gene in 30 Recombinant Inbred lines as being derived from the C or L parents. The "pattern" of inheritance of the iGlr1 gene in the recombinant inbred lines was compared to known markers and used to determine a map position (see FIG. 24).

The iGlr-1 gene maps to chromosome III to a similar position as two known mutants, hy2 and spy (FIG. 25). Using data from recombinant inbred lines hy2 is a mutant impaired in light signal transduction (see review Whitelam & Harberd, Plant Cell Environment 1994, 17, 615–625. The spy mutant is impaired in GA hormone signal transduction (Jacobsen & Olszewski, 1993, Plant Cell 5, 887–896).

14. EXAMPLE

Isolation of Arabdiopsis Mutants Super Sensitive to DNQX

In this assay Arabidopsis mutants were screened for altered sensitivity to the iGluR antagonist DNQX. Mutants affected in iGluR can be used to test the in vivo function of plant iGluR and could also be mapped relative to the cloned gene. To isolate mutants in Arabidopsis iGluR plants were screened for super-sensitivity to the iGluR antagonist DNQX. Normally wild-type Arabidopsis only show an elongated hypocotyl phenotype when exposed to high doses of DNQX (200–400 uM) and show no hypocotyl elongation at low concentrations (100 uM) (see FIG. 21). The ems mutagenized M2 seeds were germinated on media containing 100 uM DNQX and mutants that displayed an elongated hypocotyl at this low dose of DNQX were selected.

Putative Arabidopsis mutants that are super-sensitive to the iGluR antagonist DNQX were isolated. Arabidopsis wild-type seedlings that show no significant hypocotyl elongation when germinated on 100 uM DNQX were compared to control MS. By contrast the putative DNQX supersensitive mutant shows an elongated hypocotyl when germinated on 100 uM DNQX. The putative super-sensitive mutant also demonstrates an elongated hypocotyl compared to wild-type when germinated in the absence of DNQX. An additional DNQX supersensitive mutant was isolated that demonstrated a homeotic phenotype. Lateral roots emerged from the elongation hypocotyl of the plant (see FIG. 33). In wild type plants, lateral roots emerge only from roots.

Thus mutations in iGluR caused a phenotype of light-insensitivity, supporting the Applicants' model.

15. EXAMPLE

Arabidopsis Mutants Resistant to Kainate Display a Giant Phenotype

Arabidopsis mutants resistant to the iGluR agonist Kainate were selected. High doses of kainate (12 mM) kill wild-type seedlings. This is not unexpected as high doses of the iGluR agbnist kainate function as a neurotoxin in animals. Arabidopsis mutants with putative defects in the KA binding site of iGluR were selected by selecting for mutants able to grow in the presence of 12 mM kainate. The ems mutagenized Arabidopsis M2 seedlings were sown on 12 mM kainate. Note the one KA-resistant plant is enlarged in Panel B, (FIG. 28).

Arabidopsis mutants resistant to the iGluR agonist kainate, display a Giant phenotype. Two independent Arabidopsis were mutants selected for growth on 12 mM KA (see FIG. 28). When the putative KA-resistant plants are transferred to soil, they each display varying degrees of a Giant vegetative phenotype. This result may indicate that iGluR affects/enhances overall plant growth.

Two additional independent KA-resistant mutants (KA-giant-1 and KA-giant-2) show a giant, late flowering phenotype (FIG. 32). Some of the cauline leaves from the flowering stalks of these KA-resistant giant mutants (panel B) display the morphology of rosette leaves in contrast to the normal morphology in wild type plants (panel A). These results suggest that iGluR may be involved in flowering and developmental processes.

A number of references have been cited and the entire disclosure of which are incorporated herein by reference.

The present invention is not to be limited in scope by the specific embodiments described which are intended as single illustrations of individual aspects of the invention, and functionally equivalent methods and components are with in the scope of the invention. Indeed various modifications of the invention, in addition to those shown and described herein will become apparent to those skilled in the art from the foregoing description and accompanying drawings. Such modifications are intended to fall within the scope of the appended claims.

What is claimed is:

1. A method for identifying a compound that modulates the growth of a plant through a glutamate-related process, comprising:

a) exposing a plant that expresses or over expresses a plant glutamate receptor to a test compound in the absence of glutamate, wherein the plant glutamate receptor has glutamate binding activity and comprises an amino acid sequence selected from the following:

i) an amino acid sequence encoded by a nucleic acid that hybridizes under highly stringent conditions to the complement of the coding sequence of the nucleotide sequence of SEQ ID NO: 13, 14, or 15, wherein said highly stringent conditions include washing in 65° C. in 0.5×SSC;

ii) the glutamate binding domain comprising SEQ ID NO: 1;

iii) the amino acid sequence comprising SEQ ID NO: 33;

iv) the glutamate binding domain comprising SEQ ID NO: 8; and v) the glutamate binding domain comprising SEQ ID NO :12;
b) exposing a plant that expresses or over expresses the plant glutamate receptor described in step a) to the test compound in the presence of glutamate; and
c) measuring and comparing growth of the plant of step a) with that of the plant of step b);

in which a difference in growth indicates that the compound modulates plant growth through a glutamate-related process.

2. A method for identifying a compound that modulates the activity of a plant glutamate receptor, comprising:
a) exposing a genetically engineered host cell to a test compound in the absence of glutamate, wherein the host cell both expresses or over expresses a plant glutamate receptor and responds to the signal transduced by the receptor, and the plant glutamate receptor has glutamate binding activity and comprises an amino acid sequence selected from the following:
  i) an amino acid sequence encoded by a nucleic acid that hybridizes under highly stringent conditions to the complement of the coding sequence of the nucleotide sequence of SEQ ID NO: 13, 14, or 15, wherein said highly stringent conditions include washing in 65° C. in 0.5×SSC;
  ii) the glutamate binding domain comprising SEQ ID NO: 1;
  iii) the amino acid sequence comprising SEQ ID NO: 33;
  iv) the glutamate binding domain comprising SEQ ID NO: 8; and
  v) the glutamate binding domain comprising SEQ ID NO:12;
b) exposing a genetically engineered host cell to the test compound in the presence of glutamate that expresses or over expresses the plant glutamate receptor described in step a); and
c) measuring and comparing the response of the host cell of step a) with that of the host cell of step b);

in which a difference in the response of the cells indicates that the compound modulates the activity of a plant glutamate receptor.

3. A method for identifying a compound that binds to a plant glutamate receptor, comprising:
a) exposing a genetically engineered host cell that expresses or over expresses the plant glutamate receptor to a test compound, wherein the plant glutamate receptor comprises an amino acid sequence selected from the following:
  i) an amino acid sequence encoded by a nucleic acid that hybridizes under highly stringent conditions to the complement of the coding sequence of the nucleotide sequence of SEQ ID NO: 13, 14, or 15, wherein said highly stringent conditions include washing in 65° C. in 0.5×SSC;
  ii) the glutamate binding domain of SEQ ID NO: 1;
  iii) the amino acid sequence of SEQ ID NO: 33;
  iv) the glutamate binding domain of SEQ ID NO: 8; and
  v) the glutamate binding domain of SEQ ID NO:12; and
b) measuring the binding of the test compound to the glutamate receptor expressed or over expressed in the host cell, in which binding of the test compound to the plant glutamate receptor indicates that the test compound interacts with the plant glutamate receptor.

4. A method for identifying a compound that binds to a plant glutamate receptor, comprising:
a) exposing an isolated plant glutamate receptor to the test compound, wherein the plant glutamate receptor comprises an amino acid sequence selected from the following:
  i) an amino acid sequence encoded by a nucleic acid that hybridizes under highly stringent conditions to the complement of the coding sequence of the nucleotide sequence of SEQ ID NO: 13, 14, or 15, wherein said highly stringent conditions include washing in 65° C. in 0.5×SSC;
  ii) the glutamate binding domain of SEQ ID NO: 1;
  iii) the amino acid sequence of SEQ ID NO: 33;
  iv) the glutamate binding domain of SEQ ID NO: 8; and
  v) the glutamate binding domain of SEQ ID NO:12; and
b) measuring the binding of the test compound to the isolated plant glutamate receptor.

5. A method for identifying a compound that modulates the growth of a plant through a glutamate-related process, comprising:
a) exposing a plant that expresses or over expresses a plant glutamate receptor to a test compound in the presence of glutamate, wherein the plant glutamate receptor has glutamate binding activity and comprises an amino acid sequence selected from the following:
  i) an amino acid sequence encoded by a nucleic acid that hybridizes under highly stringent conditions to the complement of the coding sequence of the nucleotide sequence of SEQ ID NO: 13, 14, or 15, wherein said highly stringent conditions include washing in 65° C. in 0.5×SSC;
  ii) the glutamate binding domain comprising SEQ ID NO: 1;
  iii) the amino acid sequence comprising SEQ ID NO: 33;
  iv) the glutamate binding domain comprising SEQ ID NO: 8; and
  v) the glutamate binding domain comprising SEQ ID NO:12;
b) exposing a plant that expresses or over expresses the plant glutamate receptor described in step a) to the test compound in the presence of both glutamate and a glutamate-antagonist; and
c) measuring and comparing growth of the plant of step a) with that of the plant of step b);

in which a difference in growth indicates that the compound modulates plant growth through a glutamate-related process.

6. A method for identifying a compound that modulates the activity of a plant glutamate receptor, comprising:
a) exposing a genetically engineered host cell to a test compound in the presence of glutamate, wherein the host cell both expresses or over expresses a plant glutamate receptor and responds to the signal transduced by the receptor, and the plant glutamate receptor has glutamate binding activity and comprises an amino acid sequence selected from the following:
  i) an amino acid sequence encoded by a nucleic acid that hybridizes under highly stringent conditions to the complement of the coding sequence of the nucleotide sequence of SEQ ID NO: 13, 14, or 15, wherein said highly stringent conditions include washing in 65° C. in 0.5×SSC;
  ii) the glutamate binding domain comprising SEQ ID NO: 1;
  iii) the amino acid sequence comprising SEQ ID NO: 33;

iv) the glutamate binding domain comprising SEQ ID NO: 8; and v) the glutamate binding domain comprising SEQ ID NO:12;

b) exposing a genetically engineered host cell to the test compound in the presence of both glutamate and a glutamate-antagonist, wherein the host cell expresses or over expresses the plant glutamate receptor described in step a); and c) measuring and comparing the response of the host cell of step a) with that of the host cell of step b);

in which a difference in the response of the cells indicates that the compound modulates the activity of a plant glutamate receptor.

7. The method of claim 1 or 5 wherein the plant exposed in step a) and the plant exposed in step b) have been altered to effect the sensitivity of the plant to the test compound.

* * * * *